United States Patent [19]

Brewitt

[11] Patent Number: 6,024,734
[45] Date of Patent: Feb. 15, 2000

[54] TREATMENT METHODS USING HOMEOPATHIC PREPARATIONS OF GROWTH FACTORS

[76] Inventor: Barbara A. Brewitt, 5557 36th Ave. NE., Seattle, Wash. 98105

[21] Appl. No.: 08/855,096

[22] Filed: May 13, 1997

Related U.S. Application Data

[63] Continuation-in-part of application No. 08/710,040, Sep. 10, 1996, Pat. No. 5,629,286, which is a continuation of application No. 08/488,722, Jun. 8, 1995, abandoned, which is a continuation-in-part of application No. 08/221,365, Mar. 31, 1994, abandoned.

[51] Int. Cl.[7] .................................................. A61M 31/00
[52] U.S. Cl. ........................... 604/500; 604/890.1; 514/2; 514/9; 514/19; 530/351; 530/303
[58] Field of Search ................................ 604/500, 890.1, 604/501, 502, 503, 504, 505, 514, 530

[56] References Cited

FOREIGN PATENT DOCUMENTS 2695556  3/1994  France .
2695557  3/1994  France .

OTHER PUBLICATIONS

Adrenalinum, Official Homeopathic Monographs from General Pharmacy of the Homeopathic Pharmacoepia of the United States, Pharmacoepia Convention of the American Institute of Homeopathy, 0044, Dec. 1989.
Thyroidinum, Official Homeopathic Monographs from General Pharmacy of the Homeopathic Pharmacoepia of the United States, Pharmacoepia Convention of the American Institute of Homeopathy, 9048, Jun. 1993.
Adrenocorticotrophin, Official Homeopathic Monographs from General Pharmacy of the Homeopathic Pharmacoepia of the United States, Pharmacoepia Convention of the American Institute of Homeopathy, 0045, Dec. 1989.
Julian, Parathyroid Hormone, *Materia Medica of New Homeopathic Remedies*, 388–389, 1979.
Julian, Thyreotrophic Hormone, *Materia Medica of New Homeopathic Remedies*, 530–533, 1979.
Julian, Corticotrophin (ACTH), *Materia Medica of New Homeopathic Remedies*, 179–180, 1979.
Julian, Cortisone and Corticoids, *Materia Medica of New Homeopathic Remedies*, 186–188, 1979.
Julian, Folliculinum, *Materia Medica of New Homeopathic Remedies*, 231–232, 1979.
E. Pimentel, Guanosine Triphospate–Binding Proteins, *Handbook of Growth Factors Vol I: General Basic Aspects*, Chapter 5, 115–129, 1994.
Bellavite et al., Homeostasis, Complexity and Homeopathy: The Law of Similars, *Homeopathy—A Frontier in Medical Science*, Chapter 6, 193–241, 1995.
J. Schulte, Conservation of Structure in Aqueous Ultra High Dilutions, *Kluwer Academic Publishers*, 105–115, 1994.
M.E. Linder et al., G Proteins, *Scientific American*, 56–65, Jul. 1992.
H.P. Guler et al., Short–Term Metabolic Effects of Recombinant Human Insulin–Like Growth Factor I in Healthy Adults, *The New England Journal of Medicine*, vol. 317, 137–140, Jul. 16, 1987.

*Primary Examiner*—Corrine McDermott
*Assistant Examiner*—Kent Gring
*Attorney, Agent, or Firm*—Ann W. Speckman; Janet Sleath

[57] ABSTRACT

The present invention comprises homeopathic dilutions of growth factors and methods for their use. Disorders which may be effectively treated with the compositions of the present invention include chronic viral disorders, such as HIV, AIDS, chronic fatigue syndrome and Epstein-Barr viral infections, cancer, diabetes and depression. Homeopathic dilutions of growth factors are preferably administered orally. In an alternative embodiment, patients are treated with radio frequency signals corresponding to homeopathic dilutions of growth factors.

21 Claims, 34 Drawing Sheets

6,024,734

TREATMENT METHODS USING HOMEOPATHIC PREPARATIONS OF GROWTH FACTORS

CROSS REFERENCE TO RELATED APPLICATIONS

This application is a continuation-in-part of prior U.S. patent application Ser. No. 08/710,040 filed Sep. 10, 1996, issuing May 13, 1997 as U.S. Pat. No. 5,629,286, which is a continuation of U.S. patent application Ser. No. 08/488,722, filed Jun. 8, 1995, now abandoned, which is a continuation-in-part of U.S. patent application Ser. No. 08/221,365 filed Mar. 31, 1994, now abandoned.

FIELD OF THE INVENTION

This invention relates to the treatment of disorders such as chronic viral infections, cancer and diabetes, and conditions such as inflammation, joint and muscle pain, muscle weakness, fatigue, sinus and nasal congestion, breathing difficulties, poor digestion, neuropathy, headaches, reduced mental acuity, poor memory, skin conditions, poor fitness, weight imbalances, and a variety of psychological conditions, such as mood swings, depression, anxiety, confusion and anger, and relates more particularly to the use of homeopathic dilutions of one or more growth factors to treat such disorders. Use of the homeopathic growth factors of the present invention have also surprisingly been demonstrated to increase lean muscle mass while reducing body fat, and improve overall health, fitness and mental clarity. The present invention also relates to homeopathic preparations of growth factors and delivery systems for such preparations.

BACKGROUND OF THE INVENTION

One aspect of this invention relates to the treatment of chronic viral infections by administration of homeopathic dilutions of growth factors. Chronic viral infections, such as herpes simplex virus, Epstein-Barr virus (EBV), human immunodeficiency virus (HIV), papilloma virus, Coxsackie B, hauta virus and hepatitis virus, affect signal transduction mechanisms with deleterious effects within and between the host's immune and nervous systems. During chronic viral infection, host cell signal transduction and cell cycle regulation are altered, often causing cell injury and cell death.

Viruses lack the necessary biochemical machinery to manufacture proteins and must therefore insert their genetic material into a host cell genome in order to proliferate. Viruses consist of a protein coat and genetic material. RNA viruses additionally contain reverse transcriptase, an enzyme that translates the RNA into a DNA strand before insertion in the host cell genome.

During viral infection, the protein coat binds to the host cell's surface membrane enabling viral genetic information to subsequently enter the host cell. Entry occurs via various methods, one of which is attachment to specific membrane receptors, including growth factor receptors. For example, the cell receptors for the Epstein Barr and herpes simplex type 1 viruses have been identified as the third component of the complement receptor and the fibroblast growth factor receptor, respectively. Insertion of viral genetic information into the host cell's genome subverts the cell's normal metabolic and genetic mechanisms in order to prioritize viral gene expression and replication.

Chronic, or long-term, viral infections occur when the virus overcomes or effectively disrupts the normal neuronal and immunological defense mechanisms of the host. During early infection, several viruses, such as herpes simplex virus, EBV, human herpes 6 virus (HH6V), hepatitis and HIV can be asymptomatic as immune responses and viral replication remain in balance in specific cell populations. Viral replication occurs in response to extracellular stimuli (Garcia-Blanco, M. A. and Cullen, B. R. 1991 Science 254:815–820). Infections persist as continuous viral replication occurs without substantial disruption of host cell function. Chronic viral infections terminate only when viral replication is disrupted.

Viral infection erodes feedback communication between the host's immune and nervous systems. For example, synthesis of adrenocorticotrophic hormone (ACTH) by lymphocytes after viral infection disrupts the normal feedback loop between pituitary/hypothalamus secretion of ACTH and the adrenal gland's synthesis of glucocorticoids in response to ACTH signals. Over-expression of ACTH causes increased expression of gllucocortiods which consequentially down-regulates the pituitary and suppresses the activities of T lymphocytes. This constant stress response often leads to extreme fatigue and exhaustion on patients with chronic viral infections. In an immune compromised patient, chronic infection leds to entry of virions into the bloodstream, the lymphatic vessels and/or the nerve pathways resulting in infection of new and distant cell populations.

Long-term DNA viral infections correlate with chronic of cancerous illnesses. For example, hepatocellular carcinoma 58% of the time compared to 17% in a control group. EBV infection was correlated with Hodgkin's disease of the mixed cellularity type 60% of the time. Herpes type viral nucleic acid sequences from herpes simplex 1 and 2, cytomegalovirus and EBV was found in the cerebrospinal fluid of patients with acute encephalitis. HH6V has been found to be a cofactor in causing chronic fatigue syndrome and AIDS. The ability of viruses to cause cancer is contained within specific sequences of the viral genome, known as oncogenes, that modulate gene transcription and regulation.

Gene transcription and regulation are modulated under normal conditions by growth factors. Growth factors are cell signaling polypeptides that bind to specific cell membrane receptors and initiate a cascade of intracellular events that affect cell proliferation and differentiation. As stated above, many growth factors bind to the same cell surface receptors as viruses and therefore activate the same metabolic pathways used by viral infected or transformed cells.

There are gene sequence homologies between growth factors, proto-oncogenes and viral oncogenes. Normal non-cancer cells contain proto-onocogenes that are homologous to the oncogene sequences found in some cancer causing viruses. Proto-oncogene as well oncogene sequences have the power to regulate the cell cycle. Growth factors regulate the cell cycle by manipulating proto-oncogenes. Some proto-oncogene sequences are homologous with growth factors or their receptors. For example, the B chain of platelet-derived growth factor (PDGF) is homologous to the proto-oncogene c-sis (Doolittle, R. F., et al. 1983 Science 221:275–77). The receptor for epidermal growth factor (EGF) is homologous to the proto-oncogene c-erbb (Downward, et al. 1984 Nature 307:521–527).

Growth factors and viruses use the same transcription sites to regulate cell proliferation and/or viral replication, and are thus in a somewhat competitive state with one another. For example, TGFβ plays a critical role in the transmission of biological information by acting as an on/off switch that couples cell behavior to the external environment. Within the TGFβ promoter lies the proto-oncogene c-fos which codes for key transcription factors located at AP-1 transcription sites. Subversion of c-fos gene expression by HIV enhances HIIV transcription and replication independent of control sites located at tat and $NF_k\beta$ (Roebuck, K. A. et al. 1993 J. Clin. Invest. 92:1336–1348). Viral transcription in the human T-cell leukemia virus type 1 (HTLV-1), a virus with many characteristics similar to HIV, is tightly regulated by a Tax transactivator site located at the c-fos AP-1 site within the TGFβ promoter (Kim et al. 1990 J. Exp. Med. 172:121–129). When the TGFβ promoter is activated so is HTLV-1 Tax. Chronic viral infection coincides with aberrant expression of growth factors throughout the body as viruses have evolved to successively overcome the regulatory actions of their competitors, growth factors.

Chronic viral infections can lead to up-regulation of growth factor expression. For example, HIV infection up-regulates expression of tumor necrosis factor alpha (TNFα) and transforming growth factor beta (TGFβ). Overexpression of either of these growth factors disrupts normal transcriptional control of gene expression, leading to suppression of hematopoietic progenitor cells and increased HIV replication. TGFβ, secreted by HIV-infected lymphocytes, also promotes growth of Kaposi's sarcoma cells, fibroblasts and endothelial cells.

Specific hemopoietic growth factors have been used to treat diseases such as AIDS and cancer. Hemopoietic growth factors are logical therapeutic immunomodulators to use for treatment of chronic viral infections and other diseases for several reasons. First, endogenous growth factors such as granulocyte-macrophage colony stimulating factor (GM-CSF) and macrophage colony stimulating factor (M-CSF) stimulate proliferation of hemopoietic progenitor cells. Second, lymphocytes, macrophages and natural killer cells that normally produce these factors are quantitatively and qualitatively defective after infection by HIV, HH6V or EBV. Third, primates infused with GM-CSF showed low toxicity with some positive but inconsistent rises in platelet number.

However, clinical studies on AIDS patients using GM-CSF and M-CSF at pharmacological concentrations (ug/kg/day) have produced mixed results. For example, injections or intravenous administration of GM-CSF at concentrations of 0.5–0.8 ug/kg/day transiently increased leukocyte, neutrophil, eosinophil and monocyte counts in AIDS patients with no significant rise in platelet counts or change in reticulocyte and lymphocyte counts (Miles, S. 1992 AIDS Res. Hum. Retroviruses 8:1073–1080). Subcutaneous injections of 0.25–4.0 ug/kg/day improved leukocyte counts with no improvement in hemoglobin or platelet counts. However, the side effects included increased HIV replication, increased levels of P24 antigen, chills, nausea, myalgia and flu-like symptoms (Poli, G. et al. 1991 J. Fxp. Med. 173:589–597; Scadden, D.T. 1990 Hematopoietic Growth Factors in Trans. Med., Wiley-Liss Inc., New York, pp. 163–176). GM-CSF also occasionally caused thrombocytopenia. Granulocyte colony stimulating factor (G-CSF) has been effective in correcting neutropenia with some minor increases in lymphocyte counts. Additionally, hemoglobin and reticulocytes increased in numbers in patients given G-CSF alone or in combination with erythropoietin. However, resumption of treatment with AZT after use of these growth factors led to severe anemia. Pharmacological doses of growth factors often have harsh side effects. Homeopathy, which dates back to the nineteenth century, is founded on the principles of pharmacology. One of the earliest laws of pharmacology, representing the homeopathic effect, is known as the Arndt-Schultz law. Formulated by Arndt in 1888 and restated by Hueppe, the law states: for every substance, small doses stimulate, moderate doses inhibit, large doses kill. Allopathic medicine, with its emphasis on moderate drug doses, works to inhibit undesired physical symptoms and to kill undesired pathogens. Homeopathic medicine begins with small doses and moves towards higher and higher dilutions to stimulate the body's own natural electromagnetic forces.

Homeopathic and allopathic principles can be represented on the same sinusoidal curve (shown in FIG. 1). There are several harmonic concentrations over a log scale of dilutions that give the same desired effect. Oscillatory data demonstrating the stimulating and inhibiting effect of log dilutions of anti-IgE antisera which caused human basophil degranulation have been generated and reproduced (Davenas, E., Beauvais, F. et al. *Nature* 333:816–818, 1988; Beneviste, J., Davenas, E. et al. *C.R. Acad. Sci. Paris* 312, series II, pp. 461–466, 1991). Control studies using dilutions of antihuman IgG antisera or simply distilled water did not produce this same effect. One of the basic tenets of homeopathic medicine is that a cure for a disease can be evoked by using a high dilution medicine that resembles but is different from the cause of the disease. Homeopathy is widely accepted as a useful therapeutic throughout Europe, the British Commonwealth countries and India, and has been demonstrated to have characteristic and reproducible effects. A critical review of more than 100 controlled and/or clinical studies of homeopathy determined that patients received positive healing benefits from homeopathy beyond the placebo effect (Kleijnen, J. et al. 1991 Brit. Med. J. 302:316–323).

Many homeopathic medicines are used at concentrations of micrograms ($10^{-6}$ M) and nanograms ($10^{-2}$ M); however, other homeopathic dilutions exceed Avogadro's number ($6.023 \times 10^{-23}$). When homeopathic compounds are diluted 1:10, with repeated succusions (similar to vortexing) and repetitively diluted by this procedure at least 24 times a potency is achieved ($10^{-24}$) that is so highly dilute that the probability of a single molecule of the original substance remaining in the volume used is less than $1 \times 10^{-10}$. Homeopathic practitioners believe that the potency of a compound increases with increasing dilutions. The standard homeopathic dosage is 10–15 drops of a $10^{-12}$ molar, or 6 C, solution administered two to three times per day. A $10^{-60}$ molar or 30 C may be given only one time per day. A $10^{-400}$ molar or 200 C may be given only one time per month or year. A 6 C dilution approximates 1 ng/ml, which is used in cell culture but would be considered a lower than physiological dose when administered to a patient either orally or by injection.

Highly dilute homeopathic medicines have been effective in treating some viruses in vivo. Homeopathic dilutions of $1 \times 10^{-200}$ to $1 \times 10^{-1000}$ of typhoidinum, hydrophobinum, tuberculinum, nux vomica and malandrinum 100% inhibited pock-like lesions caused by a chicken embryo DNA virus on the chorio-allantoic membrane compared to controls (Singh, L. M. and Gupta, G. 1985 Brit. Homeopathy 74:168–174). Other homeopathic medicines, the same medicines at different homeopathic concentrations or control phosphate buffered solution (PBS), had lesser to no effect.

One of the advantages of homeopathic medicine in the treatment of chronic viral infections is apparent in terms of viral mutation. One of the problems associated with the use of allopathic pharmaceuticals is the drug resistance that develops as viruses mutate during frequent cycles of replication. For example, detailed kinetic studies on HIV viral load with antiviral therapy have demonstrated that the half-life of HIV in plasma is every two days. In other words, 30% of the viral load measured on any given day was produced in the last 24 hours. HIV is the most rapidly replicating and mutating virus known to man. Homeopathic therapeutics are superior to allopathic therapeutics in the treatment of chronic viral infections since homeopathic medicines, such as high dilutions of growth factors, have no molecules that viruses, such as HIV, can mutate against. Homeopathic dilutions of growth factors probably activate signal transduction pathways without using signaling molecules.

While the exact mechanism of action of homeopathic medicines is unknown, magnetic resonance image measurements on serial dilutions of substances indicate that the hydroxyl (OH) groups in the solvent of solutions continue to change as dilutions become successively higher (Sacks, A. D. 1983 J. Holistic Med. 5:175–176; Smith, R. and Boericke, G. 1968 J. Am. Inst. Homeopathy 61:197–212; Smith, R. and Boericke, G. 1966 J. Am. Inst. Homeopathy 59:263–279). It is clear that the specific effects of homeopathics are of a non-molecular origin, yet provide potent biological information that is clinically effective. It has been postulated that highly dilute compounds transfer biological activity to cells by electromagnetic fields (Benveniste, J. 1993 Frontier Perspectives 3:13–15).

Experiments in several laboratories have provided evidence that a specific biological activity can be initiated and/or modulated by highly dilute substances that contain hardly a molecule. An argument against a molecular basis for the activity is that heating dilutions to 70° F. for 30 minutes or exposure to magnetic field strengths of 50 Hz, 150 gauss, for 15 minutes totally suppresses these effects. Del Giudice et al. have hypothesized that interactions between the electric dipoles of water and the radiation fields of a charged molecule generate a permanent polarization of water which becomes coherent and has the ability to transmit specific information to cell receptors, somewhat like a laser (Del Giudice, E., Preparata, G., Vitiello, G. 1988, Phys. Rev. Lett. 61:1085–1088).

The cell surface membrane is the interface between electromagnetic waves and biological activity of cells. Cell membranes maintain a carefully controlled surface potential that is transiently altered by electromagnetic fields, viral attachment, and binding of neurotransmitters, hormones and growth factors to their receptors. Liboff suggests that specific ionic currents are induced by Faraday's Law which affects the cell surface receptors and ion channels. (A.R. Liboff 1985, J. Biol. Physics 13:99–102.) In specific regions of the cell, such as the location of ionic channels and cell receptors, there may be reduced wave scattering. Ionic species or charged side chains on cell receptors, will follow a resonating circular or helical well-defined orbit under the influence of electromagnetic signals. Liboff points out that channelized ions are constrained to move along helical paths. Similarly, receptor molecules are constrained within the lipid bilayer and will resonate with specific frequencies given proper periodic stimulus. Any movement or conformational changes of growth factor receptors will induce signal transduction processes. The well-ordered water molecules that participate in intermolecular hydrogen bonding networks are present in the interface regions between growth factors and their receptors, however they are not significant for protein binding (Clackson, T. and Wells, J. A., 1995 Science 267:383–386). Ordered water molecules are observed in several other protein-protein interfaces and can be present in both the bound and unbound states. For example, water molecules which fill gaps between imperfectly packed regions of human growth hormone receptors'extracellular domain in the ligand/receptor bound state are fully available for electromagnetic activation in the unbound state. The integration of these separate schools of thought suggests that high dilutions of substances create changes in electromagnetic forces inducing resonance in cell surface signal proteins thus transferring biological activity through cell receptors or ionic channels and initiating signal transduction processes.

Bioelectromagnetics underlies biochemical reactions. The science of bioelectromagnetics studies the interactions of electromagnetic fields in living systems (Rubik, R. and Flower, R.G. 1994 Electromagnetic applications in medicine, *Expanding Medical Horizons: Report to NIH on the Status of Alternative Medicine*, U.S. Govt. Printing office, Washington, D.C.; Tenforde, T. S. and Kaune, W. T. 1987 Health Physics 53:585–606). Electrical stimulation of cells temporally changes the cell's membrane potential and evokes consequential changes of RNA, DNA and protein synthesis (Bourguignon, G. J. and Bourguignon, L. Y. 1987 FASEB J. 1:398–402; Rodan, G. A. et al. 1978 Science 190:690–692).

Several studies on the effects of administering electromagnetic signals have been published. For example, Thomas et al. demonstrated behavioral changes in rats following administration of a cyclotron electromagnetic field which resonates for the signal for unhydrated lithium ions (Thomas J. R. et al. 1986 Bioelectromagnetics 7:349–357). Researchers also report inhibition of tumor growth after administration of human interferon alpha (IFN-($\alpha$) plus DC current (Sersa, G. and Miklavcic, D. 1990 Molecular Biotherapy 2:165–168). Electrical stimulation of epidermal fibroblast cells has been shown to regulate both transforming growth factor-beta and insulin receptors (Falanga, V., Bourguignon G. J., Bourguignon, L. Y. 1987 J. Invest. Dermatol. 88:488; Bourguignon, G. J., Jy, W., Bourguignon, L. Y. 1989 J. Cell. Physiol. 140:379–385). The cell membrane, and in fact the whole body, respond to electrical and magnetic stimuli and are thus receptive to communications beyond the level of biochemical and molecular mechanisms.

Hormones and polypeptide growth factors are important regulatory substances that are involved in the regulation of cell growth and differentiation, as well as in the control of specific metabolic processes. Hormones are synthesized in the endocrine glands and are secreted into extracellular body fluids. Hormones are transported to hormone-responsive cells, where they bind to a hormone receptor, and the hormone-receptor complex regulates and modulates differentiated functions. Polypeptide growth factors are produced and secreted by cells from a variety of tissues, and are generally involved in paracrine and autocrine responses. Growth factors are involved in cell survival and play a crucial role in the control mechanisms governing the development and maintenance of organs and tissues. In addition to their growth promoting and differentiation inducing effects, growth factors are also involved in important physiological processes such as inflammation, immune reactions, and tissue repair.

Certain hormones have been prepared and used homeopathically. Adrenalinum, or ephinephrine, a sympathomimetic hormone produced by the medulla of the adrenal glands, thyroidinum, a preparation from the thyroid gland, and adrenocorticotrophin, or cortocotropin, a polypeptide hormone that increases the rate of secretion of the adrenal corticosteroids, are included in the official Homeopathic Monographs from the General Pharmacy of the Homeopathic Pharmacoepia of the United States. Insulin, an active molecule found in the pancreas which affects sugar metabolism, is listed in Boericke's Materia Medica, and is noted for its applicability for skin conditions. Parathyroid hormone, an extract from the parathyroid gland; thyreotrophic hormone, an extract from the anterior lobe of the pituitary gland; Corticotrophin, also extracted from the anterior lobe of the pituitary gland; cortisone and corticoids, which are steroid hormones; and folliculinum, a hormone secreted by the ovaries, are listed in the Materia Medica of New Homeopathic Remedies by Julian. The clinical symptomatology for parathyroid hormone includes general weakness, depression, asthenia, hypotonia, fatigue, pallor and emaciation. The clinical symptomatology for thyreotrophic hormone include various conditions of the mind, digestive system, circulatory system, respiratory system, sense organs, and urinary and genital organs. The clinical symptomatology for corticotrophin include various psychological and nervous conditions. The symptomatology of cortisone and corticoids includes various psychological, nervous, endocrine and digestive system conditions. The clinical symptomatology for folliculinum includes various conditions of the mind, digestive system and circulatory system.

Few effective treatments are available for disorders such as chronic viral infections, cancer, and diabetes. Insulin-dependent diabetes, while regulated by insulin, still has many complications. Despite more than ten years of aggressive research, both conventional and naturopathic, no definitive treatment exists for HIV infection or acquired immunodeficiency syndrome (AIDS). There thus continues to be a need in the art for effective treatments for chronic viral infections, cancer and diabetes.

Similarly, few effective treatments are available for conditions such as inflammation, joint and muscle pain, muscle weakness, fatigue, sinus and nasal congestion, breathing difficulties, poor digestion, neuropathy, headaches, reduced mental acuity, poor memory, skin conditions, poor fitness, weight imbalances, and a variety of psychological conditions, such as mood swings, depression, anxiety, confusion and anger. There continues to be a need in the art for effective treatments for such conditions that are cost effective and conveniently administered.

SUMMARY OF THE INVENTION

It is an object of the present invention to provide an effective treatment for disorders including chronic viral infections, cancer, diabetes and depression which will slow the progression of disease and/or relieve disease symptoms. Another objective of the present invention is to provide effective treatments for a variety of conditions, including inflammation, joint and muscle pain, muscle weakness, fatigue, sinus and nasal congestion, breathing difficulties, poor digestion, neuropathy, headaches, reduced mental acuity, poor memory, skin conditions, poor fitness, weight imbalances, and a variety of psychological conditions, such as mood swings, depression, anxiety, confusion and anger. Yet another objective of the present invention is to provide such treatments for such disorders and conditions that do not produce undesirable side effects and that can be provided to a large patient population at a reasonable cost and via convenient delivery systems.

These and other objectives may be achieved by administering homeopathic preparations of growth factors. Homeopathic preparations of growth factors may be administered orally, topically, using eye drops or nasal sprays, transdermally, by injection, intravenously, or using other delivery modalities.

It is believed that it is the electromagnetic properties of the homeopathic preparations of growth factors which exert the beneficial effects observed in a variety of diseases, disorders and conditions. The electromagnetic properties of homeopathic preparations of growth factors of the present invention may be elucidated and characterized by techniques that are known in the art, such as nuclear magnetic resonance imaging, each preparation having an identifiable profile. Other techniques for identifying profiles for electromagnetic properties of homeopathic preparations of growth factors are also known the art. Materials having the same or similar electromagnetic profiles as homeopathic dilutions of growth factors are also encompassed in the preparations of the present invention. Electromagnetic signals, such as radio frequency signals, corresponding to homeopathic dilutions of growth factors, may also be administered to patients to produce beneficial effects.

Growth factors are cell signaling polypeptides which modulate cell proliferation and differentiation by binding to specific cell membrane receptors. Binding of growth factors to cell membrane receptors initiates a cascade of intracellular events that affect gene transcription and expression within the cell. Growth factors range in size from 3,500 to 250,000 daltons and, unlike hormones, generally act on nearby cells via autocrine and paracrine mechanisms. They may also act as second messengers for hormone signals.

Proteins, such as growth factors, may evolve from a common ancestor to the point where they no longer share amino acid sequence similarity. However their relatedness may be evident from a structural comparison. Polypeptide growth factors, a diverse group of regulatory agents, have similar protomeric structures. McDonald and Hendrickson have classified growth factors into six superfamilies based on homology of characteristic three dimensional structures (1993 Cell 73:421–424). X-Ray crystallographic and NMR studies have shown that growth factors contain relatively few recurring structural folds despite their diversity. When structural folding is considered, several proteins previously regarded as hormones, such as insulin and growth hormone, are subsumed into the definition of growth factors. Cytokines and growth factors are very similar in both size and function. The term "growth factor," as used herein, therefore encompasses cytokines and some hormones, as well as the traditional growth factors.

A specific growth factor may have many cell sources and can use different signal transduction pathways at different times and with different cells. Growth factors are involved in complex feedback loops between the immune, nervous and endocrine systems.

The homeopathic preparations of growth factors of the present invention are preferably of a concentration of less than about $10^{-6}$ molar, and preferably between about $10^{-6}$ molar and about $10^{-100,000}$ molar. Some of the homeopathic dilutions may thus contain few or no molecules of growth factors. Preparations of growth factors according to the present invention may contain multiple potencies and/or multiple growth factors. Preparations comprising 30 C and 1M $PDGF_{BB}$ and 30 C and 1M $TGF_{\beta 1}$ have, for example, been demonstrated to be produce positive effects for a variety of conditions. Homeopathic dilutions of growth factors are preferably administered orally, in liquid or solid form, such as pellets or tablets. Oral administration is convenient and effective. Alternative delivery systems, such as eye drops, nasal sprays, and topical preparations also provide convenient and effective delivery of the homeopathic preparations of growth factors. The preparations may also be delivered transdermally, by injection, such as at acupuncture, acupressure or skin conductance points, or they may be delivered intravenously.

Growth factors which may be utilized in the present invention include granulocyte macrophage-colony stimulating factor (GM-CSF), granulocyte-colony stimulating factor (G-CSF), macrophage-colony stimulating factor (M-CSF), tumor necrosis factors (TNFα and TNFβ), transforming growth factors (TGFα and TGFβ), epidermal growth factors (EGF), stem cell factor (SCF), platelet-derived growth factors (PDGF), platelet-derived endothelial cell growth factor, nerve growth factor (NGF), fibroblast growth factors (FGF), insulin-like growth factors (IGF-I and IGF-II), growth hormone, interleukins 1 to 13 (IL-1 to IL-13), interferons α, β and γ (IFN-α, IFN-β and IFN-γ), brain-derived neurotrophic factor, neurotrophins 3 and 4, hepatocyte growth factor, erythropoietin, EGF-like mitogens, TGF-like growth factors, PDGF-like growth factors, melanocyte growth factor, mammary-derived growth factor 1, prostate growth factors, cartilage-derived growth factor, chondrocyte growth factor, bone-derived growth factor, osteosarcoma-derived growth factor, glial growth-promoting factor, colostrum basic growth factor, endothelial cell growth factor, tumor angiogenesis factor, hematopoietic stem cell growth factor, B-cell stimulating factor 2, B-cell differentiation factor, leukemia-derived growth factor, myelomonocytic growth factor, macrophage-derived growth factor, macrophage-activating factor, erythroid-potentiating activity, keratinocyte growth factor, ciliary neurotrophic growth factor, Schwann cell-derived growth factor, vaccinia virus growth factor, bombyxin, neu differentiation factor, v-Sis, glia) growth factor/acetylcholine receptor-inducing activity, transferrin, bombesin and bombesin-like peptides, angiotensin II, endothelin, atrial natriuretic factor (ANF) and ANF-like peptides, vasoactive intestinal peptide, Bradykinin, and other polypeptides that belong to their structural superfamilies.

Especially preferred growth factor preparations according to the present invention include one or more of the following growth factors: $IGF_1$, $PDGF_{BB}$, $TGF_{\beta 1}$, GM-CSF, or NGF. Growth factors for use in such preparations may be isolated from natural sources or produced using recombinant or other polypeptide synthesis technology. Molecules including one or more active cell signaling sites of the growth factors enumerated above are also encompassed within the term "growth factor(s)" as it is used in this specification and the appended claims.

The human body, when it is functioning in a balanced state, is well equipped to defend itself from health hazards and maintain a healthy balance, or homeostasis. When functioning in a balanced state, the body effectively compensates for stress factors, such as infectious agents, fatigue, nutritional deficiencies, and emotional stress. Under healthy, homeostatic conditions, the body heals itself when trauma or stress occurs. With continued stress or trauma, however, the body works harder to adapt and depletes its energy reserves. Chronic depletion of reserves produces slower response times to stress factors, and leads to homeostatic imbalances which render the body more susceptible to various diseases and disorders through ineffective immune, nervous and metabolic system responses to growth factors.

Growth factors facilitate cell communication and maintain healthy homeostasis. Growth factors have significant effects on DNA, RNA, protein synthesis and cell division and affect the cell cycle through positive and negative feedback processes, as well as controlling various cell functions. Homeopathic preparations of growth factors according to the present invention have been demonstrated as effective treatments for a wide variety of diseases, disorders, and conditions, including chronic viral infections, cancer, diabetes, depression, inflammation, joint and muscle pain, muscle weakness, fatigue, sinus and nasal congestion, breathing difficulties, poor digestion, neuropathy, headaches, reduced mental acuity, poor memory, skin conditions, poor fitness, weight imbalances, and a variety of psychological conditions, such as mood swings, depression, anxiety, confusion and anger. Homeopathic dilutions of growth factors have also been demonstrated to increase lean muscle mass and reduce body fat and improve eyesight. It is believed that the tendency of growth factors to promote homeostasis accounts for the wide variety of diseases, disorders and conditions that are effectively treated by homeopathic preparations of growth factors according to the present invention.

Chronic viral infections that may be treated using the homeopathic dilutions of growth factors of the present invention include fIV, EBV, herpes simplex, papilloma, cytomegalovirus, Coxsackie B, hauta virus, human herpes 6 virus and hepatitis viral infections. Other disorders which may be effectively treated using the methods of the present invention include cancers such as leukemia and adenocarcinoma.

In other aspects, the present invention relates to the treatment of such disorders as depression, diabetes and muscle-wasting. Depression is a major clinical illness in the United States, affecting 8 to 20 million people at any given time. Clinical depression is defined as a period of at least two weeks during which there is either depressed mood or the loss of interest or pleasure in nearly all activities combined with at least four additional symptoms drawn from a list that includes changes in appetite or weight, sleep and psychomotor activity; decreased energy; feelings of worthlessness or guilt; difficulty thinking, concentrating or making decisions; or recurrent thoughts of death or suicidal ideation, plans or attempts.

In other aspects, the present invention relates to treatment of various conditions representing a homeostatic imbalance, including inflammation, joint and muscle pain, muscle weakness, fatigue, sinus and nasal congestion, breathing difficulties, poor digestion, neuropathy, headaches, reduced mental acuity, poor memory, skin conditions, poor fitness, weight imbalances, and a variety of psychological conditions, such as mood swings, depression, anxiety, confusion and anger using homeopathic preparations of growth factors. Yet other aspects of the present invention relate to increasing lean muscle mass, reducing body fat and improving eyesight using homeopathic preparations of growth factors.

DESCRIPTION OF THE FIGURES

FIGS. 8A and C show the absolute changes. FIGS. 8B and D show percentage changes.

DETAILED DESCRIPTION

Figure 1:
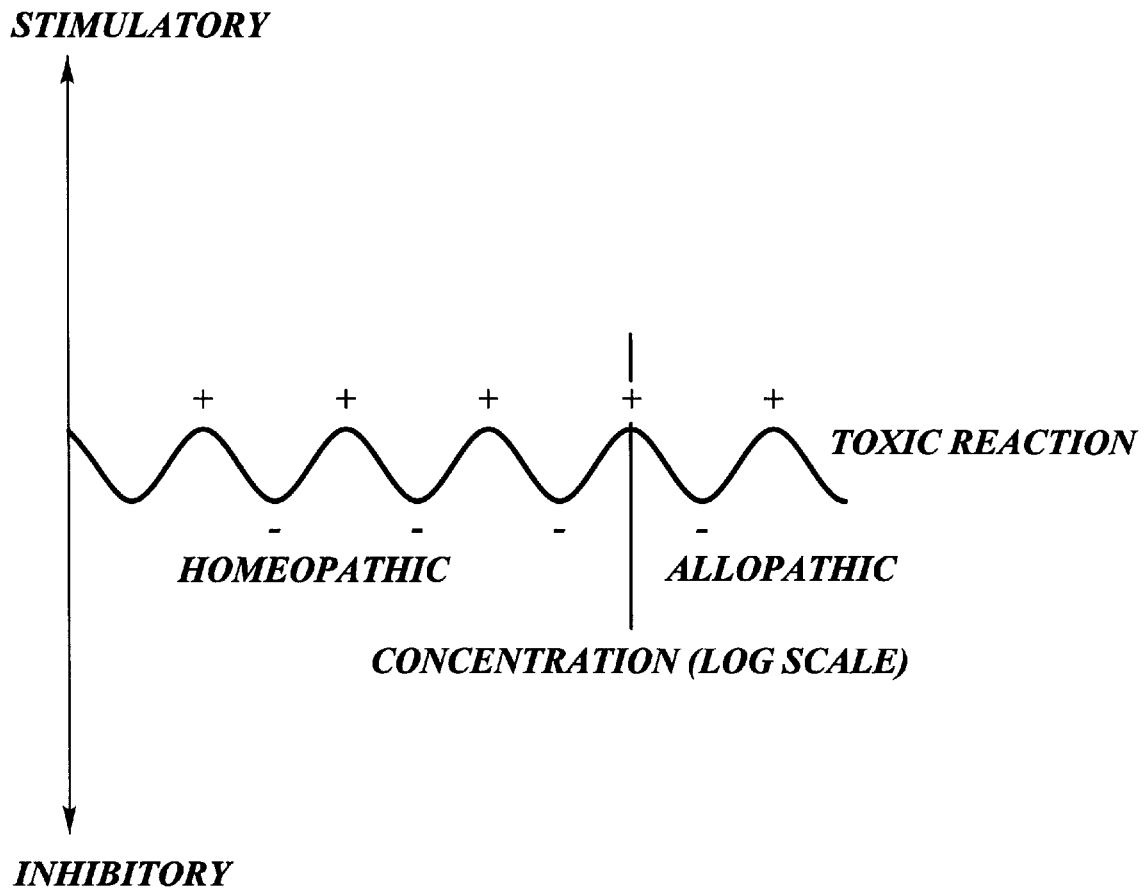
FIG. 1 is a sinusoidal curve demonstrating the stimulating and inhibiting effects of homeopathic and allopathic medicines.

The homeopathic preparations of the present invention typically comprise between $1 \times 10^{-6}$ and $1 \times 10^{-100,000}$ molar concentrations of growth factor in a pharmaceutically acceptable diluent. Various diluents may be used, depending on the appropriate delivery system. Appropriate diluents for the following delivery systems are well known: oral administration in liquid or solid form; intravenous administration; injection; eye drops; nasal sprays; and topical administration. One or more potencies of a specified growth factor and/or one or more growth factors may be combined in a preparation. The preferred homeopathic diluent for oral administration is a solution of purified water, glycerin, citric acid and a preservative such as sodium benzoate. Other diluents for oral delivery, including various alcohol-containing solutions, are known in the art and may be employed in the present invention to increase solubility and stability of growth factors. The homeopathic dilutions of the present invention are preferably administered orally, but may also be prepared in topical formulations for application to the skin, administered transdermally, administered in the form of eye drops, injected into acupuncture or skin conductance points, or administered intravenously. In a preferred embodiment, homeopathic dilutions of growth factors are administered by means of liquids or tablets which retain the memory of the homeopathic dilution. The tablets are made from a suitable organic material, such as lactose (Botanical Labs., Bellingham, Wash.) by methods well known in homeopathy (see, for example, the United States Homeopathic Pharmacopeia). Alternative methods of administration may also be used, such as topical application. Example 1 describes the preliminary results of a double-blind placebo controlled clinical study evaluating the effects of administration of homeopathic dilutions of growth factors on lymphocyte counts in HIV patients using liquid dilutions. Example 8 describes treatment of a patient with insulin dependent diabetes with a homeopathic preparation of insulin-like growth factor (IGF-1) in solution. Example 10 illustrates the effects of oral administration of homeopathic preparations of growth factors in solution on depression levels in healthy patients diagnosed with clinical depression. Examples 11–19 demonstrate the effectiveness of oral administration of homeopathic preparations of growth factors in solution to improve various conditions that represent an imbalance in homeostasis.

Radio frequency signals corresponding to homeopathic dilutions of growth factors may be administered as illustrated by Examples 2–7 and 9, in which Example 2 describes a one time evaluation of homeopathic growth factor signals on HIV-positive patients; Example 3 demonstrates the effect of repeated administrations of homeopathic growth factor signals on two HIV-positive patients compared to a control patient who was not treated with radio frequency signals corresponding to homeopathic dilutions of growth factors; Example 4 shows a four-year longitudinal study of an HIV-positive patient treated with homeopathic growth factor signals; Example 5 describes the effects of administration of homeopathic growth factor signals on patients with Epstein-Barr viral infections (EBV); Example 6 describes the treatment of two cancer patients with signals corresponding to homeopathic growth factors; Example 7 demonstrates the effects of administration of homeopathic growth factor signals to a patient with chronic lymphocytic leukemia; and Example 9 demonstrates the effects of administration of homeopathic growth factor signals to two diabetic patients.

Figure 2A:
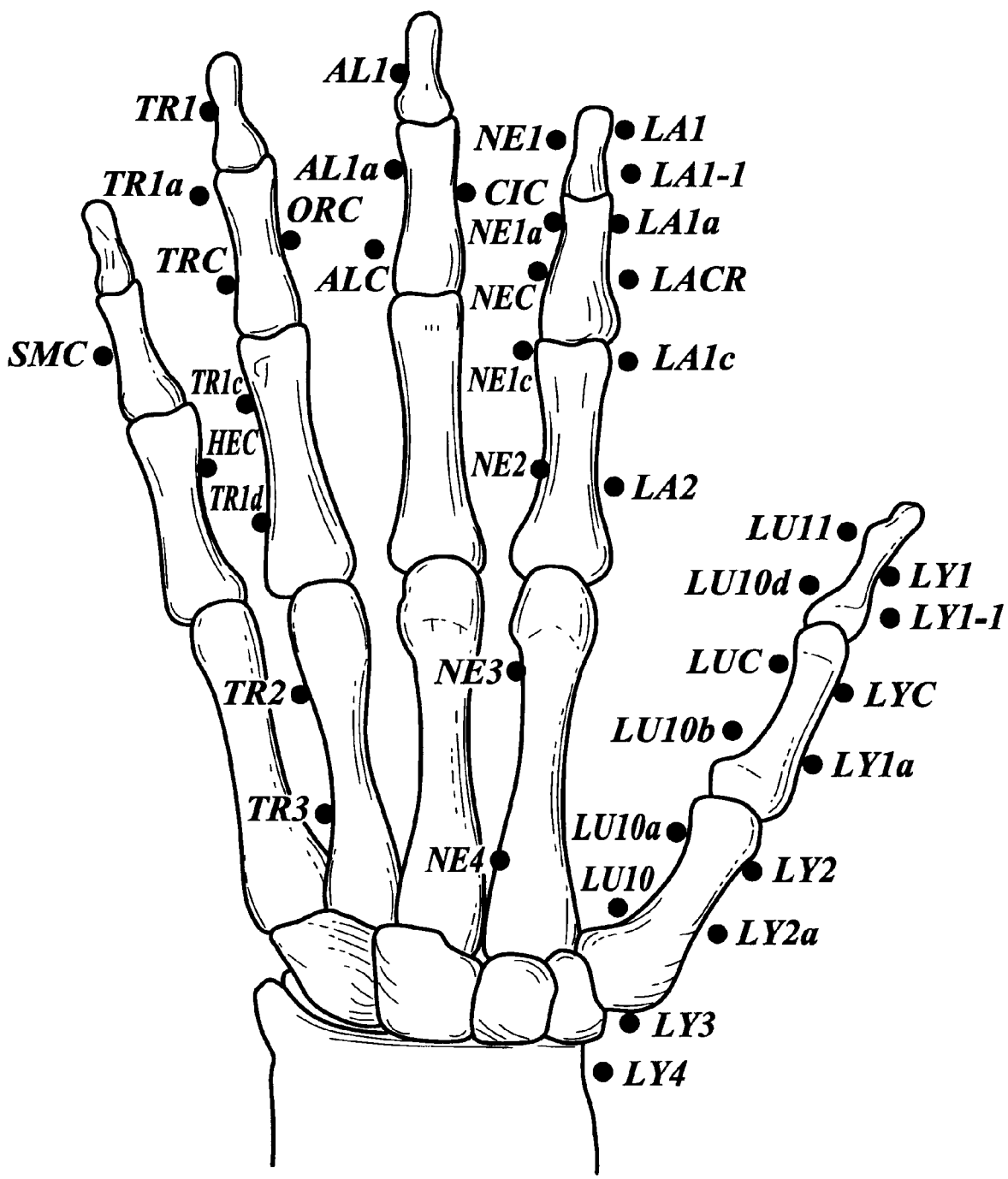
FIGS. 2A and B show electrical conductance points for the hand and foot as determined by Voll.
Figure 2B:
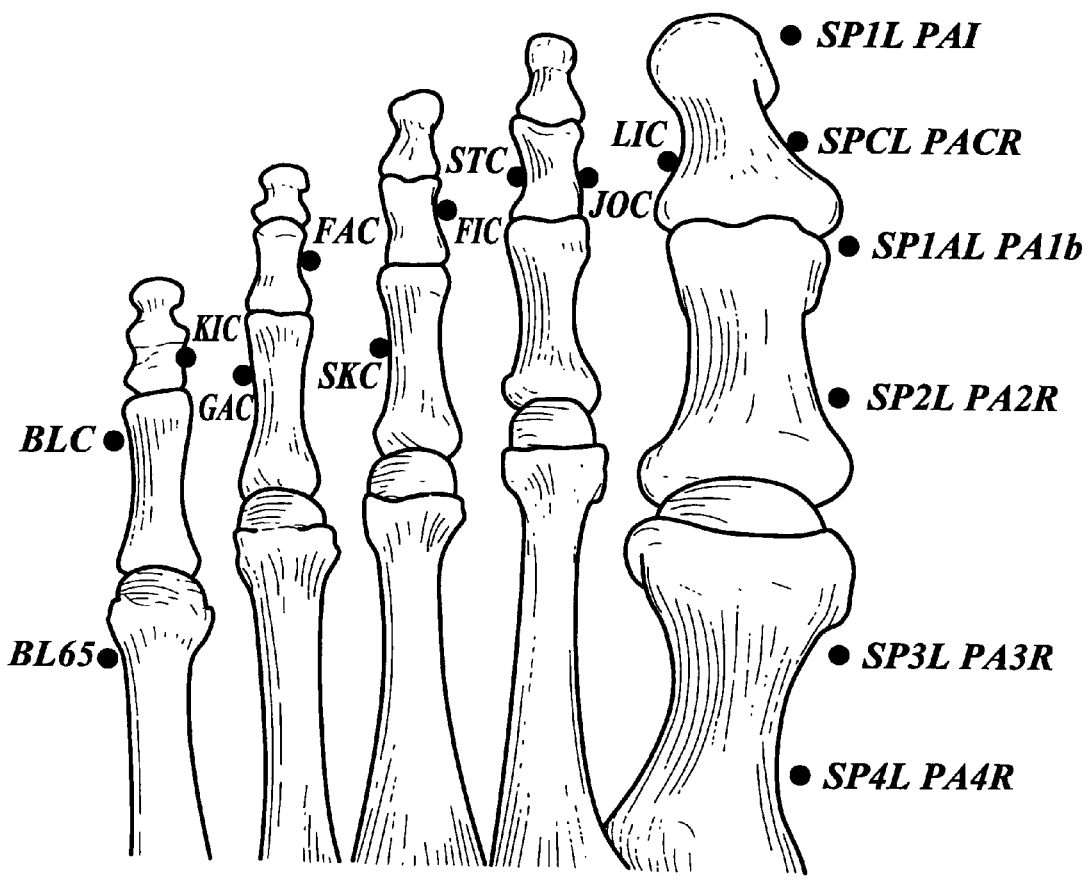

In Examples 2–7 and 9, patients were treated using the Life Information System TEN (LISTEN) (BioSource, Inc., Orem, Utah) which determines skin resistance or electrical conductance. The basic tenet behind the LISTEN system is that the points on the body normally referred to as "acupuncture points" have an optimal electrical resistance (100,000 ohms) in healthy subjects which changes during illness. Each acupuncture point is associated with a specific meridian, or line of electrical conductance, which in turn is associated with a particular organ or system of the body (Voll, R. 1977 *Topographic positions of the measurement points in electro-acupuncture*. 1st English edition, H. Schuldt translator, Medizinish Literarische Verlagsgesellschaft mbH, C. Beckers Buchdruckerei GmbH & Co. KG, M. Sc. Uelzen, Germany, vols 1–4+supplement). Furthermore, Voll showed that the electrical activity at each of these points is related to the functional status of the specific organ or system (See, for example, Am. J. Acupuncture 8:97–104, 1980). FIGS. 2A and 2B illustrate hand and foot conductance points as defined by Voll. Points coded LY are related to lymph tissue, LU to lung tissue, LA to large intestine, NE to the nervous system, TR to neuroendocrine points, SP to spleen and PA to the pancreas.

By determining the electrical resistance at different points on a patient, it is possible to determine which organs are affected by a disease. For example, Bergsmann and Woolley-Hart demonstrated significant differences in electrical conductances between human patients with and without liver disease at acupuncture points corresponding to the liver (1973, Am. J. Acupuncture 1:27–32). During the 1930–1940s Burr and associates at Yale published more than sixteen papers on bioelectric potential, or skin conductance, and its significance as an indicator of physiological states, such as cancer, in animal models (See, for example, Langman L. and Burr, H. S. (1949) Am. J. Obstet. Gyn. 57:274–281). In addition, a patient can be treated by providing a radio frequency electrical signal which restores electrical conductance at specific points to normal levels.

The LISTEN system is a modified computer-based system which, in addition to determining electrical resistance at specific conductance points, can be used to administer radio frequency signals corresponding to specific compounds, such as homeopathic dilutions of growth factors. These signals are generated by digital codes pre-programmed into the system by the manufacturer. The patient to be evaluated holds a source electrode, or brass bar, covered with wet gauze in one hand. The practitioner holds a second brass electrode, or probe, like a pen and touches a specific conductance point in the other hand or in a foot with the probe while firmly supporting the finger or toe.

Conductance points are said to be approximately 3 mm in diameter and located in the epidermal layer of the skin, often at the neck of the bones. In order to obtain the most accurate and reproducible measurement, the probe is placed at a 45° angle to the bone. Three tests are conducted per point in order to determine the reliability of the measurement.

Figure 3:
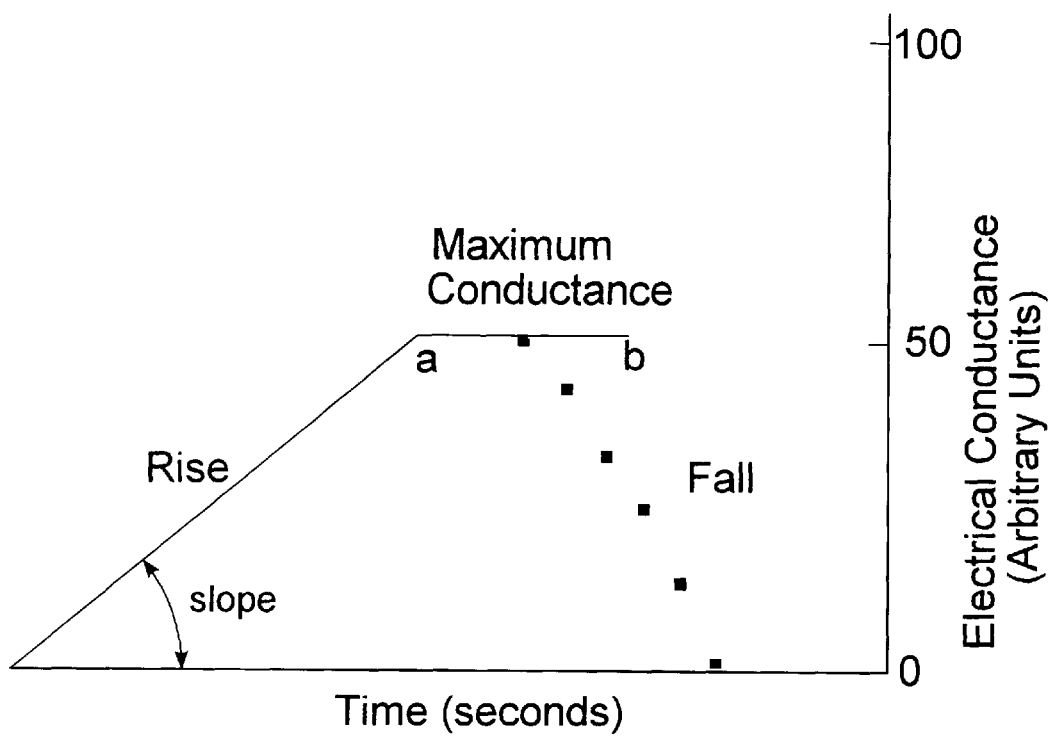
FIG. 3 shows the different outputs measured by the LISTEN system.

The LISTEN system determines three significant outputs: the rising slope; the maximal conductance; and the falling slope as shown in FIG. 3. The maximum is defined as the electrical conductance (ohms) produced at a patient's skin point in response to a maximal 5 volt stimulus. An internal clock calculates the time in seconds for the ohm meter to reach maximal conductance, and then during a constant one second period records the maximum and minimum conductance. The rising slope equals the maximum conductance divided by the seconds of time to reach maximum. The falling slope equals the maximum minus the minimum divided by seconds of time (in this case 1 second). Optimal resistance at an acupuncture skin point is 100,000 ohms (Zong-xiang 1981 Am. J. Acupuncture 9:203–216), scaled on this Y-axis at a value of 50 arbitrary units. Conductances in the range of 48–54 units at all skin conductance points on the hands and feet are thus indicative of optimal human vitality or state of health. Calibration of the LISTEN device with a resistor occurs every six months so that 50 units=100,000 ohms with 1% precision. Preliminary studies on 28 points in 15 'healthy' individuals determined that the mean maximum conductance was 50.3±0.58 units (SEM) with a rise of 20.1±0.57 units/sec.

The general protocol followed in Examples 2–7 and 9 is outlined below.

Baseline conductance measurements were obtained on the right side plus one left side point for the spleen meridian in order to discover which points varied in their maximum and minimum from the optimal range of 48–54 and which points varied in rise from 14±0.3 and fall from 1.25±0.3. The areas in the body most out of balance were thus determined. The point with the highest abnormal reading or the highest point in the area with the greatest numbers of imbalanced energy was selected. The Specific Listings category of the LISTEN system was blind scanned in order to determine which growth factor was most likely to balance the specific point in terms of maximum-minimum readings and rise and fall readings. A radio frequency signal corresponding to the selected growth factor was then administered to the patient for a period of one second to determine if it alone would balance the electrical conductance at the chosen point. All available growth factor signals were tested in this manner until it was determined which growth factor or combination of growth factors balanced all the points. If chronically low points could not be brought back into the normal range, a growth factor signal was selected which brought the conductance reading as close to normal as possible. In the following examples, all points were brought back into the normal range.

Some patients in Table VI were then challenged with radio frequency signals corresponding to a variety of viruses. Each virus signal was tested for its ability to raise the patient's normal reading. Readings above 75 were considered to be a positive test. A signal corresponding to both the selected growth factor and the virus that "stressed" the normal point was subsequently administered to determine whether the selected growth factor could balance the electrical conductance under "stress" conditions.

The LISTEN system may be employed to determine whether a therapeutic agent would be effective in returning one or more specific organs or tissues of the body to optimal vitality by administering a signal corresponding to the therapeutic agent to the skin conductance point related to that organ or tissue and determining whether the signal returns the conductance at that point to the optimal level. The LISTEN system can thus be used to screen multiple therapeutic agents for efficacy in treating a specific disorder.

EXAMPLE 1

Twenty-one HIV-positive patients were enrolled in a double-blind placebo controlled study to evaluate the therapeutic efficacy of oral administration of homeopathic dilutions of growth factors in raising lymphocyte counts in HIV seropositive (HIV+) patients. In order to qualify for the study, patients had to be over 18 years of age, have CD4 counts in the range of 180–550 cells/mm$^3$, fall within CDC classifications A1, A2, B1, B2, B3 and C2, and not be receiving any conventional HIV therapy, such as recombinant soluble CD4, nucleoside or non-nucleoside reverse transcriptase inhibitors, TAT antagonists, antisense oligonucleotides, ribozyme therapy, transdominant proteins, protease inhibitors, glucosidase inhibitors, adoptive immunotherapy or ribonucleotide reductase inhibitors, either during or three weeks prior to the commencement of the study. The patients were randomly assigned to either a placebo group or a treatment group, with 11 patients being enrolled in the treatment group and 10 in the placebo group.

Homeopathic dilutions of insulin-like growth factor (IGF$_1$), transforming growth factor (TGFβ1), BB-platelet-derived growth factor (BB-PDGF) and granulocyte macrophage-colony stimulating factor (GM-CSF) were prepared as follows. IGF$_1$, TGFβ1, and BB-PDGF (all from Genzyme, Boston, Mass.) were diluted to a $10^{-4}$ concentration, equivalent to a homeopathic potency of 3 C in either 1M acetic acid or 0.10% trifluoroacetic acid and 30% acetonitrile which was then evaporated off. GM-CSF (tradename Leukine, Immunex Corp., Seattle, Wash.) was diluted to a $10^{-4}$ concentration in sterile water. Serial dilutions of 1:100 were made according to the protocol described in the United States Homeopathic Pharmacopeia to provide potencies of 30 C ($10^{-60}$) for BB-PDGF and TGFβ1, 200 C ($10^{-400}$) for GM-CSF, and 1M ($10^{-2000}$) for IGF$_1$, BB-PDGF, and TGFβ1, including 0.5% bovine serum albumin (BSA) for stability. The final dilutions were prepared in a 20% glycerine base solution in water without alcohol.

Patients in the treatment group were orally administered 10 drops each of BB-PDGF (both 30 C and 1M dilutions), TGFβ1 (both 30 C and 1M dilutions), IGF$_1$ (1M dilution) and GM-CSF (200 C dilution) three times per day. All growth factor dilutions were administered at the same time. The dilutions of each growth factor were contained in a separate bottle, thus four bottles of homeopathic dilutions of growth factors or four bottles of placebo were given to each participant. Patients in the control group were administered dilutions of 20% glycerine alone, which tasted and appeared to be the same substance but contained no growth factor dilutions.

Figure 4A:
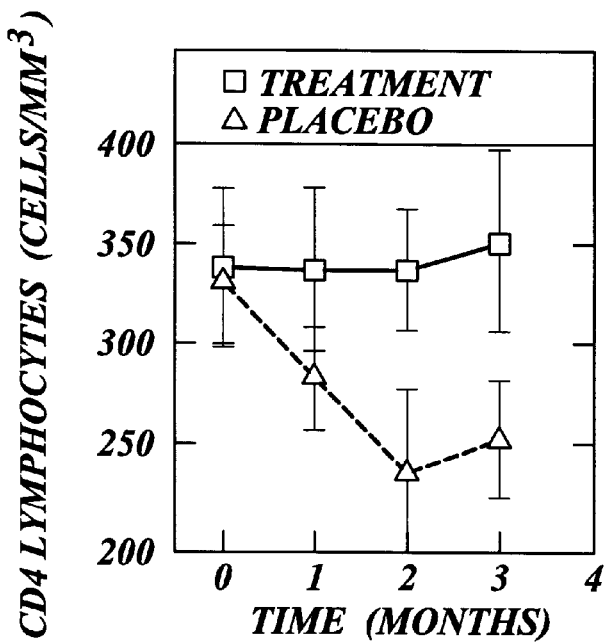
FIGS. 4A–C show the absolute counts of CD4, CD8 and CD2 lymphocytes in HIV-positive patients during three months of oral administration of homeopathic dilutions of growth factors compared to administration of placebo. All patients were taking natural medicines; none were taking antiretrovirals, human proteases, or other conventional HI1V treatments. No patients were taking steroidal therapy.

FIG. 4A shows the CD4 lymphocyte counts during three months of oral administration of homeopathic dilutions of growth factors compared to placebo treatment. The data show that CD4 lymphocyte counts in patients receiving homeopathic dilutions of growth factors remained stable or increased, while patients receiving placebo continued to lose CD4 lymphocyte counts. CD4 cells are generally associated with helper T lymphocyte cells.

The two groups started with approximately the same CD4 lymphocyte counts. Specifically, the treatment group had initial CD4 counts of 338±41 cells/mm$^3$ and the placebo group had initial CD4 counts of 335±39 cells/mm$^3$. Following two months of treatment, the CD4 lymphocyte counts for the two groups were significantly different, with the treatment group having a count of 340±32 cells/mm$^3$ and the placebo group having a CD4 count of 244±36 cells/mm$^3$. This represents a statistically significant difference of $P<0.05$ between the two groups after two months of treatment. After three months the treatment group had a CD4 lymphocyte count of 354±44 compared to the placebo group CD4 lymphocyte count of 257±36 cells. The fall in CD4 lymphocyte counts in the placebo group is similar to that found in other studies on the treatment of HIV+ patients using only natural medicine without growth factors.

Figure 4B:
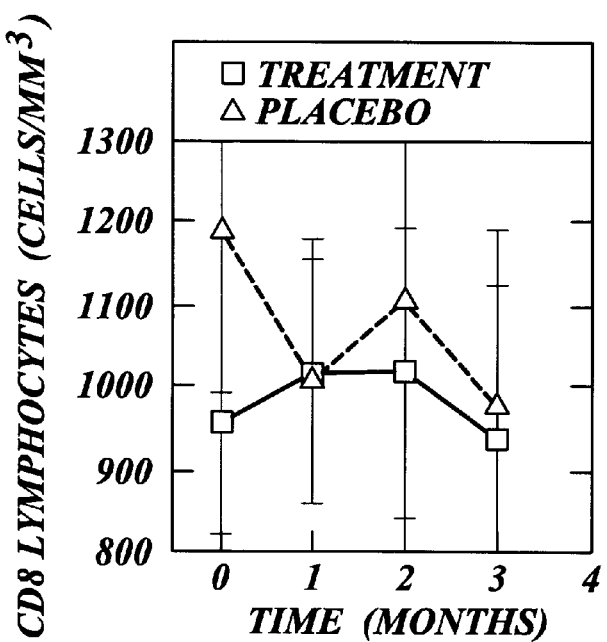
Figure 4C:
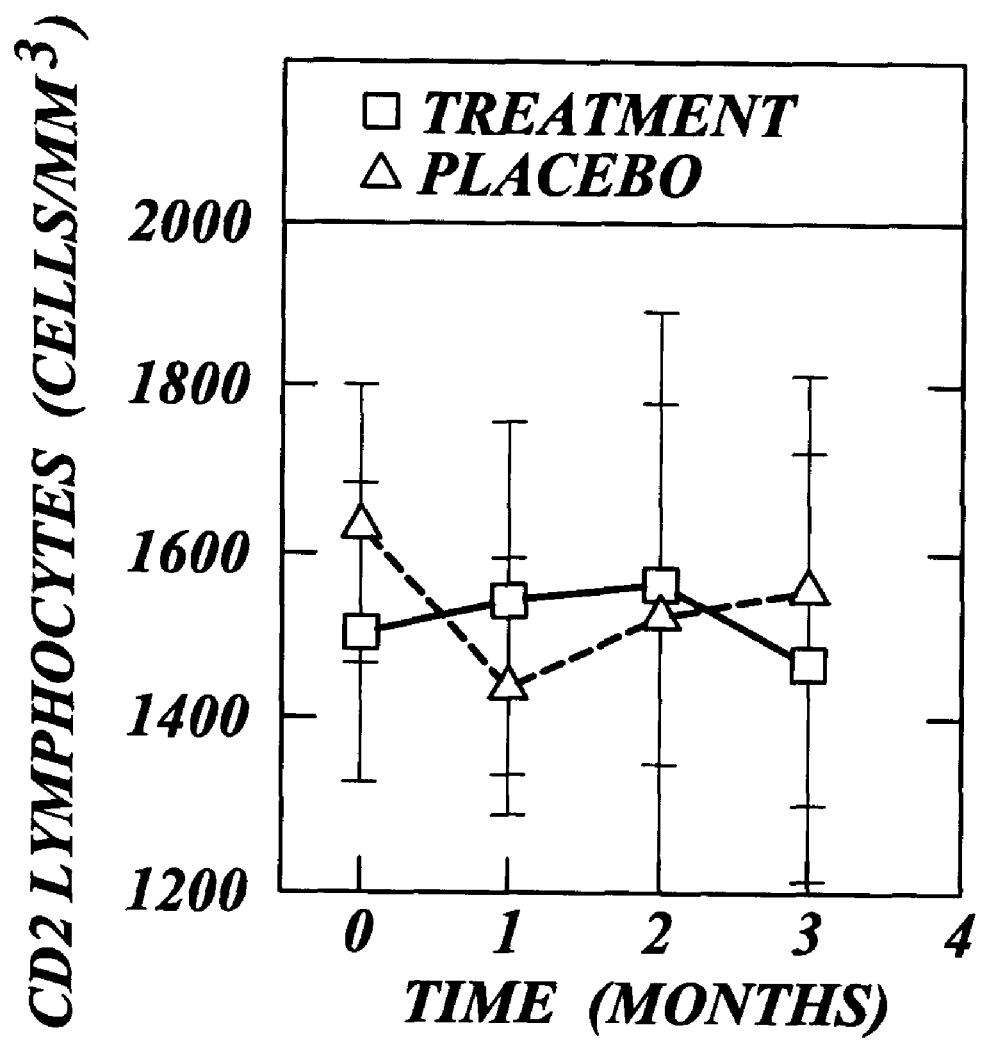

As shown in FIGS. 4B and 4C, no statistically significant changes were observed in CD8 and CD2 lymphocyte counts between the placebo and treatment group at the end of the three month study. CD8 cells are associated with suppressor T lymphocyte function and CD2 cells represent total T lymphocytes.

Figure 5:
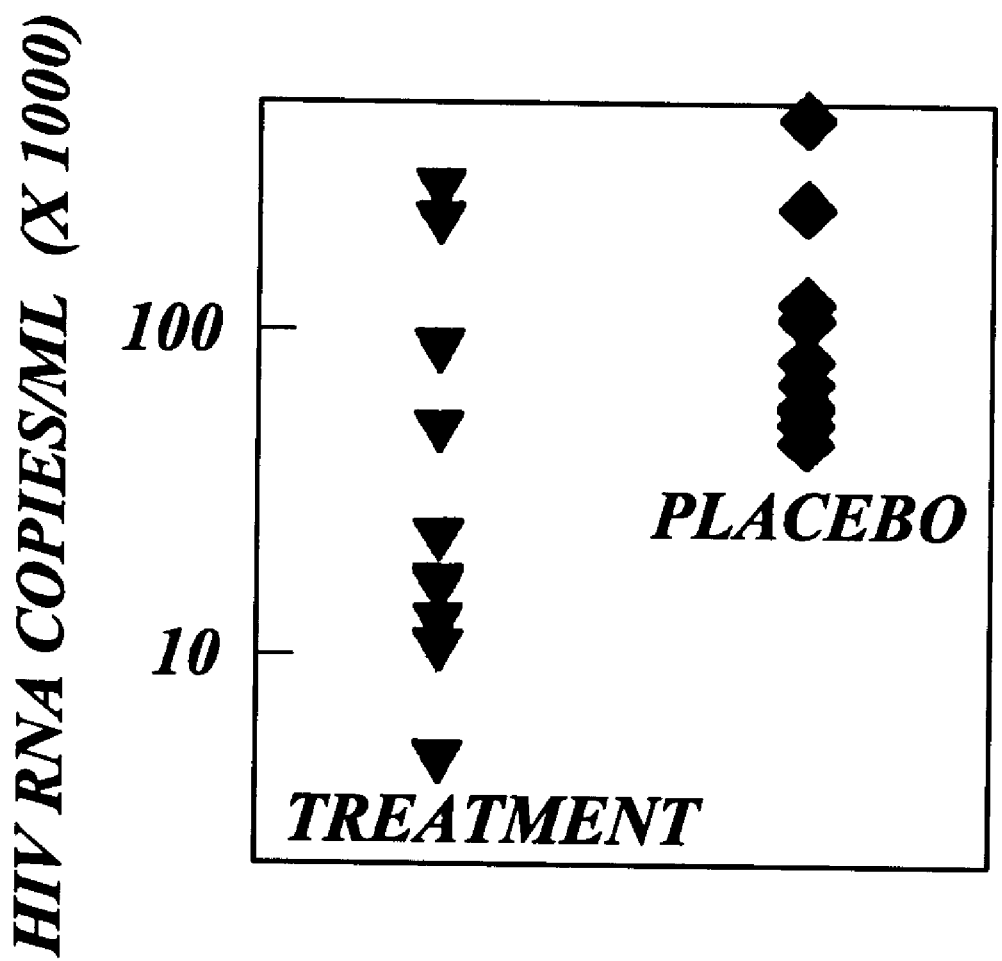
FIG. 5 shows a scattergram of the RNA count of HIV viral load in HIV-positive patients following three months of treatment with homeopathic dilutions of growth factors compared to administration of placebo.

Data on the RNA count of viral HIV load for the study participants (treatment group n=10, placebo group n=10) at the end of the three month study is presented as a scattergram in FIG. 5. As shown in FIG. 5, six patients in the treatment group had less than 50,000 HIV RNA copies/ml with a mean of 14,530±2,896 copies/ml compared to one patient with 46,360 copies/ml in the placebo group. This represents a three fold lower viral load in persons administered homeopathic dilutions of growth factor compared to placebo ($P<0.002$).

Figure 6A:
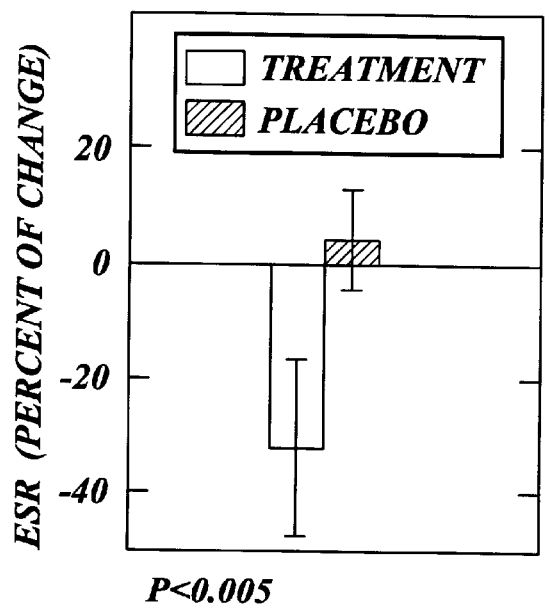
FIGS. 6A and B show the percentage change and absolute change, respectively, in erythrocyte sedimentation rates in HIV-positive patients following three months of oral administration of homeopathic dilutions of growth factors compared to placebo.
Figure 6B:
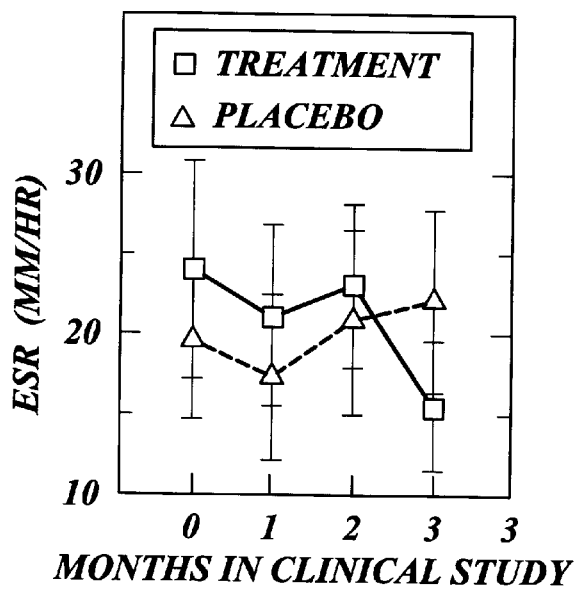

The difference in erythrocyte sedimentation rates (ESR) between the treatment and placebo groups was statistically significant at the end of the three month study as shown in FIG. 6. Both groups started with similar ESR values (24±6.8 mm/hr for the treatment groups compared to 19.6±4.9 mm/hr for the placebo group). Following three months of oral administration of homeopathic dilutions of growth factors, the ESR values for the treatment group had decreased to 15.5±4.03 mm/hr a decrease of 32.1±15.6%. In contrast, the placebo group ESR values increased to 22.1±5.7 mm/hr, an increase of 4.2±8.44% ($P<0.005$).

ESR values represent non-specific measures of inflammation and/or infection. ESR values rise steadily as HIV disease progresses. Research has shown that ESR values may be a useful addition to the CD4 count and beta 2-microglobulin in assessing the stage of HIV disease (Schwartlardes, B. et al. 1993 AIDS 7:813–21). Increased ESR values during disease progression in HIV-positive patients have been reported in a group of patients taking natural medicines (Standish, L. et al. 1992 J. Naturopathic Medicine 3:42–64). The difference in ESR values seen between the treatment and placebo groups in the present study is consistent with HIV-related disease progression in the placebo group. The treatment group continued to improve in health and lower their HIV-related symptoms. The decrease in ESR values demonstrates that homeopathic dilutions of growth factors positively and specifically affect lymphocytes and lower the chronic inflammatory reactions caused by HIV infection, or other chronic viral infections. There were no significant changes in hemoglobin or hematocrit in either group during the three month clinical study.

Figure 7:
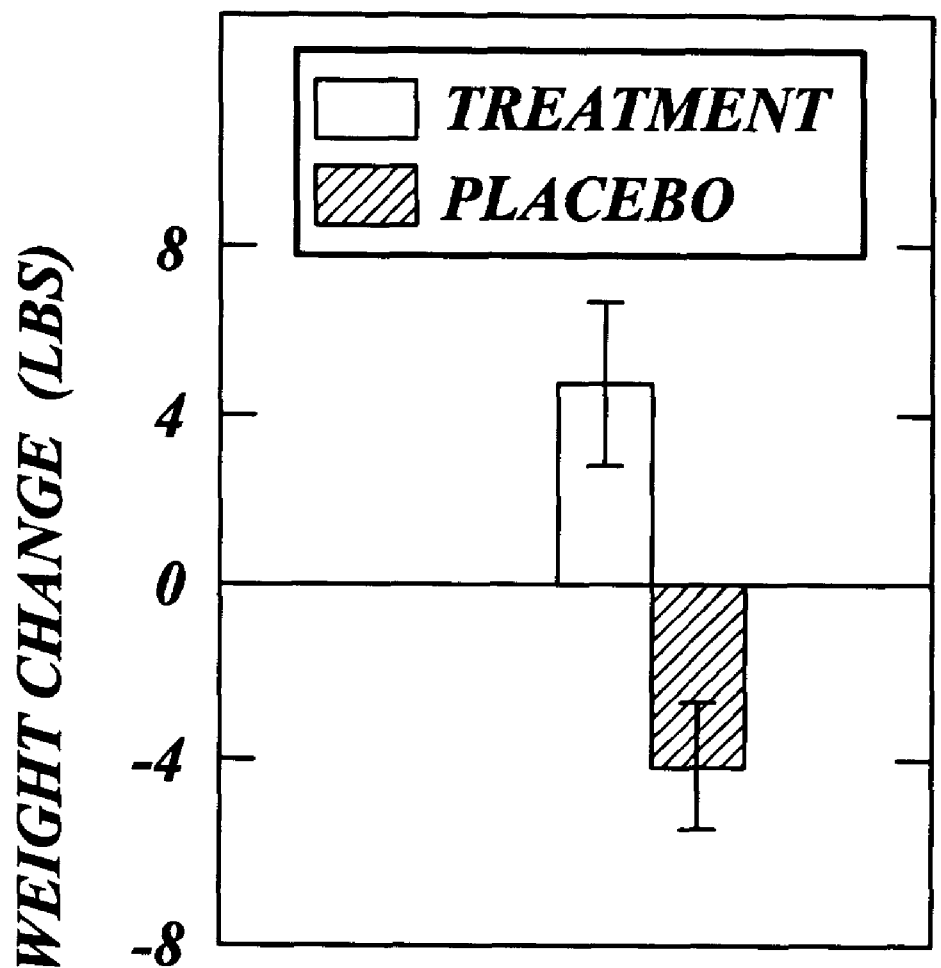
FIG. 7 shows the weight changes in HIV-positive patients following three months of treatment with homeopathic dilutions of growth factors compared to administration of placebo.
Figure 8A:
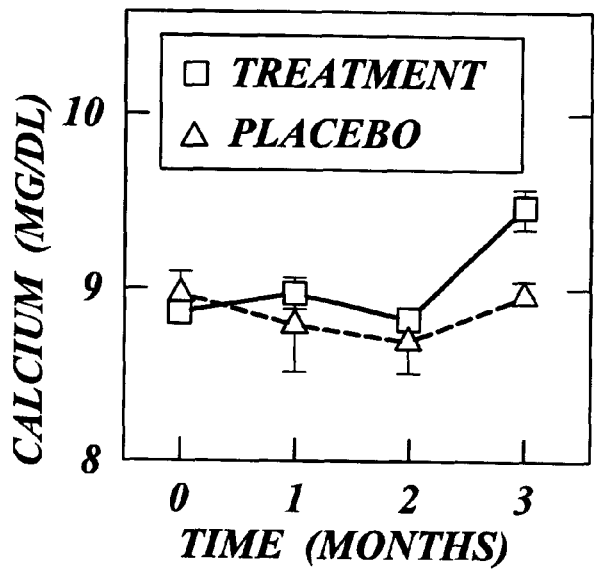
FIGS. 8A–D show the change in serum calcium and phosphorus levels in HIV-positive patients following three months of oral administration of homeopathic dilutions of growth factors compared to administration of placebo.
Figure 8B:
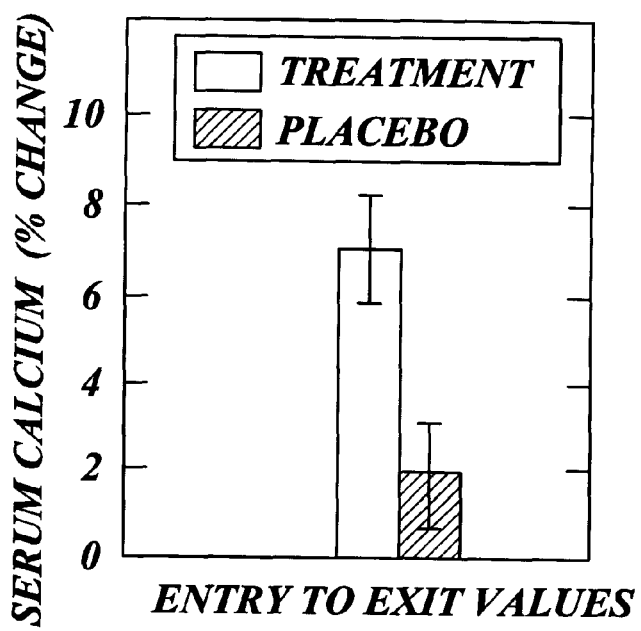
Figure 8C:
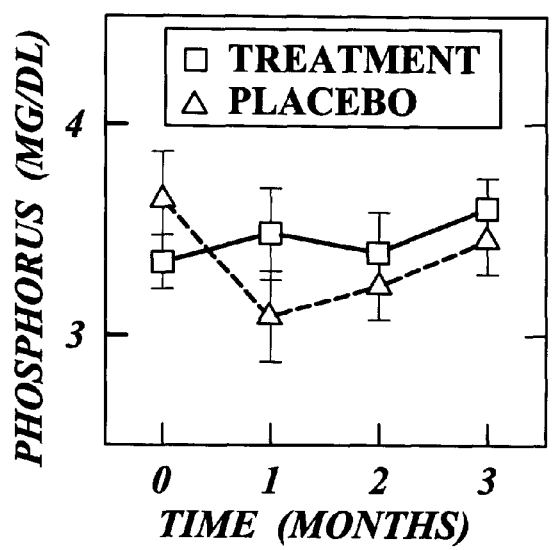
Figure 8D:
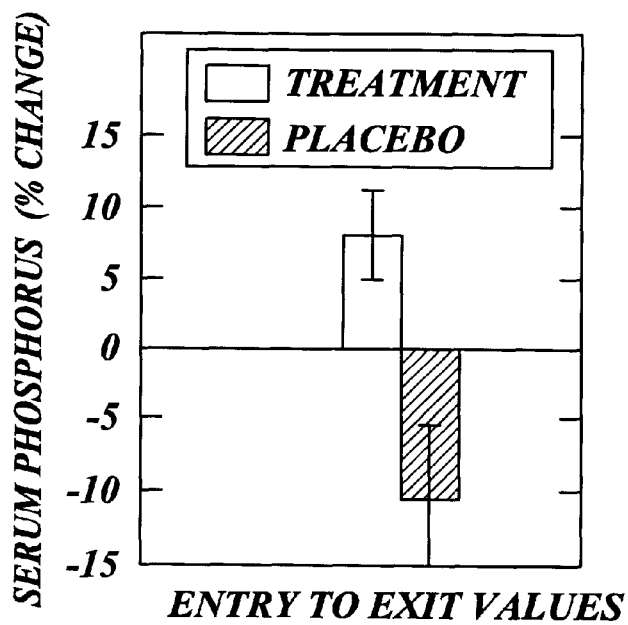

FIG. 7 shows the average weight change in patients in the treatment group versus those in the placebo group during the three month study. There was a weight gain of $4.88 \pm 1.92$ (SEM) pounds in the treatment group compared to a loss of $3.95 \pm 1.43$ pounds in the placebo group. Weight gain in the treatment group was statistically significant compared to the weight loss in the placebo group ($P<0.001$). Weight gain may be associated with using homeopathic dilutions of insulin-like growth factor which, in pharmacological doses, is known to participate in anabolic processes in the body.

FIGS. 8A–D show the change in serum calcium and phosphorus levels following three months of oral administration of homeopathic dilutions of growth factors compared to administration of placebo. Calcium is a significant mineral in the body and participates in numerous metabolic functions. Phosphorus contributes to formation and utilization of ATP, phosphorylated metabolic intermediates and nucleic acids. In the form of phospholipids and inositol polyphosphates, it plays critical roles in the signal transduction mechanisms after growth factor stimulation. Lymphocytes from HIV-infected individuals show aberrant inositol polyphosphate metabolism which reverses after AZT therapy (Nye et al. 1990). Both calcium and phosphorus are poorly absorbed in some HIV-positive persons.

All participants were within the normal ranges for serum calcium at entry into the study with a mean value of $8.87 \pm 0.074$ mg/dl. However, this is lower than a cohort of an equal number of age/sex matched non-HIV+patients whose serum calcium levels were $9.2 \pm 0.085$ mg/dl. Because calcium plays a critical role in signal transduction processes elicited by growth factors and because study participants were on the low side of normal, all participants were asked to add 1000 milligrams of calcium into their diet, if they were not using it already, to maximize the potential action of the high dilution growth facts. Calcium citrate or calcium chelated to several amino acids and acidic moieties were recommended for maximal absorption. During the clinical study, the treatment group started with serum calcium values of $8.8 \pm 0.10$ mg/dl and increased their serum calcium levels to $9.5 \pm 0.12$ mg/dl which represents a $7.14 \pm 1.2\%$ increase. In contrast, the placebo group entered the study with serum calcium values of $8.96 \pm 0.13$ mg/dl and ended the study with values of $9.04 \pm 0.07$ mg/dl, which is a $2.05 \pm 1.2\%$ increase. The difference in serum calcium levels between the two groups was statistically significant ($P<0.003$). The increase in calcium is consistent with increased body weight seen in the treatment group compared to the placebo group and may reflect greater absorption from the intestines.

Similarly, during the three-month double blind study, persons treated with combinations of homeopathic dilutions of growth factors increased serum phosphorus levels by $8.11 \pm 3.27\%$ while phosphorus levels in the placebo group decreased by $10.39 \pm 4.99\%$.

There was no evidence that oral administration of homeopathic dilutions of growth factors had toxic effects on any of the participants. None of the subjects in the treatment group had high liver enzyme function tests (LFT), SGPT (alanine aminotransferase), SGOT (aspartate aminotransferase), GGPT (gamma glutamyl-transpeptidase) at baseline or after any of the months of treatment. Three patients in the placebo group, however, had high LFT's at baseline and four patients in the placebo group had high LFTs after the three month clinical study. Thus, the randomization process did not equally distribute persons with poor liver function.

The differences in liver function between placebo and treatment patients at baseline raises the possibility that differences in CD4 lymphocyte counts between the groups could have been due to differences in health at baseline and not due to administration of homeopathic dilutions of growth factors. In order to address this possibility, changes in CD4 lymphocyte counts were correlated with LFT at baseline to determine whether patients who had abnormal LFT were also the patients who lost the most CD4 cells during the study. Table I indicates no obvious correlation between high liver enzymes and loss of CD4 cells in the three people taking placebo.

TABLE I

| Months | Patient #5 CD4 cells/mm$^3$ | Patient #7 CD4 cells/mm$^3$ | Patient #17 CD4 cells/mm$^3$ |
| --- | --- | --- | --- |
| 0 | 541 | 302 | 207 |
| 1 | 241 | 373 | 131 |
| 2 | 264 | 350 | 122 |
| 3 | 501 | 329 | 137 |
| Total Change in CD4 cells | −40 | +27 | −70 |

During the study there were no opportunistic infections in the treatment group and two in the placebo group; pneumocystis carini pneumonia, and severe autoimmune demyelinating polyneuropathy and myelopathy.

LISTEN measurements of electrical conductance at key skin points associated with organs known to be involved in HIV also indicate significant differences between the treatment and placebo groups during the three month clinical study.

Figure 9A:
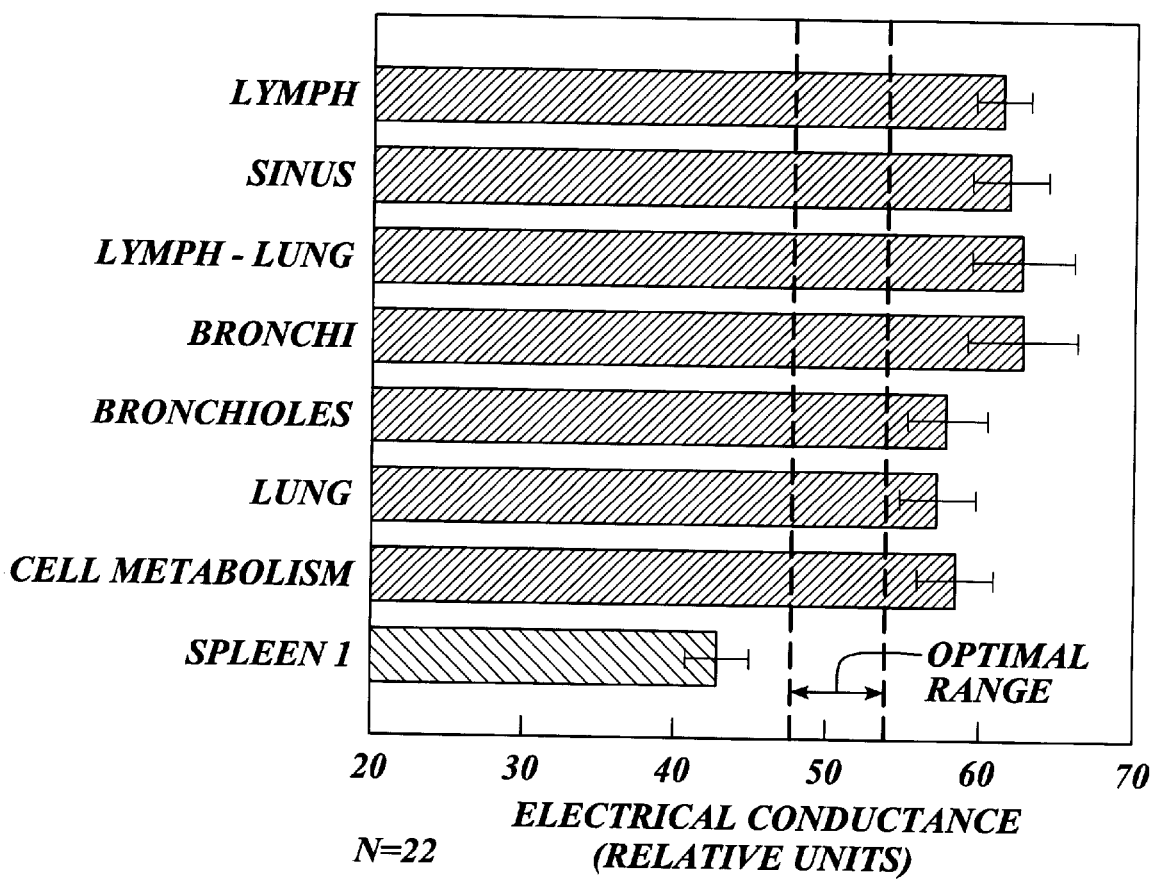
FIGS. 9A and B show electrical conductance values for HIV-positive patients prior to treatment with either homeopathic dilutions of growth factors or placebo.
Figure 9B:
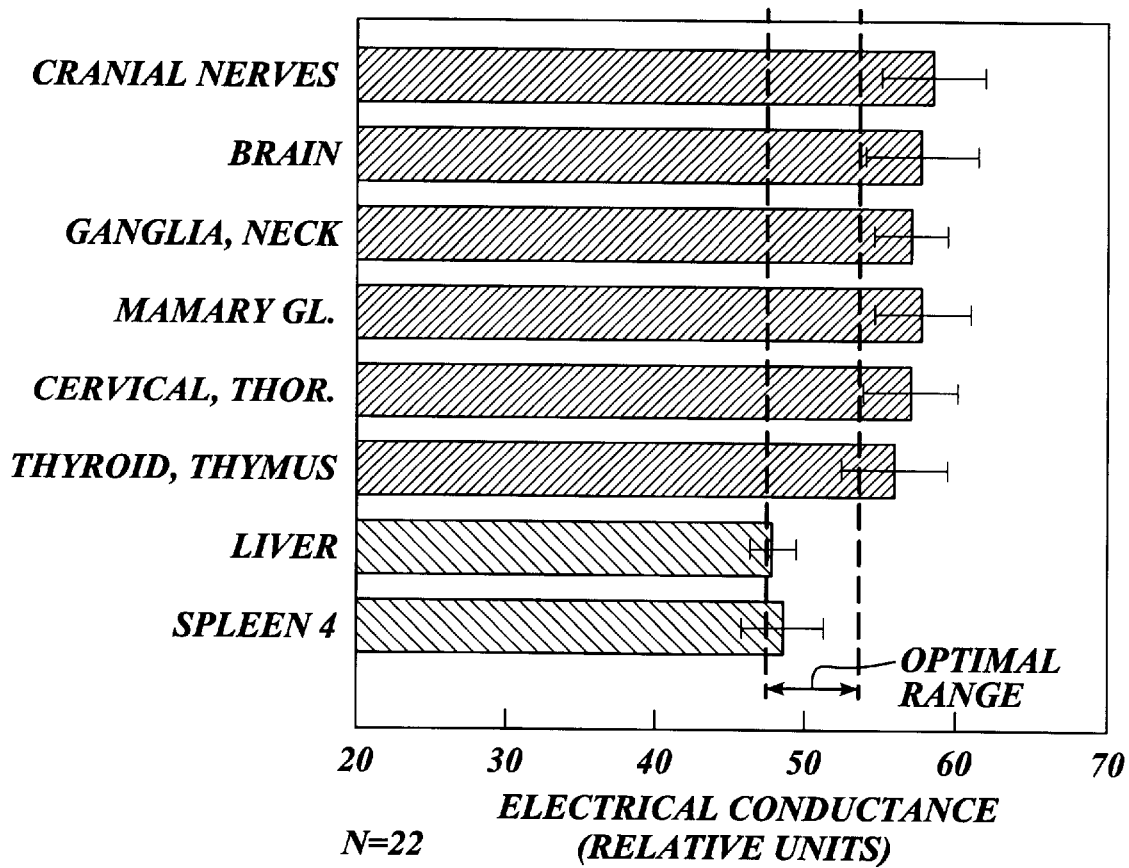
FIGS. 9C and D show five measurements of electrical conductance at four key skin conductance points, associated with the spleen, thymus, nerves and brain in HIV-positive patients administered either homeopathic dilutions of growth factors or placebo, respectively. The measurements were taken during the course of a three month clinical study.

Prior to commencement of treatment, the LISTEN system was employed to determine electrical conductance for each patient at 112 skin conductance points. Each conductance point correlates to specific organs and tissues of the body according to the Electroacupuncture According to Voll (EAV) system (see, for example, Am. J. Acupuncture 8:97–104, 1980). The optimal range for conductance ($50.78$ relative units$\pm 3.05$ Std. Dev.) was identified from measurements on 34 non-viral infected "healthy" controls. In the HIV-positive patients, electrical conductances at 16 of the skin points were found to be outside the normal range, with 13 of the points being above optimal, 1 being below optimal, and 2 falling at the lowest end of optimal, as shown in FIGS. 9A and B. These points, which correlate with the lymphatic system, lungs, cell metabolism, spleen, nerves, the neuroendocrine organs (including thymus-thyroid) and the liver are known to be key areas directly disrupted by HIV invention.

Figure 9C:
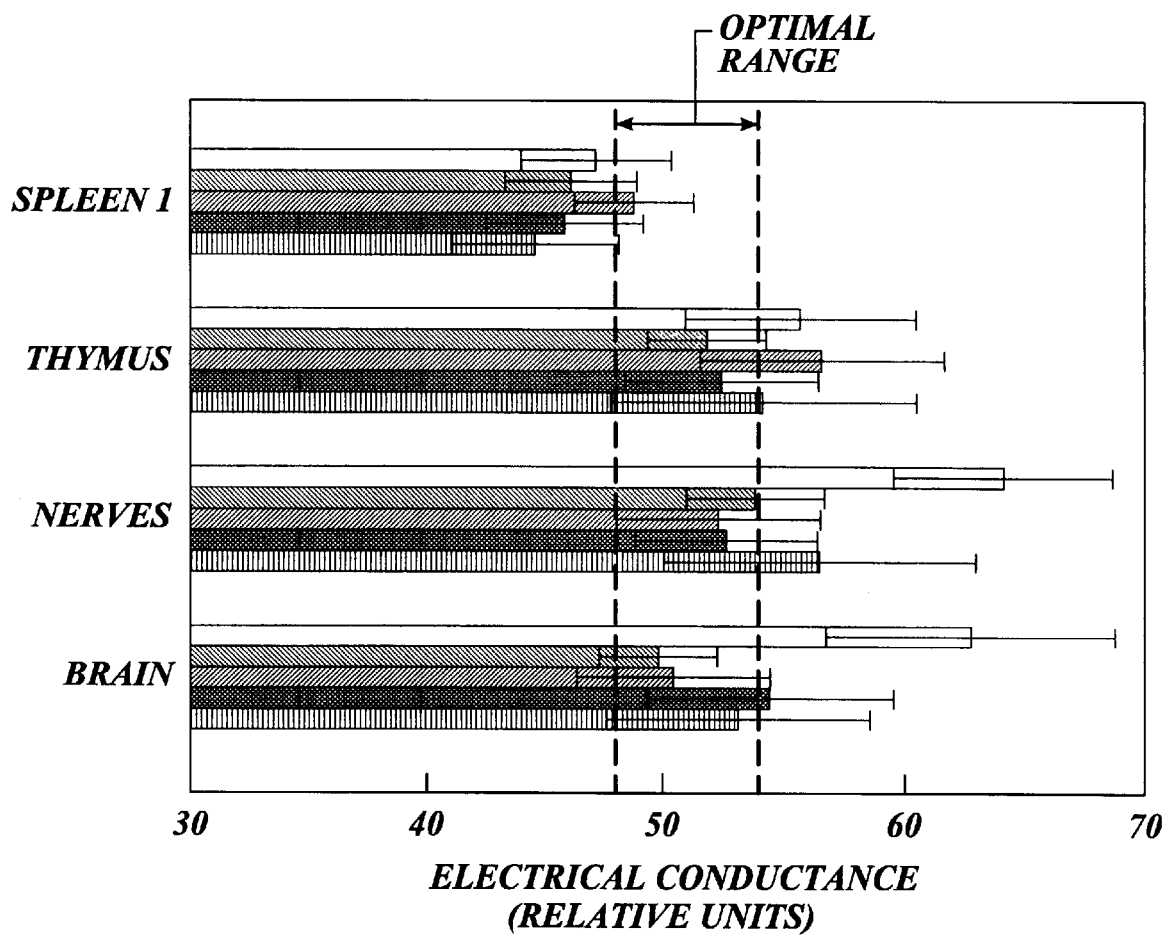
Figure 9D:
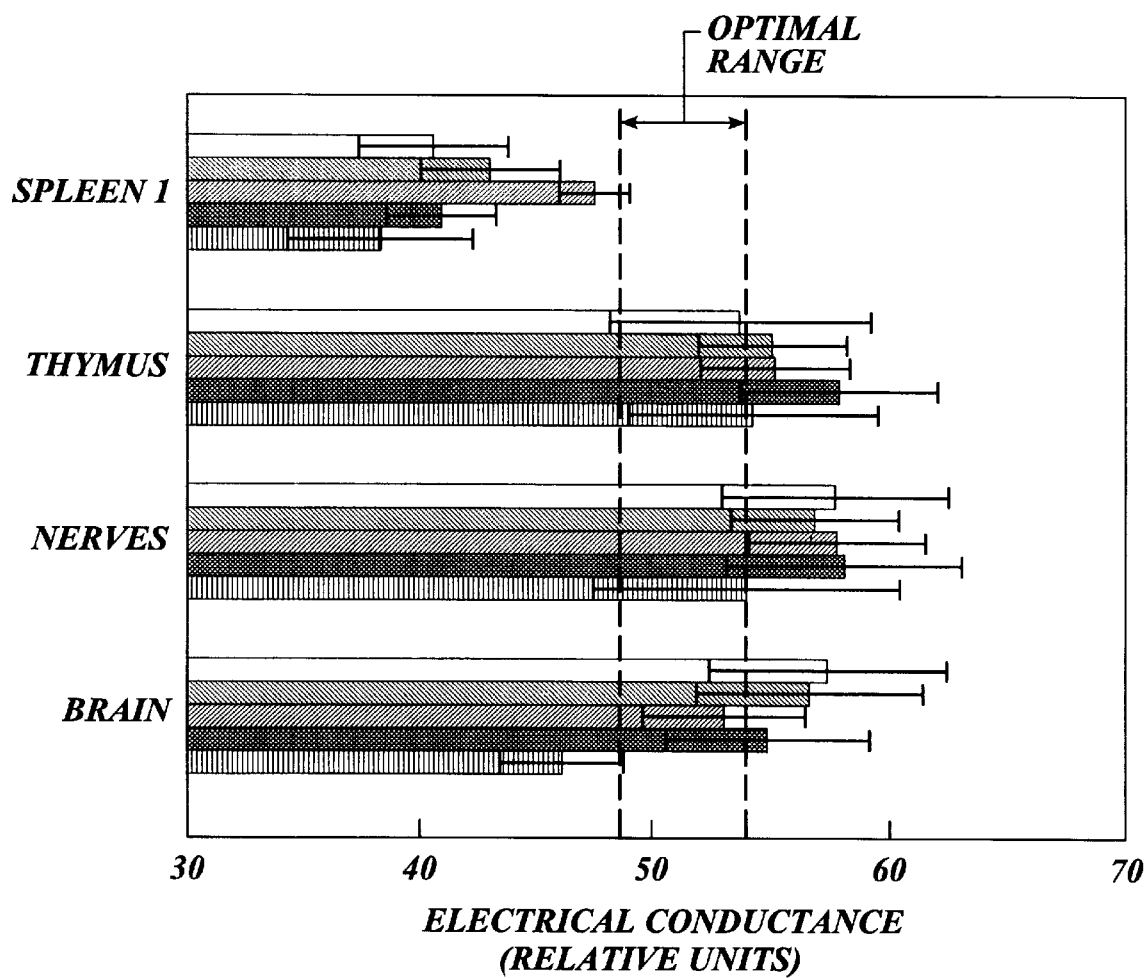

We continued to evaluate electrical conductance at four key areas (spleen, thymus, nerve and brain) not easily measurable by conventional means to evaluate over time the progress of these patients. Electrical conductances at these four key skin points were measured five times over the course of the three-month clinical study (every three weeks). As shown in FIGS. 9C and D measurements of spleen 1 electrical conductance were low in both groups at the onset of the study. The treatment group remained closer to the optimal range of electrical conductance throughout the study than did the placebo group. After six weeks, spleen 1 measurements were in the optimal range for the treatment group, while the placebo group's conductances peaked but did not reach optimal values. Both groups fell below their entry conductance measurements at the end of the study. The thymus, nerves and brain conductances were initially higher in the treatment group and improved, entering the optimal range three out of five times during the study. In contrast, the placebo group's conductances for thymus, nerves and brain remained out of the optimal range three out of five times. These data demonstrate the LISTEN's ability to prognostically and non-invasively determine if a given therapeutic, such as homeopathic dilutions of growth factors, is able to improve the health status of viral infected patients and acts upon the target tissues infected by the virus.

Following the clinical trial described above, the effects of continued self-administration of homeopathic dilutions of growth factors were compared with those of conventional antiveral therapy and administration of natural therapies. Specifically, seven patients continued to self-administer the combination of four homeopathic dilutions of growth factors described above (referred to as the GF group), seven patients began conventional antiviral therapy (referred to as the AV group_ and four patients took only natural therapies of their choice (referred to as the Nat group).

Figure 21:
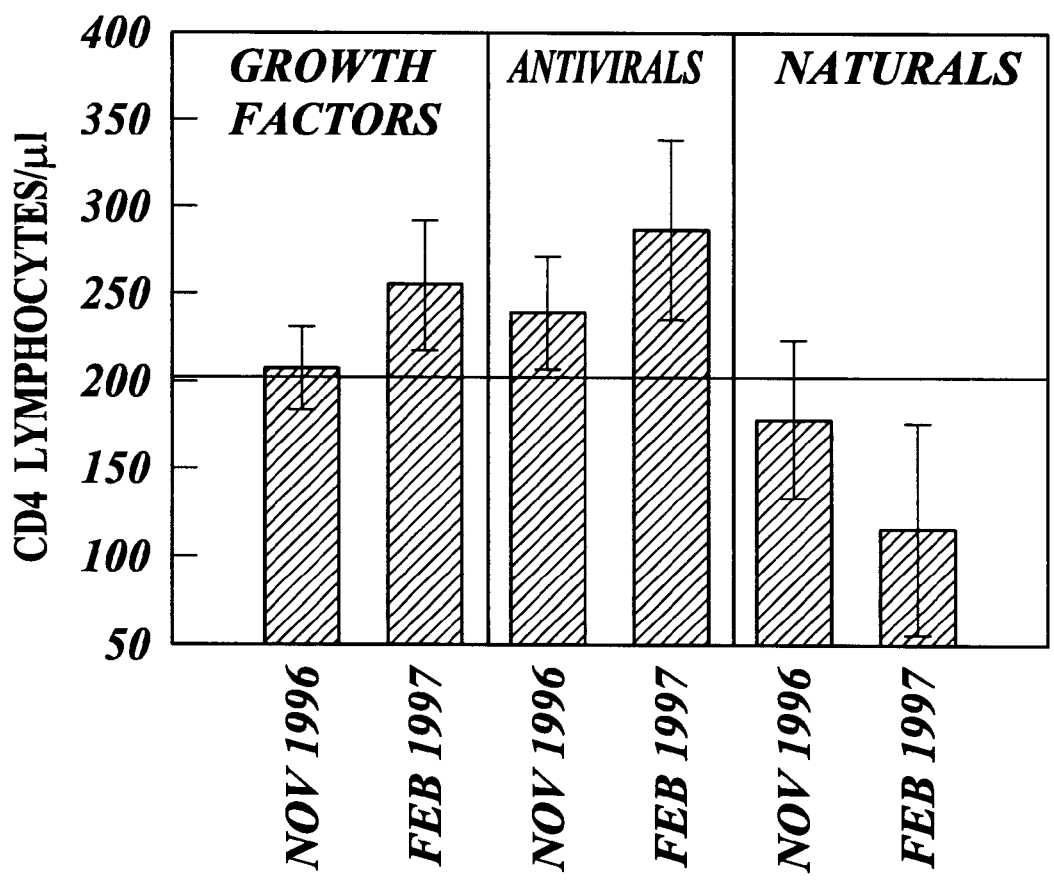
FIG. 21 shows the change in CD4 lymphocyte count over a three month period for HIV-positive patients administered either homeopathic dilutions of growth factors (GF group), conventional antiviral therapies (AV group) or natural medicines (Nat group).
Figure 22:
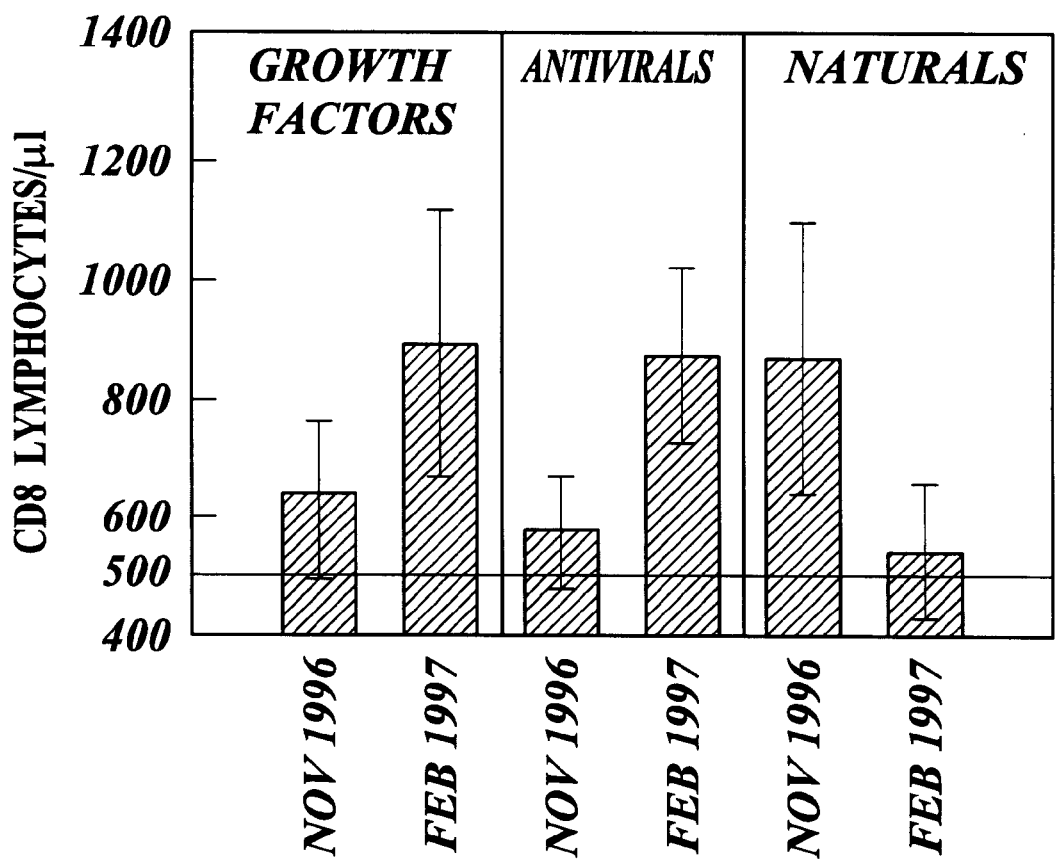
FIG. 22 shows the change in CD8 lymphocyte over a three month period for HIV-positive patients administered either homeopathic dilutions of growth factors (GF group), conventional antiviral therapies (AV group) or natural medicines (Nat group)
Figure 23:
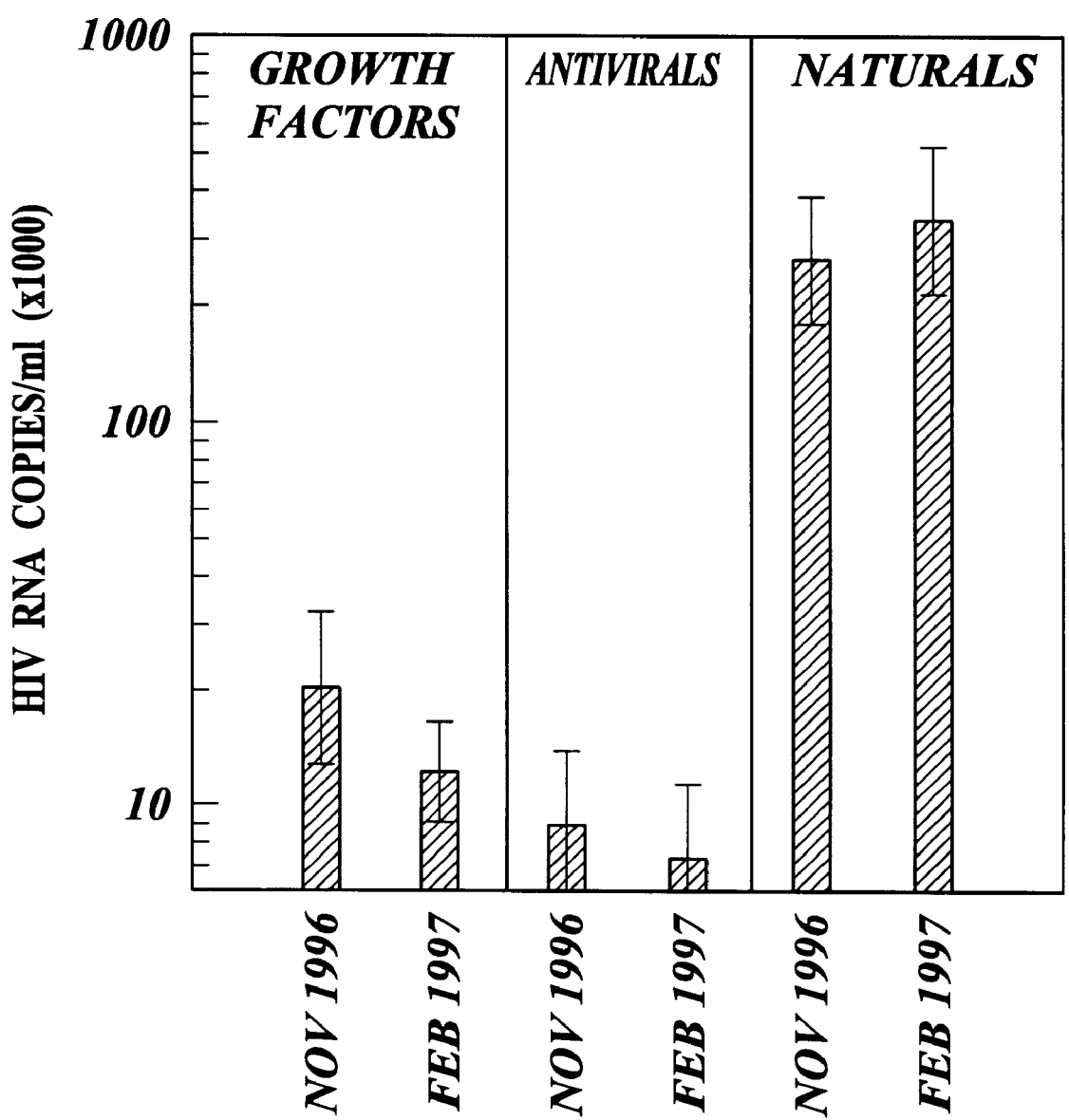
FIG. 23 shows the change in HIV viral load over a three month period for HIV-positive patients administered either homeopathic dilutions of growth factors (GF group), conventional antiviral therapies (AV group) or natural medicines (Nat group)

As shown in FIGS. 21 and 22, over a three month period, CD4 and CD8 counts decreased substantially in patients using only natural medicines, indicating disease progression. In contrast, lymphocyte cell counts increased in patients using either homeopathic dilutions of growth factors or conventional antiviral therapies. The HIV viral load data (FIG. 23)) also indicate disease progression within the Nat group, with viral loads greater than 230,000 RNA copies/ml of HIV in November 1996 and 365,000 RNA copies/ml of HIV in February 1997. The viral loads of the GF and AV groups were substantially lower, with the viral load for the GF group being 1.5 logs lower than the Nat group. The RNA load for the AV group was lower than that of the GF group in November 1996 but was not significantly lower than that for the GF group in February 1997. This data suggest that the immune systems of the GF group are learning how to effectively fight off the HIV virus with the assistance of conventional antiviral therapy.

Figure 24:
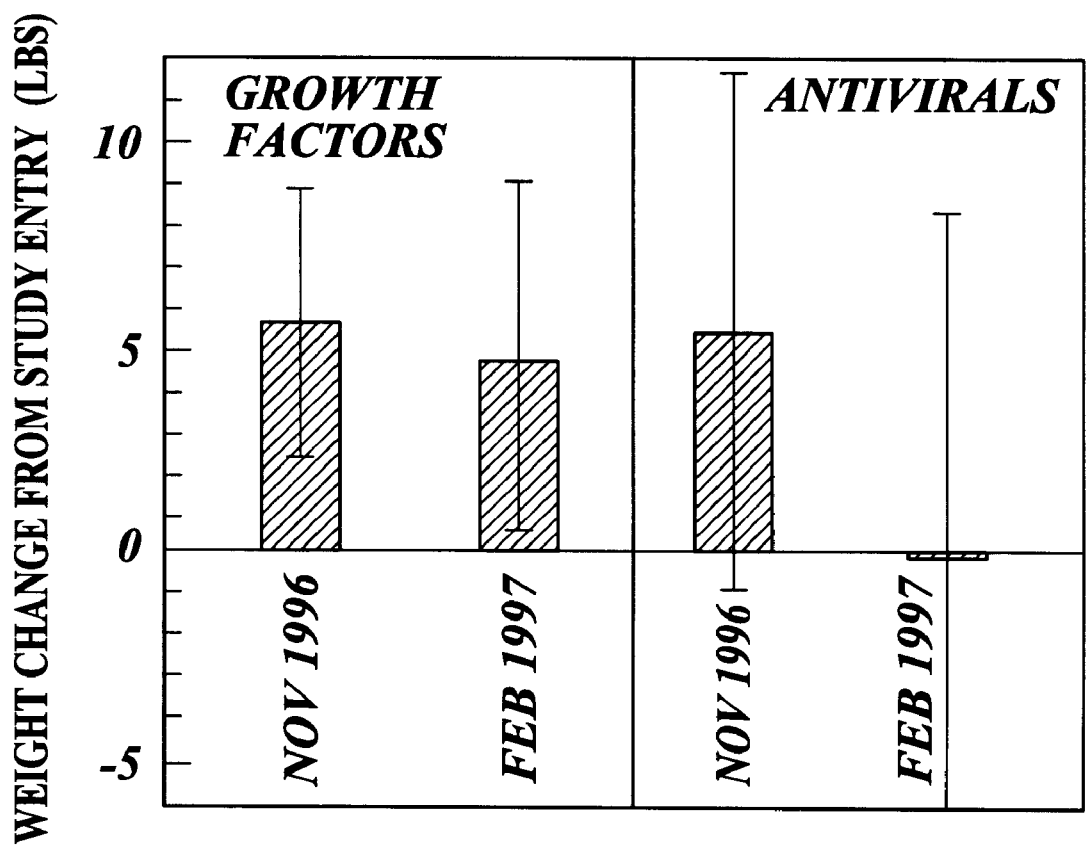
FIG. 24 shows the weight change in HIV-positive patients administered homeopathic dilutions of growth factors (GF group) compared to that in HIV-positive patients administered conventional antiviral therapies (AV group).
Figure 25:
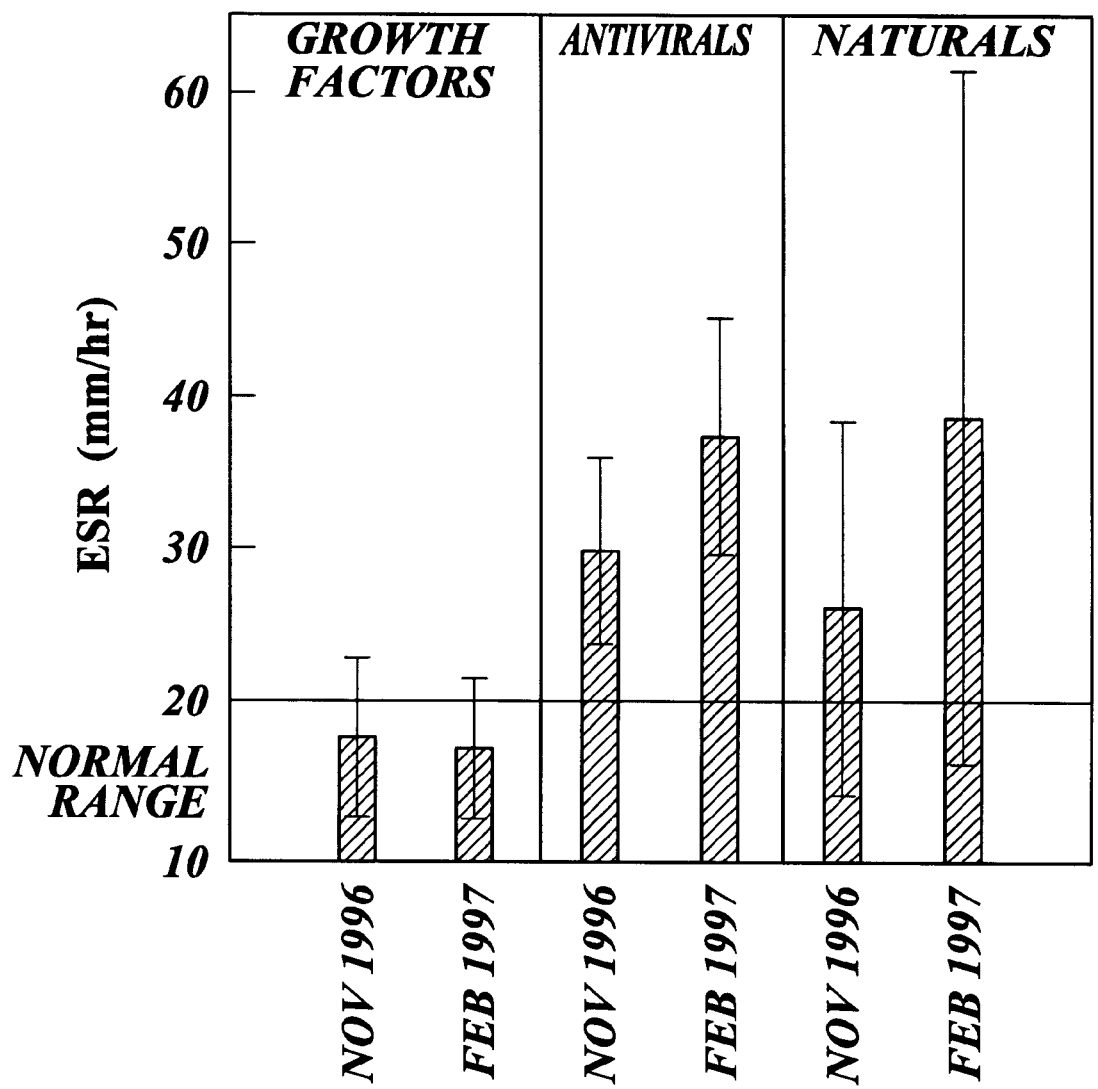
FIG. 25 shows the erythrocyte sedimentation rates in HIV-positive patients administered either homeopathic dilutions of growth factors (GF group), conventional antiviral therapies (AV group) or natural medicines (Nat group).

FIG. 24 illustrates that weight grain in the GF group between November 1996 and February 1977 was stable compared to significant weight loss in the AV group over the same time period. As shown in FIG. 25, erythrocyte sedimentation rates (ESR) in the GF group remained at normal levels during this study, while the ESR values for the AV and Nat groups continued to increase. As discussed above, EST is a measure of general infection and/or inflammation levels. Similarly, the maintenance of normal body weight is indicative of overall good health including proper function of the immune system. The data from this study suggest that the immune systems of patients taking conventional antiviral therapies are not fully operating to defend the body's tissue health and integrity.

Figure 26:
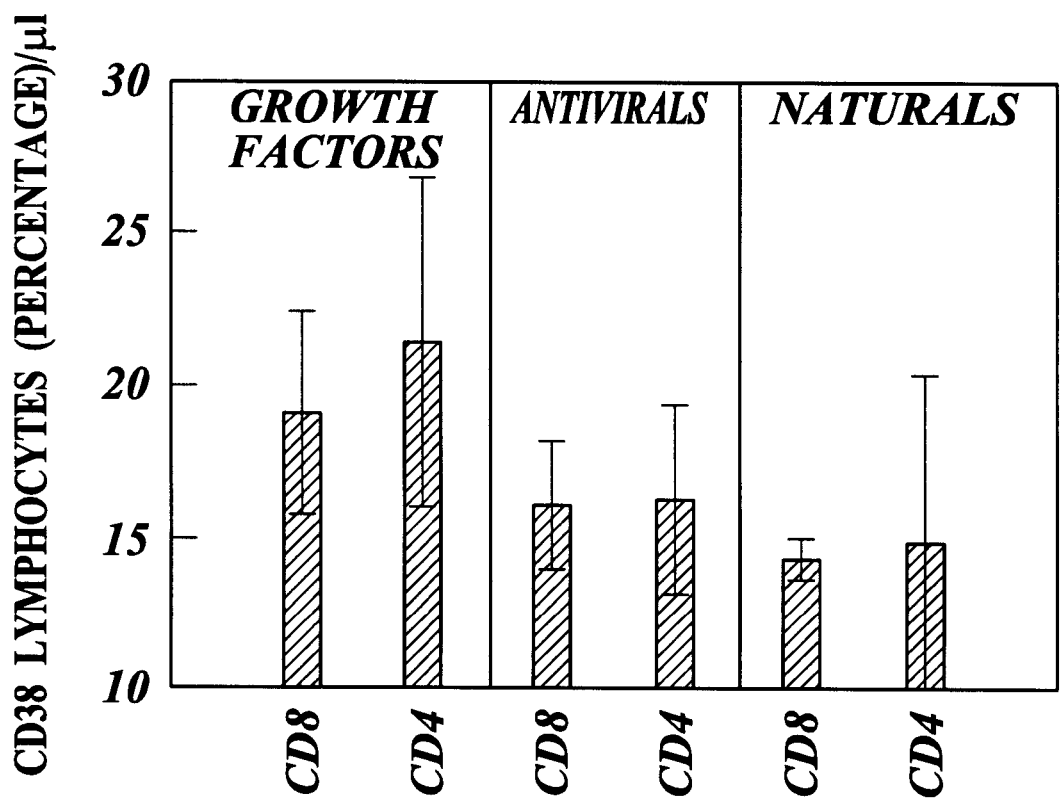
FIG. 26 shows the percentage of $CD38^+$ lymphocytes in HIV-positive patients administered either homeopathic dilutions of growth factors (GF group), conventional antiviral therapies (AV group) or natural medicines (Nat group).
Figure 27:
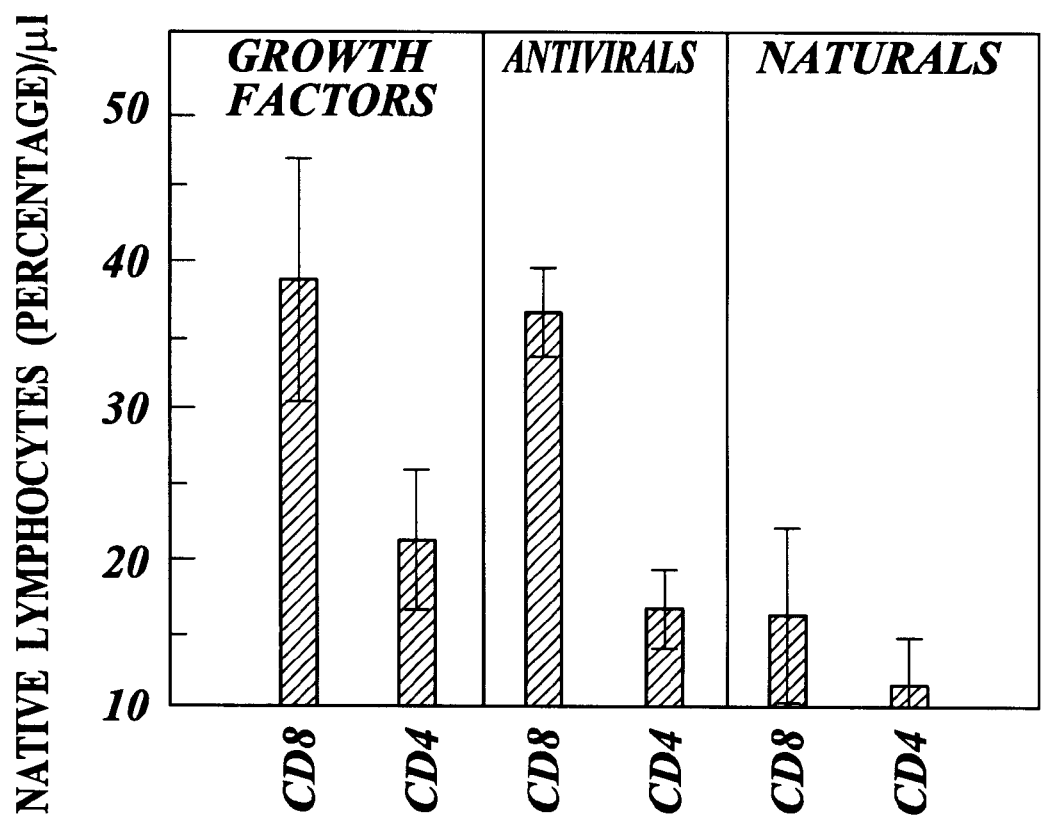
FIG. 27 shows the percentage of naive lympocytes in HIV-positive patients administered either homeopathic dilutions of growth factors (GF group), conventional antiviral therapies (AV group) or natural medicines (Nat group).

FIG. 26 shows that the level of cell signaling lymphocytes, CD38$^+$ lymphocyte subclasses of the CD4 and CD8 subsets, were higher in the GF group than in the AV or Nat groups. This suggests that cell signaling is enhanced by administration of homeopathic dilutions of growth factors. CD38$^+$ lymphocytes also result in new cell functioning which may play an important role in the ability of an HIV$^+$-patient's immune system to effectively manage HIV infection. As shown in FIG. 27, the level of naive lymphocytes (CD45RA'), i.e., lymphocytes that have not yet been exposed to a specific antigen and that are therefore nor targets for HIV replication, was increased in both the GF and AV groups decreased in the Nat group, with the levels being slightly higher in the GF group than in the AV group.

Figure 10:
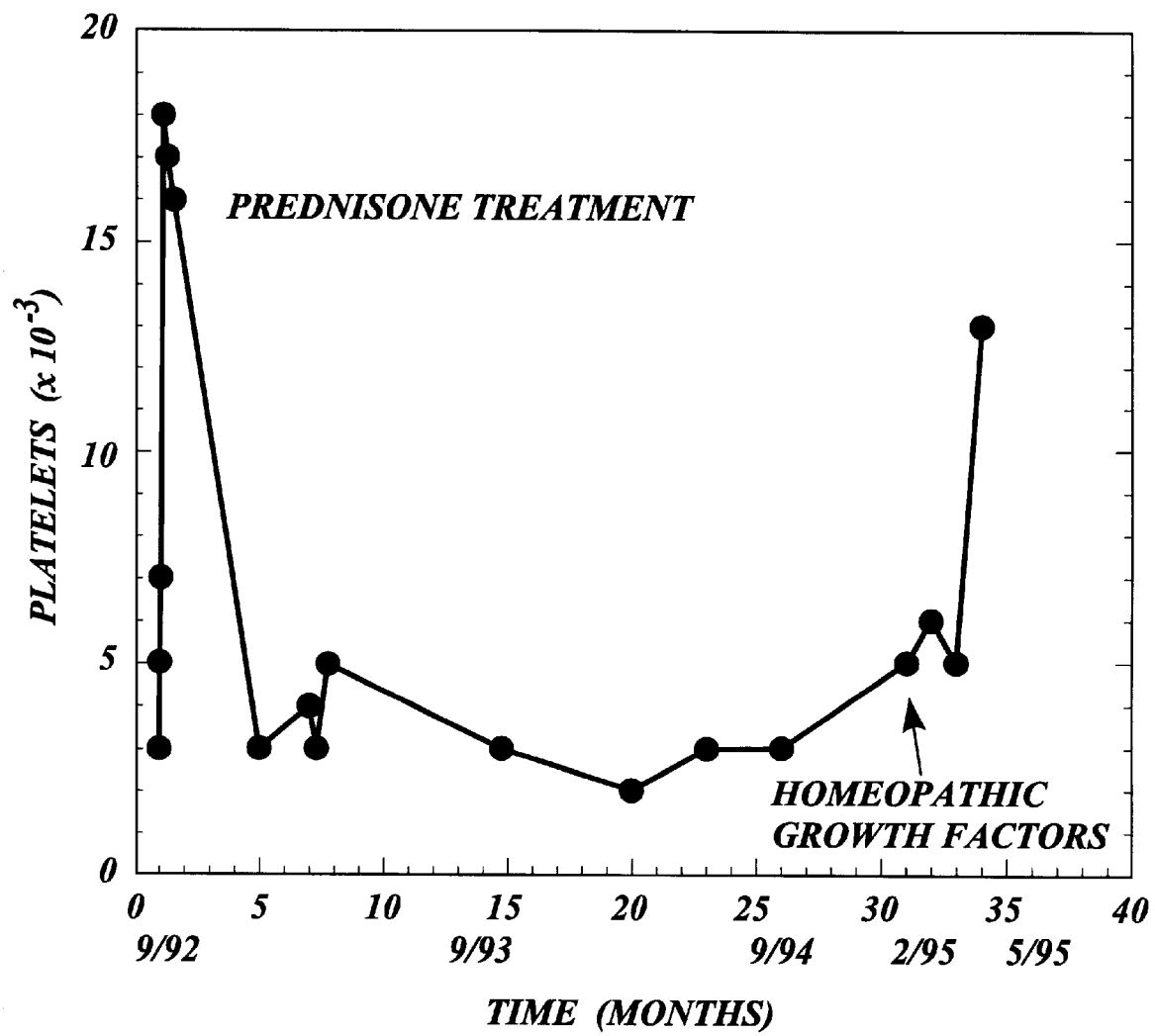
FIG. 10 shows the change in platelet count over time in an HIV-positive patient with thrombocytopenia both before and during treatment with homeopathic dilutions of growth factors.

FIG. 10 shows a change in platelet counts over a three-year period for an HIV-positive patient with idiopathic thrombocytopenia purpura. Prior to the commencement of treatment, the patient had a CD4 count of 56 cells/mm$^3$. At the beginning of the timeline shown in FIG. 9, the patient was treated with prednisone for three months. During the first two weeks of prednisone treatment, the platelet counts increased from 6,000 to 17,000 cells/ml, and then dropped to 2,000–3,000 and stayed at that level for the next two years. Following oral administration of the same homeopathic dilutions of growth factors used in the three-month clinical study described above, the platelet count increased to 13,000. Immediately prior to treatment with homeopathic dilutions of growth factors, the patient was treated with shark liver oil and alkylglycerols. No intervention other than prednisone and homeopathic dilutions of growth factors effected the platelet count.

EXAMPLE 2

Using the protocol outlined above, eleven HIV positive patients with CD4 counts in the range 67–570 cells/mm$^3$ were evaluated with the LISTEN system to determine whether electrical conductances could be balanced with growth factor signals. Electrical conductance was measured at points known to be weak in HIV and AIDS patients, including points corresponding to the spleen (SPCL), spleen lymphocytes homing to the upper body (SP1L), spleen lymphocytes homing to the lower body and gastrointestinal tract (SP2L), spleen blood filtering function (SP3L), environmentally related allergies (AL1R), general allergies (ALCR), lymph tissue of lungs (LY4R), lymph nodes (LY1R), general lymph function (LYCR), lymph drainage of tonsils/throat (LY1aR) and connective tissue (FICR).

Signals corresponding to growth factors at potencies of 6 C (1:100 diluted six times=$10^{-12}$), 30 C (1:100 diluted thirty times=$10^{-60}$), 200 C (1:100 diluted 200 times=$10^{-400}$), 1000 C (1:100 diluted 1000 times=$10^{-2000}$), also termed "1M," were administered.

Table II, shows the results of a preliminary study to test which signals corresponding to different potencies growth factors would balance electrical conductances (i.e., electrical conductance achieved optimal range) in eleven HIV-positive patients with CD4 counts ranging from 66 to 400 cells/mm$^3$.

TABLE II

|  | Appeared No. of People | 6C | 30C | 200C | 1000C |
|---|---|---|---|---|---|
| Nerve Growth Factor (NGF) | 7/11 | 3 | 2 | 1 | 4 |
| Insulin-like Growth Factor-1 (IGF$_1$) | 10/11 | 6 | 4 | 6 | 7 |
| Acidic Fibroblast Growth Factor (aFGF) | 6/11 | 2 | 3 | 1 | 5 |
| Basic Fibroblast Growth Factor (bFGF) | 6/11 | 2 | 2 | 5 | 4 |
| BB Platelet-derived Growth Factor (BB-PDGF) | 9/11 | 3 | 5 | 1 | 5 |
| AA Platelet-derived Growth Factor (AA-PDGF) | 8/11 | 3 | 4 | 3 | 2 |
| AB Platelet-derived Growth Factor (AB-PDGF) | 7/11 | 3 | 5 | 3 | 4 |
| transforming Growth Factor alpha (TGFα) | 5/11 | 2 | 2 | 4 | 3 |
| Epidermal Growth Factor (EGF) | 5/11 | 0 | 2 | 2 | 3 |
| Stem Cell Factor (SCF) | 5/11 | 3 | 1 | 3 | 2 |
| Transforming Growth Factor-beta 1 (TGFβ1) | 6/11 | 3 | 3 | 1 | 6 |
| Transforming Growth Factor-beta 2 (TGFβ2) | 4/11 | 1 |  | 2 | 1 |
| Granulocyte-Macrophage Colony Stimulating Factor (GM-CSF) | 7/11 | 2 | 0 | 4 | 3 |
| Tumor Necrosis Factor alpha (TNFα) | 7/11 | 4 | 2 | 4 | 4 |
| Macrophage Colony Stimulating Factor (M-CSF) | 7/11 | 2 | 2 | 2 | 4 |

In ten of the eleven patients, administration of insulin-like growth factor (IGF$_1$) signal brought the electrical conductance back into the normal range, with some patients responding to more than one dilution. BB Platelet-derived growth factor (BB-PDGF) and AA platelet-derived growth factor (AA-PDGF) were also highly effective in returning electrical conductance measurements to normal. Signals corresponding to higher dilutions of growth factors appeared to be more effective in restoring the electrical conductance to normal values.

Tables III and IV show which radio frequency signals corresponding to homeopathic dilutions of growth factors balanced electrical conductance at spleen acupuncture points and lymphatic skin conductance points (labeled YES) and which did not balance electrical conductance (labeled NO) for five HIV-positive patients with CD4 counts of 225–395 cells/mm$^3$ (Table III) and five HIV-positive patients with CD4 counts of 66–170 cells/mm$^3$ (Table IV).

TABLE III

|  | YES 6c | YES 30c | YES 200c | YES 1M | NO 6c | NO 30c | NO 200c | NO 1M |
|---|---|---|---|---|---|---|---|---|
| PDGF$_{BB}$ | 1 | 5 | 3 | 4 | 3 | 0 | 2 | 1 |
| GM-CSF | 3 | 0 | 4 | 5 | 1 | 4 | 1 | 2 |
| TGF$_{β1}$ | 1 | 4 | 2 | 3 | 3 | 1 | 4 | 1 |
| IGF$_1$ | 2 | 2 | 3 | 4 | 2 | 3 | 1 | 2 |
| Insulin | 1 | 4 | 4 | 3 | 3 | 1 | 1 | 2 |
| TNF$_α$ | 1 | 3 | 5 | 5 | 3 | 3 | 0 | 0 |
| PDGF$_{AA}$ | 1 | 5 | 3 | 3 | 3 | 0 | 2 | 2 |
| PDGF$_{AB}$ | 1 | 4 | 1 | 4 | 3 | 1 | 4 | 2 |
| TGF$_α$ | 1 | 2 | 3 | 2 | 3 | 3 | 2 | 1 |
| TGF$_{β2}$ | 2 | 1 | 2 | 3 | 2 | 3 | 3 | 2 |
| SCF | 2 | 1 | 3 | 4 | 2 | 3 | 2 | 1 |
| MCSF | 2 | 2 | 3 | 0 | 2 | 2 | 3 | 5 |
| EGF | 2 | 3 | 3 | 4 | 2 | 2 | 2 | 1 |
| NGF | 2 | 4 | 2 | 3 | 3 | 1 | 3 | 2 |
| aFGF | 2 | 2 | 1 | 4 | 3 | 3 | 4 | 2 |
| bFGF | 2 | 3 | 3 | 5 | 2 | 1 | 2 | 0 |
| TOTALS | 26 | 45 | 43 | 66 | 40 | 31 | 31 | 25 |

TABLE V

|  | YES 6c | YES 30c | YES 200c | YES IM | NO 6c | NO 30c | NO 200c | NO IM |
|---|---|---|---|---|---|---|---|---|
| PDGF$_{BB}$ | 2 | 2 | 0 | 0 | 1 | 2 | 5 | 5 |
| GM-CSF | 0 | 0 | 2 | 3 | 1 | 3 | 3 | 2 |
| TGF$_{β1}$ | 2 | 2 | 0 | 5 | 1 | 2 | 5 | 4 |
| IFG1 | 3 | 2 | 2 | 3 | 0 | 2 | 3 | 2 |
| Insulin | 2 | 1 | 2 | 2 | 1 | 3 | 3 | 2 |
| TNF$_α$ | 2 | 2 | 3 | 5 | 1 | 2 | 2 | 0 |
| PDGF$_{AA}$ | 3 | 1 | 1 | 0 | 0 | 3 | 4 | 5 |
| PDGF$_{AB}$ | 2 | 2 | 1 | 1 | 1 | 2 | 4 | 4 |
| TGF$_α$ | 3 | 1 | 2 | 0 | 0 | 3 | 4 | 5 |
| TGF$_{β2}$ | 2 | 2 | 1 | 1 | 1 | 2 | 4 | 4 |
| SCF | 2 | 2 | 2 | 3 | 1 | 2 | 3 | 1 |
| MCSF | 1 | 0 | 1 | 4 | 2 | 5 | 4 | 1 |
| EGF | 1 | 2 | 0 | 0 | 2 | 2 | 5 | 5 |
| NGF | 3 | 1 | 1 | 1 | 1 | 3 | 4 | 4 |
| aFGF | 1 | 1 | 0 | 2 | 2 | 3 | 5 | 3 |
| bFGF | 0 | 1 | 2 | 2 | 3 | 3 | 3 | 3 |
| TOTALS | 31 | 22 | 20 | 32 | 18 | 42 | 61 | 50 |

The group with the higher CD cell counts was overall more responsive to signals of growth factors, responding positively 180 times to radio frequency signals corresponding to homeopathic dilutions of growth factors, compared to only 105 times in the group with lower CD4 cells counts. There was almost an inverse relationship between the higher and lower CD4 cell count groups in terms of YES and NO responses to the growth factors tested in this study. The group with CD4 cell counts above 225 cells/mm$^3$ primarily responded YES to PDGF at $10^{-60}$ and $10^{-2000}$, GM-CSF at $10^{-400}$ and $10^{-2000}$, TGF$_β$1 at $10^{-60}$, and IGF$_1$ at $10^{-2000}$, with positive responses to these growth factors, in general, a total of 46 times and negative responses only 31 times. In contrast, patients with CD4 cell counts of 170 cells/mm3 or lower primarily responded NO 41 times and responded YES only 30 times.

In a separate study, an asymptomatic HIV-positive patient was given a simultaneous radio frequency signal challenge of HIIV using the LISTEN system while scanning dilutions specifically for bFGF to determine which dilutions between 6x and 6 C might be useful. Signals corresponding to dilutions of 20×, 30×, 200×, 400×, 600×, 800× and 6 C were found to bring the electrical conductances back into the optimal range.

EXAMPLE 3

Two HIV-positive patients were treated with signals for homeopathic dilutions of growth factors using the LISTEN system several times per week for a period of three months using the protocol outlined above.

Peripheral blood lymphocyte counts were obtained for both patients at, or shortly after, the commencement of treatment with homeopathic growth factor signals and again at the end of the study. Prior to the commencement of treatment, both patients had a CD4 count of less than 200. Patient 2 was treated with homeopathic growth factor signals alone, while patient 1 was treated with a combination of homeopathic growth factor signals and, in addition, was treated therapeutically with homeopathic medicines and/or some botanicals corresponding to the digital codes from the LISTEN. Neither patient was on anti-retroviral therapy.

Signals of homeopathic growth factors corresponding to a combination of dilutions were administered for one second to skin points associated with organs and tissues known to be weak in HIV and AIDS patients, as outlined in Example 2. Growth factors were selected based on their ability to effectively return conductance levels to normal. The number of times that signals corresponding to specific growth factors returned electrical conductance levels to optimal are shown in Table V.

TABLE V

| GROWTH FACTORS | NUMBER OF APPEARANCES | |
|---|---|---|
| | Patient One | Patient Two |
| Nerve Growth Factor (NGF) | 14 | 7 |
| Insulin-like Growth Factor-1 (IGF$_1$) | 4 | 8 |
| Acidic Fibroblast Growth Factor (aFGF) | 13 | 6 |
| Basic Fibroblast Growth Factor (bFGF) | 4 | 0 |
| BB Platelet-derived Growth Factor (BB-PDGF) | 1 | 8 |
| AA Platelet-derived Growth Factor (AA-PDGF) | 5 | 0 |
| AB Platelet-derived Growth Factor (AB-PDGF) | 0 | 0 |
| Transforming Growth Factor alpha (TGFα) | 10 | 0 |
| Epidermal Growth Factor (EGF) | 3 | 0 |
| Stem Cell Factor (SCF) | 5 | 0 |
| Transforming Growth Factor-beta 1 (TGFb1) | 5 | 0 |
| Transforming Growth Factor-beta 2 (TGFβ2) | 0 | 2 |
| Granulocyte/Macrophage-Colony Stimulating Factor (GM-CSF) | 0 | 2 |
| Tumor Necrosis Factor alpha (TNFα) | 0 | 0 |
| Macrophage-Colony Stimulating Factor (M-CSF) | 0 | 0 |

Nerve growth factor (NGF), acidic fibroblast growth factor (aFGF) and transforming growth factor alpha (TGFα) were most effective in bringing the electrical conductance measurements back into the normal range.

Figure 11A:
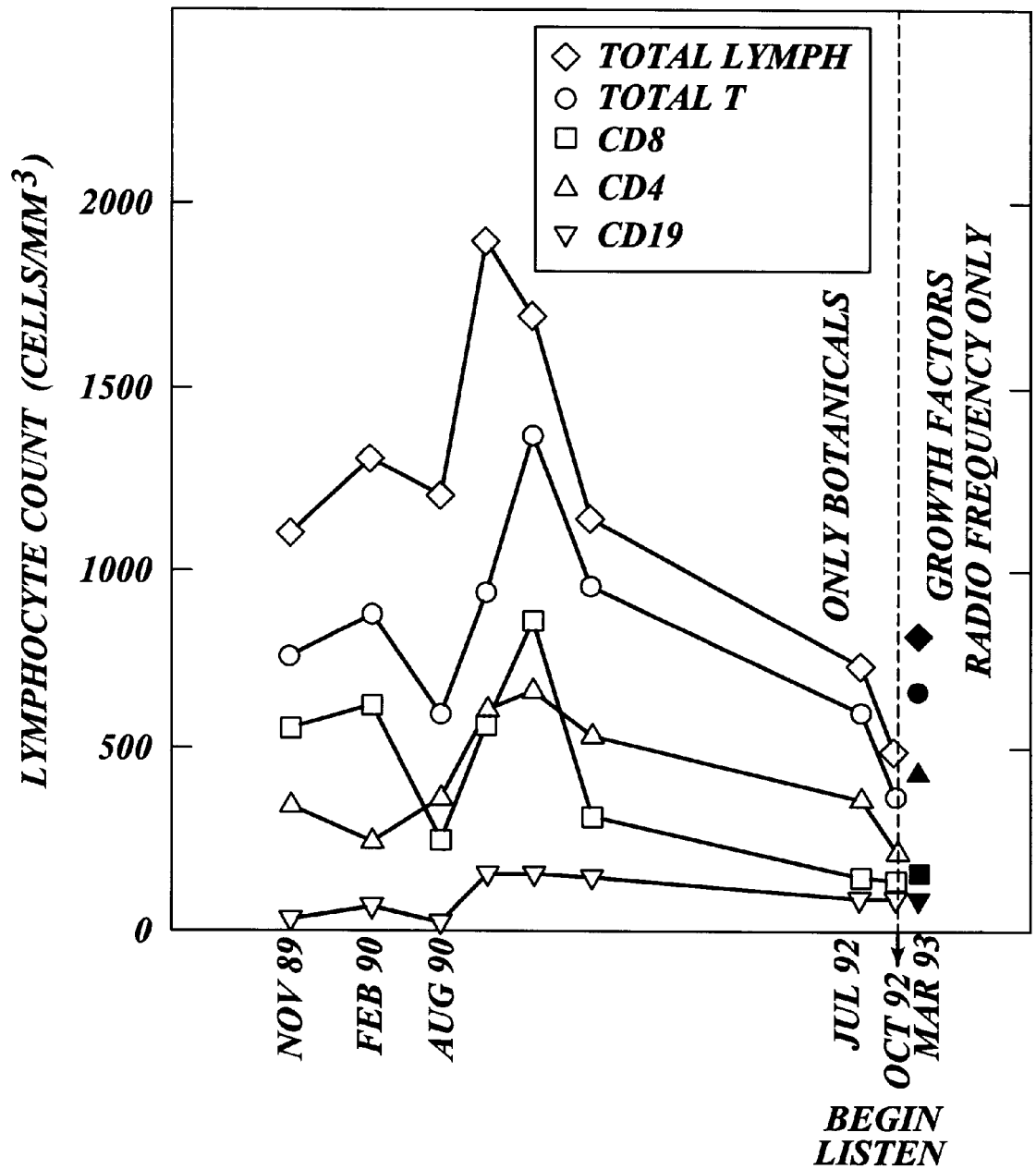
FIGS. 11A and B show the change in peripheral blood lymphocyte counts for two HIV-positive patients following treatment with radio frequency signals corresponding to homeopathic dilutions of growth factors. Neither of these patients were taking any conventional therapeutics. Both were taking natural medicines.

Prior to being treated with homeopathic growth factor signals, patient 2 had been treated with a variety of different botanicals. For the four-month period immediately prior to the commencement of homeopathic growth factor treatment, patient 2 was treated with the botanical bitter melon (called momordica) which resulted in increases in CD8, CD3, CD2 and CD19 counts of more than 50 percent. Bitter melon (momordica) was then discontinued. As shown in FIG. 11A, administration of signals corresponding to homeopathic growth factors resulted in a slight increase in patient 2's peripheral blood lymphocyte counts without any other medical treatment. The average loss of CD4 cells in HIV-positive patients is 20% of the cells per year.

Figure 11B:
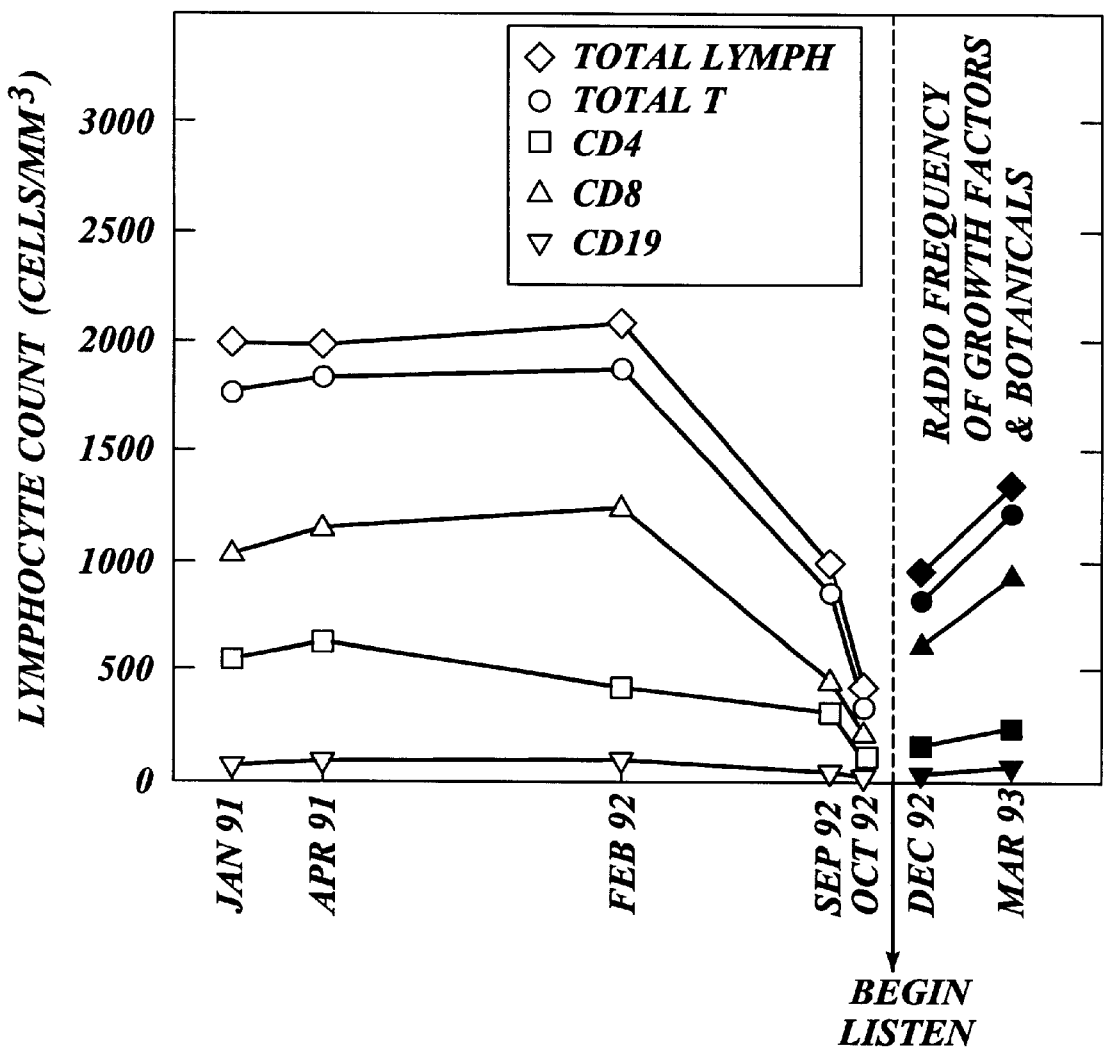

For patient 1, administration of signals corresponding to homeopathic dilutions of growth factors increased the CD4 count by 76%, while the CD8, CD2 and CD3 counts increased by 38%, as shown in FIG. 11B.

Figure 12:
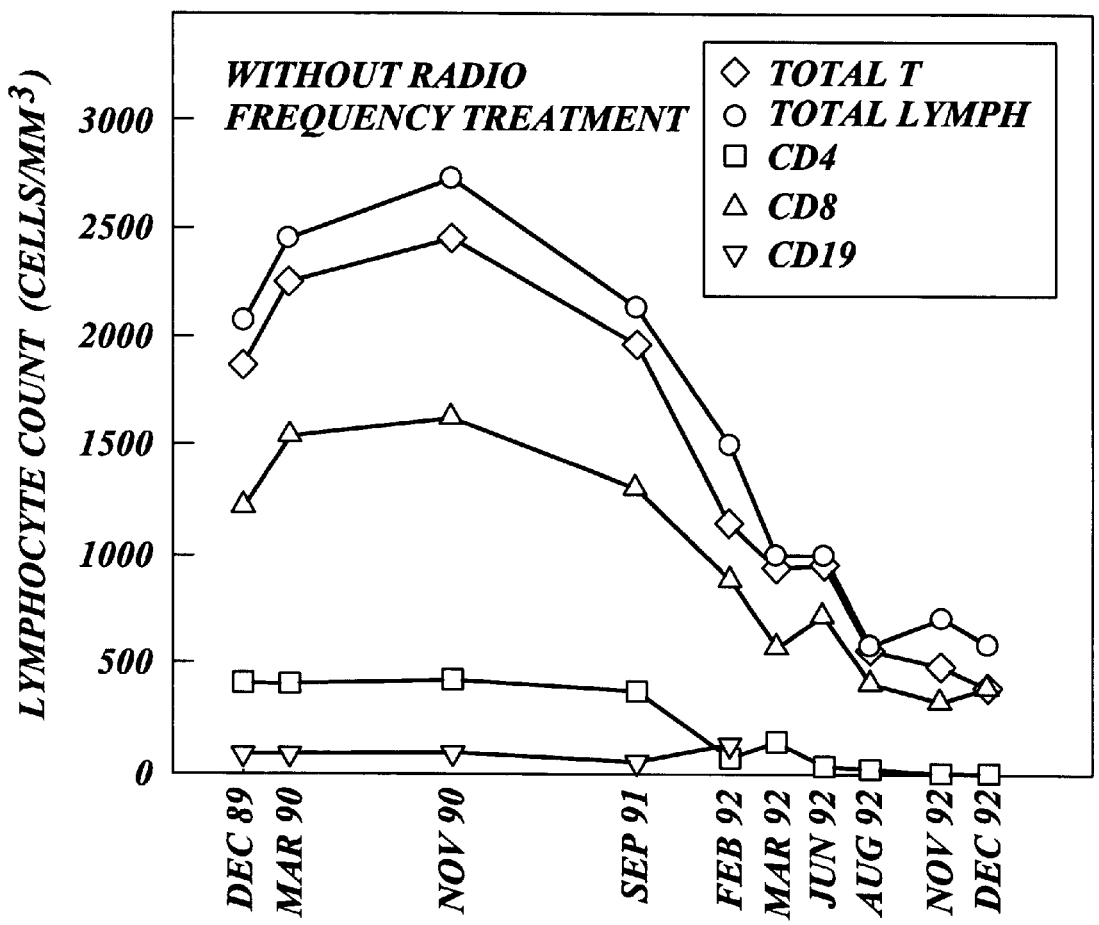
FIG. 12 shows the change in peripheral blood lymphocyte counts over time for a control HIV-positive patient who was not taking any conventional medicine, only natural medicines. This patient did not receive any radio frequency signals corresponding to homeopathic dilutions of growth factors.

These results are in marked contrast to the typical course of progression for HIV and AIDS in which the lymphocyte count continues to drop as the disease progresses. FIG. 12 shows the decrease in peripheral blood lymphocyte counts over time for a typical HIV-positive patient. This patient did not receive any homeopathic growth factor treatment or conventional HIV therapy, but did receive botanical supplements.

EXAMPLE 4

Figure 13:
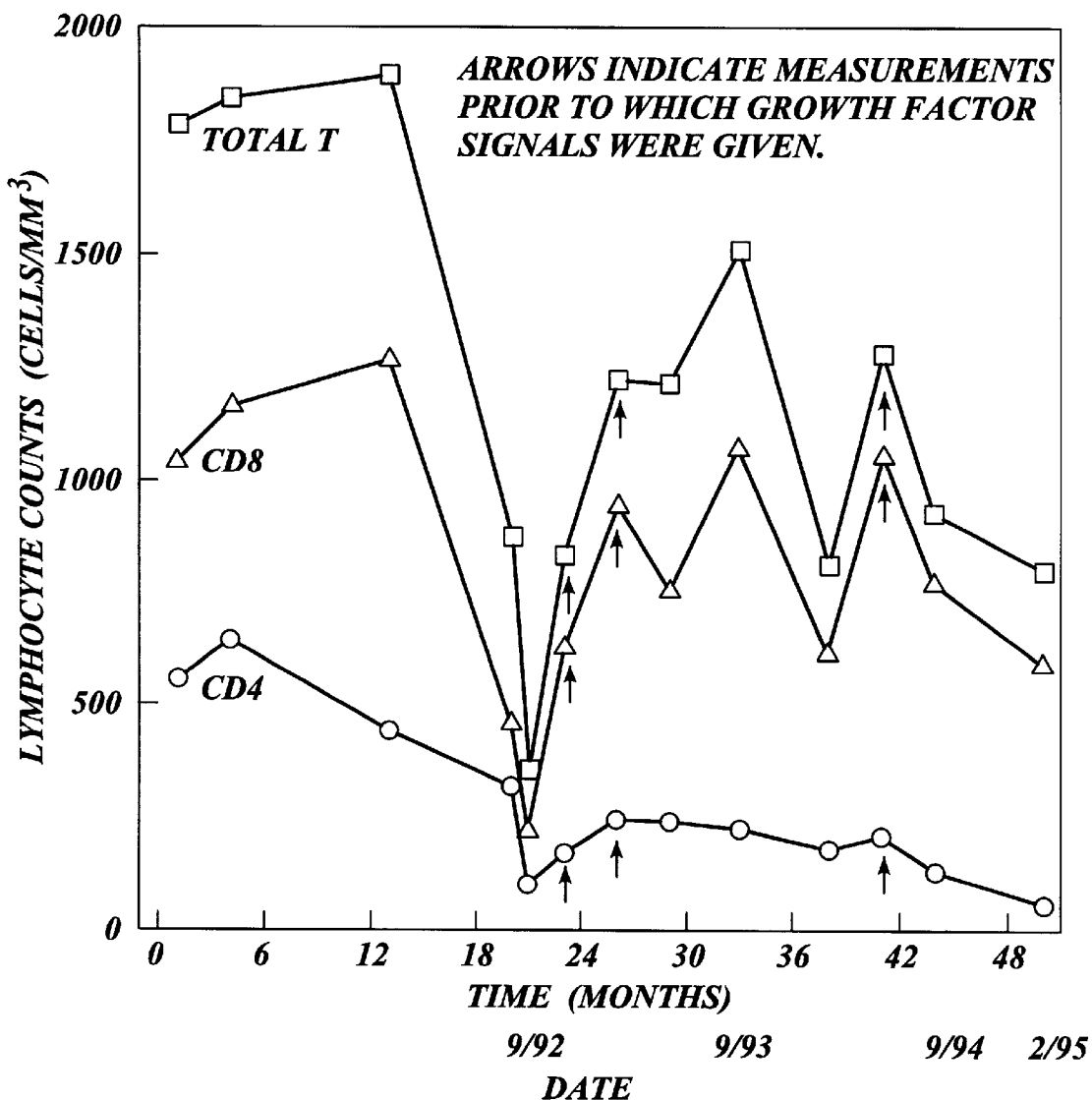
FIG. 13 shows the change in total T lymphocyte cells, CD8 and CD4 counts for an HIV-positive patient prior to and following administration of radio frequency signals corresponding to homeopathic dilutions of growth factors.

FIG. 13 shows the change in total T lymphocyte cell, CD8 and CD4 counts for an HIV-positive patient over a period of four years. This patient was infected with HIV in 1982. In September 1992 (month 21) the CD4 cell count plummeted to 106 cells/mm$^3$. The average annual decrease in CD4 cells in this range is reported to be 32 cells/mm$^3$ when taking anti-retroviral therapeutics (Dept. of Epidemiology, University of Washington). However, after three months of daily treatments with radio frequency signals corresponding to homeopathic dilutions of growth factors, the CD4 cells increased by 138 cells/mm$^3$ and by month 33, in September 1993, the CD4 cell count was 225 cells/mm, 199 cells/mm$^3$ higher than the previous year. Each time the patient received the growth factor radio frequency signals, lymphocyte counts increased. When the patient did not receive the growth factor signals, the CD4 lymphocyte counts dropped, despite the fact that the patient was continually receiving weekly acupuncture treatments.

For example, between months 30 and 33 (June 1993 and September 1993) the patient regularly balanced electrical conductance points (four office visits, no growth factor signals administered). The CD8 and total T lymphocyte cell counts increased 300–350 cells/mm$^3$, but the CD4 cells dropped 17 cells/mm$^3$. The CD4 cells continued to drop until growth factor signals were given regularly (months 38 to 42; February to June 1994). During this time the patient had seven office visits and during four of them (2 in March, 1 in April and 1 in May) was treated with growth factor signals for NGF, AB-PDGF, IGF$_1$, bFGF, and TGF$_\alpha$. During this five month period the patient's CD4 count rose 30 cells/mm$^3$, from 180 cells/mm$^3$ to 210 cells/mm$^3$. The CD8 and total T lymphocyte counts also rose 430–475 cells/mm$^3$. CD8 cell counts above 500 cells/mm$^3$ correlate with low viral replication and perhaps longer survival due to their secretion of growth factors yet to be characterized (1994 International Conference on AIDS).

There was only one time period (months 33–38; Sept. 1993 to February 1994) that a single growth factor signal, IGF$_1$, was given, and CD4, CD8 and total T lymphocyte cell counts dropped 45 cells, 475 cells and 700 cells, respectively. This may be due to only giving one growth factor signal, or more probably to the death of this patient's father, and extensive transcontinental travel and exhaustion during the terminal stages of the father's illness. Grief and loss are well known stress factors that depress immune function. This patient did not receive any conventional drug treatments.

EXAMPLE 5

Figure 14:
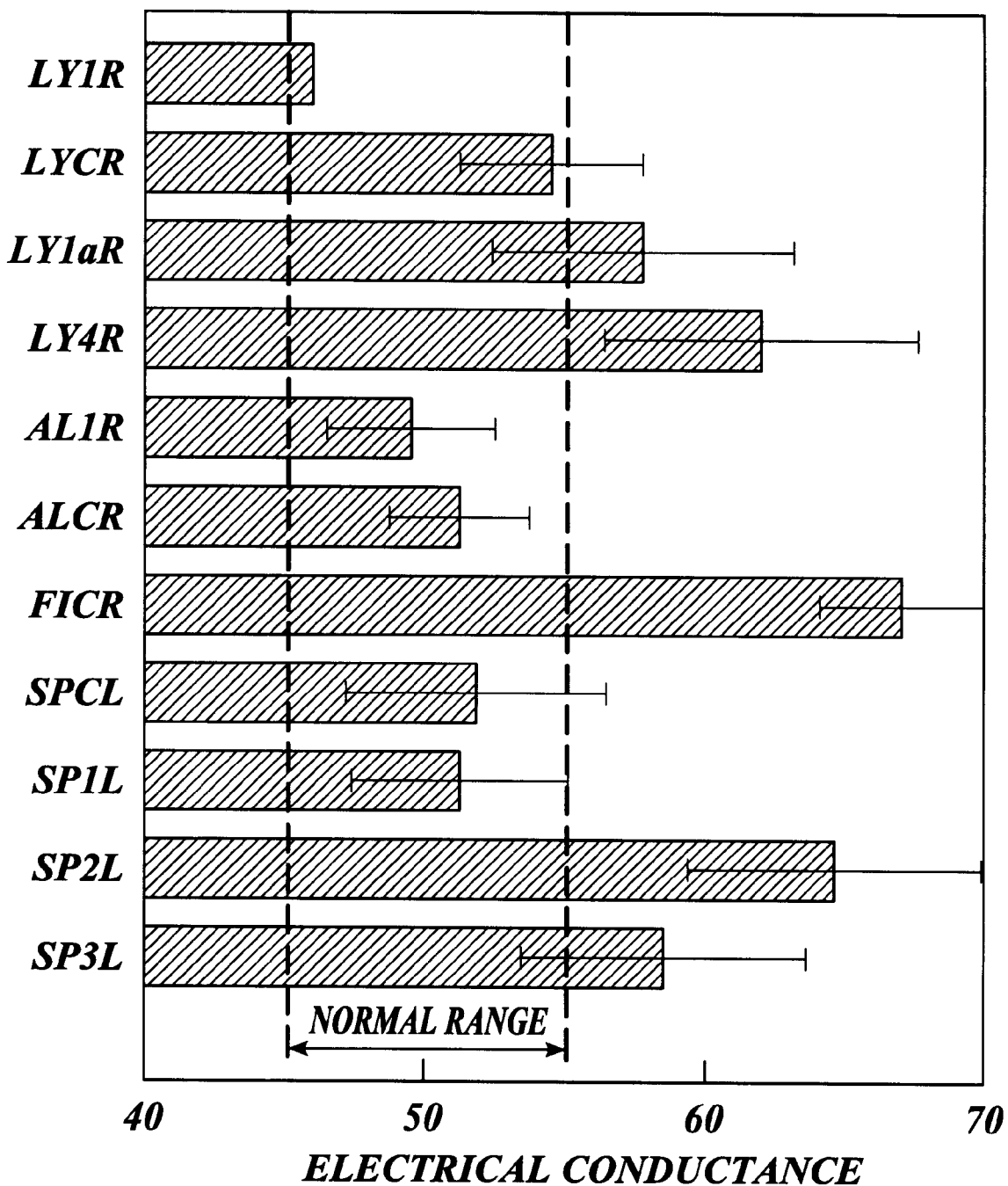
FIG. 14 shows the mean values of electrical conductances for fifteen patients with chronic EBV infection before treatment.

Electrical conductances of fifteen Epstein-Barr virus (EBV) patients were measured at acupuncture points for the immune system using the LISTEN system. The results are shown in FIG. 14. Higher than normal conductances were found at points corresponding to: lymph drainage of tonsils/ throat (LY1aR) lymph tissue of lungs (LY4R); connective tissue (FICR); spleen lymphocytes homing to the lower body and gastrointestinal tract (SP2L); and spleen B lymphocytes and blood purification duties of spleen (SP3L). These results coincide with the clinical symptoms of patients with chronic EBV infection.

Figure 15:
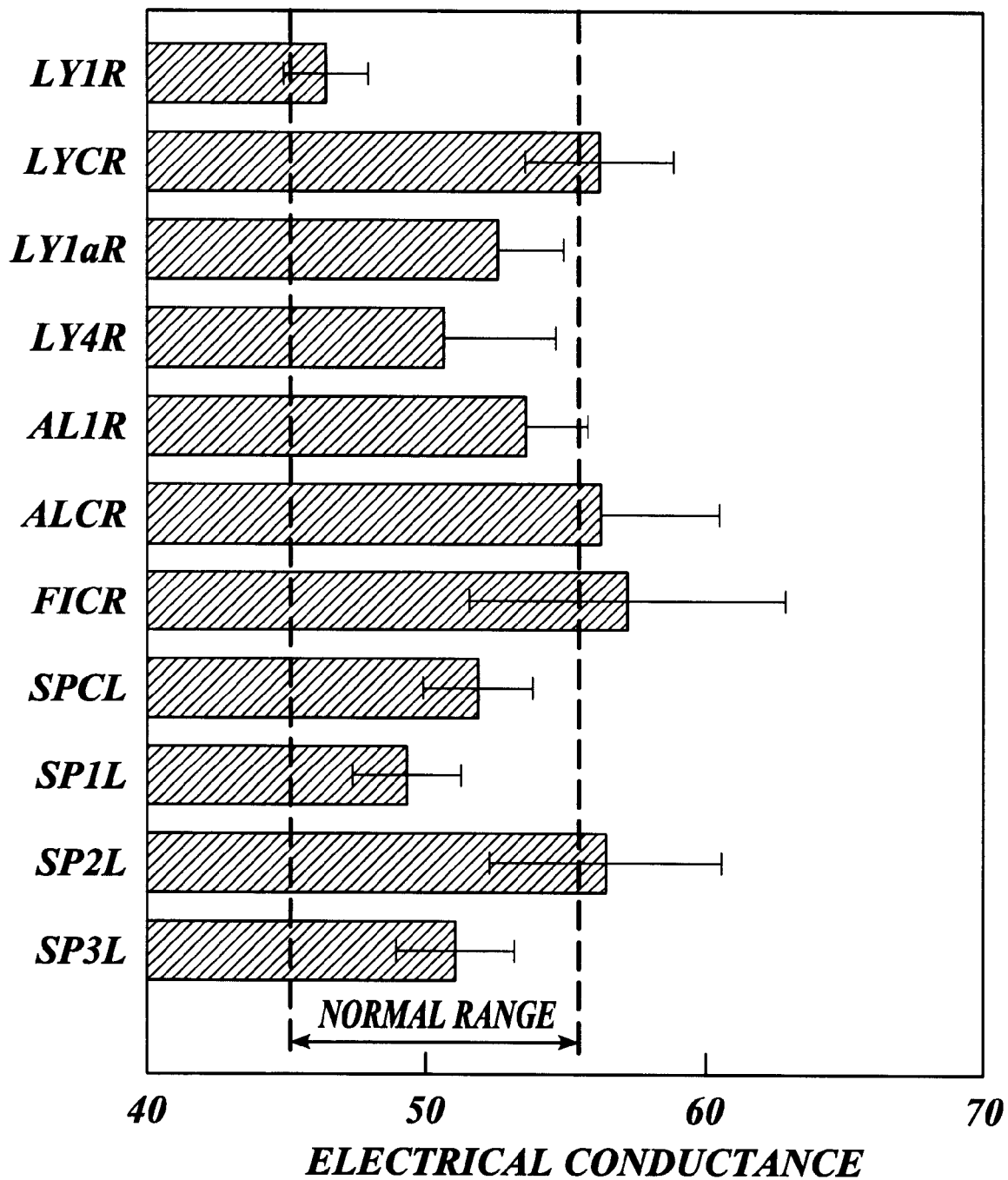
FIG. 15 shows the electrical conductances of eleven EBV patients after treatment with homeopathic growth factor signals and naturopathic supplements.

Eleven of the fifteen patients were subsequently treated for 3–9 months with a combination of homeopathic growth factor signals and botanicals corresponding to the LISTEN digital codes. Each patient was treated once per month using the previously outlined protocol. As shown in FIG. 15, significant improvement in electrical conductances occurred. Fewer clinical symptoms were also observed and reported by the patients. For example, the patients had less upper respiratory distress, less sore throats, more energy, fewer complaints regarding tendonitis, and somewhat improved digestion. These are all typical complaints of EBV patients.

Five of these patients were tested for the ability of signals corresponding to different dilutions of growth factors to normalize electrical conductances during one appointment. The results are shown in Table VI.

TABLE VI

| Patient | EBV Titers | Intake Titer Levels | Growth Factor | Dilution |
|---|---|---|---|---|
| #1 | VCA IgG | 892 | AA PDGF | 6C |
| #2 | VCA IgG | 640 | AA PDGF | 800x, 30C |
|  | EA | 80 | BB PDGF | 800x, 6C |
|  | EBNA | pos | AB PDGF | 800x |
|  |  |  | TGFβ1 | 800x |
|  |  |  | TGFβ2 | 800x |
|  |  |  | TGFαa | 800x |
|  |  |  | bFGF | 6C |
|  |  |  | IGF1 | 800x, 6C 200C, 1000C |
| #3 | VCA IgG | 640 | Stem Cell Factor | 30C |
|  | EA | 80 |  |  |
|  | EBNA | neg |  |  |
| #4 | VCA IgG | 160 | AA PDGF | 6C |
|  | EA | 80 |  |  |
|  | EBNA | pos |  |  |
| #5 | VCA IgG | 1280 | IGF1 | 6C, 12C, 1000C |
|  | EA | neg | Insulin | 30C |
|  | EBNA | 40 | TGFβ1 | 600x, 6C, 1000C |
|  |  |  | βFGF | 6C, 1000C |
|  |  |  | TGFα | 30C, 1000C |
|  |  |  | NGF | 6C |
|  |  |  | Growth Hormone | 1000C |

As outlined above, a dilution of 6 C is equal to 1:100 diluted six times ($10^{12}$ M). A dilution of 800x is equal to 1:10 diluted 800 times.

Prior to treatment, each of the five patients was tested for the presence of the following EBV titers: viral capsid antigen (VCA), early antigen (EA), and Epstein-Barr nuclear antigen (EBNA), as shown in Table III. In non-EBV infected subjects these titers are either negative or close to zero. Patient 1 was symptomatic with sore throat, sinus drainage and swollen glands at time of electrical conductance testing. Patients 2 and 5 were similar in that both had gall bladder surgery, hysterectomies, fibromyalgia, and were over forty and over-weight. Patient 2 also had chronic HPV and HSV infection. Patient 5's fasting blood sugar readings were indicative of mature onset of non-insulin dependent diabetes. Patient 3 was additionally diagnosed as having multiple sclerosis. Patient 4 was additionally diagnosed as having rheumatoid arthritis.

All available growth factor signals were tested for patients 1 and 3–5. Based on the earlier HIV data, potentially useful growth factors were tested on patient 2 to determine effective dilutions, as shown in Table VI.

Patient 5 was balanced on each of seven individual appointments using only growth factors. The growth factors were able to bring the electrical conductances into the normal range of 45–55 at every acupuncture point (over 30 points), often without additional supplementation with naturopathic medicines.

As described earlier all five patients demonstrated improved clinical symptoms. The growth factors found to be effective in treating these EBV patients included PDGF, TGFβ, αFGF, $IGF_1$, NGF, insulin, growth hormone, and stem cell factor.

EXAMPLE 6

Two cancer patients were administered signals corresponding to homeopathic dilutions of growth factors using the standard LISTEN protocol. Patient 1 had chronic myeloid leukemia (CML), which is a stem cell disease in which stem cells fail to respond to physiologic feedback signals that regulate growth and differentiation of hematopoietic precursors. This patient had just begun treatment with alpha-interferon several hours before testing with the LISTEN system. Patient 2 had an adenocarcinoma (renal cell carcinoma) removed from her left side approximately 18 months prior to this study, and had metastases to the lung, skull and possibly to the bones and liver at the commencement of this study.

Figure 16:
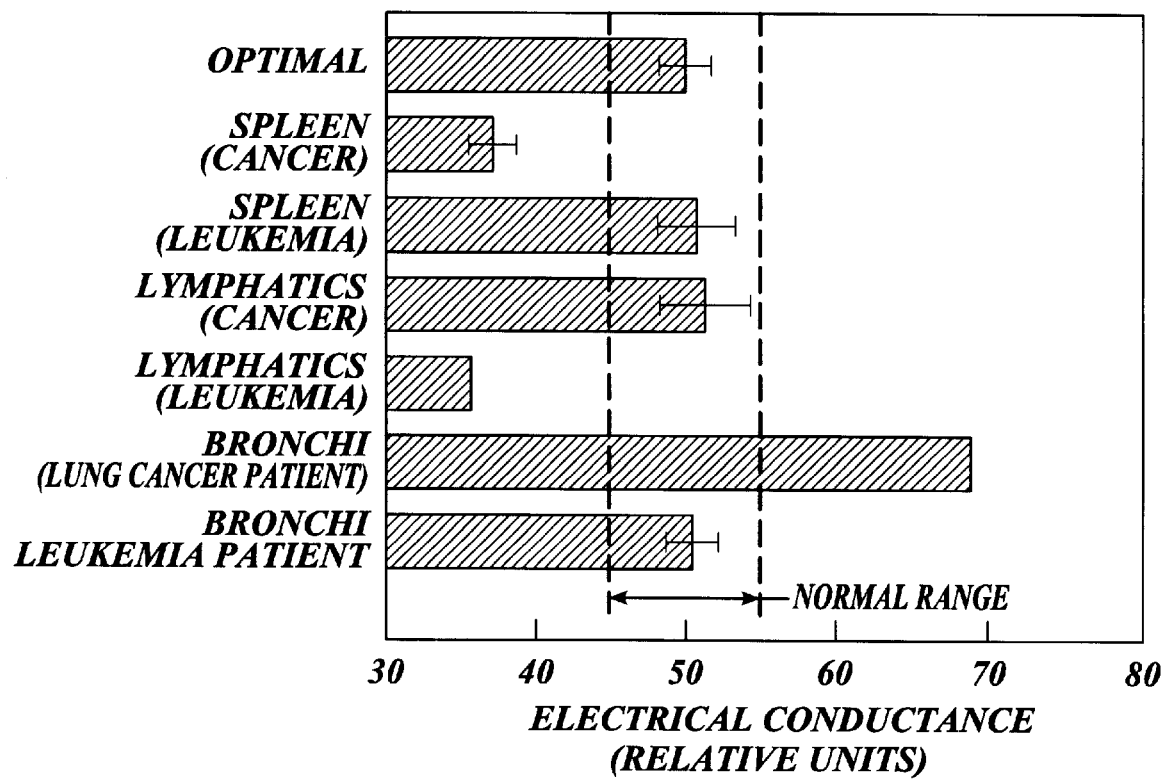
FIG. 16 shows the electrical conductances for two cancer patients prior to treatment with the LISTEN system.

As shown in FIG. 16, these two patients had significantly different electrical conductances. Both patients' electrical conductances were normalized by administration of specific homeopathic growth factor signals and naturopathic supplements. For patient 1, signals corresponding to combined dilutions of IGFI were found to bring the conductances back into the normal range. For patient 2, signals corresponding to 30x, 100 C and 1000 C dilutions of NGF, an 8x dilution of AA PDGF, and 6 C and 30 C dilutions of TGFβ1 were found to be effective. The naturopathic supplements alone did not balance the electrical conductances.

Patient 2, following treatment using the LISTEN system five times per week for one month, no longer tested positive for cancer, using the serum AMAS™ test (Anti-Malignin Antibody in Serum determined with TARGET™ Reagent; Oncolab, Inc., Boston, Mass.; Abrams, M. B. et al. 1994 Cancer Detection and Prevention 18:65–78). In this test, the higher the component result number, the more indicative the result is of cancer. The AMAS™ normal range for S-TAG is 0–399; for F-TAG 0–299; and for net-TAG 0–99. The specific results of the AMAS™ test for this patient after one month of treatment were as follows: S-TAG 184 µg/ml (normal); F-TAG 79 µg/ml (normal); and net-TAG 105 µg/ml (borderline). AMAS™ test results continued to improve with continued administration of radio frequency signals corresponding to homeopathic dilutions of growth factors. Two months later, after continued treatment, the results of the AMAS™ test were as follows: S-TAG 152 µg/ml (17% decrease); F-TAG 70 µg/ml (11% decrease) and net-TAG 82 µg/ml (now in normal range with a 22% decrease). All component measurements indicated that normal results had been achieved. The results of blood chemistry analyses for Patient 2 before treatment and after one month of treatment with signals corresponding to TGFβ1 are shown in Table VII.

TABLE VII

| Blood Chemistry | Before Treatment | After Treatment |
| --- | --- | --- |
| Chemistry | | |
| Sodium | 139 meg/l | 143 |
| Potassium | 3.3 meg/l | 4.8 |
| Chloride | 100 meg/l | 108 |
| $CO_2$ | 25 meg/l | 23 |
| Glucose | 173 (high) mg/dl | 149 (high but closer to normal) |
| Calcium | 8.7 mg/dl | 9.0 |
| Bun | 18.0 mg/dl | 18.0 |
| Creatinine | 1.2 mg/dl | 1.2 |
| Bun/Creat. | 15.0 | 15.1 |
| Uric Acid | 5.5 mg/dl | 6.2 (high) |
| Cholesterol | 301 (high) mg/dl | 357 (high) |
| Triglycerides | 523 (high) | 305 (high but closer to normal) |
| Albumin | 4.0 g/dl | 4.1 |
| Globulin | 2.6 g/dl | 2.5 |
| A/G ratio | 1.5 | 1.6 |
| Total Bilirubin | 0.6 mg/dl | 0.4 |
| Direct Bilirubin | 0.4 mg/dl | 0.0 |
| Alkaline Phosphatase | 62 u/l | 108 |
| LDH | 136 u/l | 150 |
| AST (SGOT) | 8 u/l | 15 |
| ALT (SGPT) | 8 u/l | 18 |
| CBC | | |
| WBC | 7x1000/ul | 5.9 |
| RBC | 3.93 (Low) mil/ul | 4.49 (resolved) |
| Hemoglobin | 11.7 (Low) g/dl | 13.6 (resolved) |
| Hematocrit | 35.1 (Low) % | 41.7 (resolved) |
| MCV | 89.3 fl | 92.9 |
| MCH | 29.8 pg | 30.3 |
| MCHC | 33.3% | 32.6 |
| Neutrophils | 55.9% | 62.9% |
| Lymphocytes | 34.4% | 32.7% |
| Monocytes | 7.4% (monocytosis) | 2.4% (resolved) |
| Eosinophils | 1.4% | 1.2% |
| Basophils | 0.9% | 0.8% |
| Platelet count | 342,000/ul | 348,000/ul |

Prior to treatment, Patient2 had anemia, as indicated by the hemoglobin, hematocrit and red blood cell count (RBC), and immune stress, indicated by slightly elevated 5 monocyte counts. Following treatment with radio frequency signals corresponding to TGFb1 for a period of one month, the patient's anemia and monocytosis had resolved. The patient's liver enzyme values (SGOT and SGPT) were also greatly improved, as was the alkaline phosphatase level.

EXAMPLE 7

Figure 17:
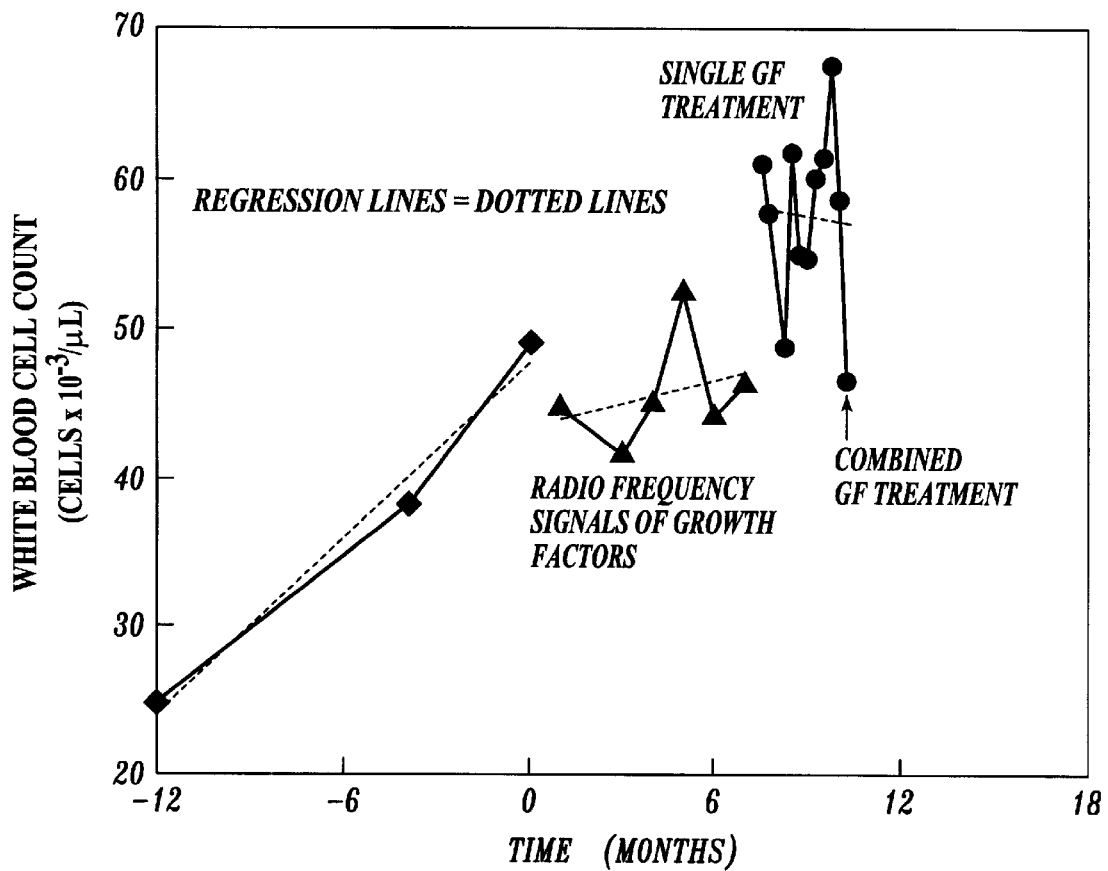
FIG. 17 shows the change in white blood cell count in a patient with chronic lymphocytic leukemia both before and during treatment with radio frequency signals corresponding to homeopathic dilutions of growth factors and homeopathic liquid dilutions of growth factors.

FIG. 17 shows the change in white blood cell count in a patient with chronic lymphocytic leukemia both before and during treatment first with radio frequency signals corresponding to homeopathic dilutions of growth factors and subsequently with both radio signals in combination with orally administered homeopathic dilutions of growth factors.

This patient was diagnosed with chronic lymphocytic leukemia in April 1992. From April 1993 to April 1994 (months—12 to 0 on the time scale) the white blood cell count doubled from 24,700 to 49,000 cells/mm3. In April 1994 (months 0 to 7) the patient began receiving radio frequency signals corresponding to growth factors on a weekly basis. During this treatment period, the white blood cell count maintained a relatively low non-progressive state, as noted by the significantly different regression line during that time versus the general treatment period regression line. The patient initially progressed to higher counts of white blood cells when orally administered $10^{-12}$M and $10^{-24}$M dilutions of GM-CSF plus radio frequency signals corresponding to homeopathic dilutions of growth factors. The white blood cell counts were dramatically decreased by introducing homeopathic dilutions of $10^{-60}$M and $10^{-2,000}$M BB-PDGF plus a homeopathic dilution of HH6V into the protocol. With the addition of $10^{-60}$M and $10^{-2,000}$M TGFβ to the protocol, the patient's white blood cell count dropped back down to 41,000 cells/mm$^3$. The regression line demonstrates a downward trend.

EXAMPLE 8

The effectiveness of oral administration of homeopathic dilutions of growth factors in the treatment of diabetes was investigated as follows.

Figure 18:
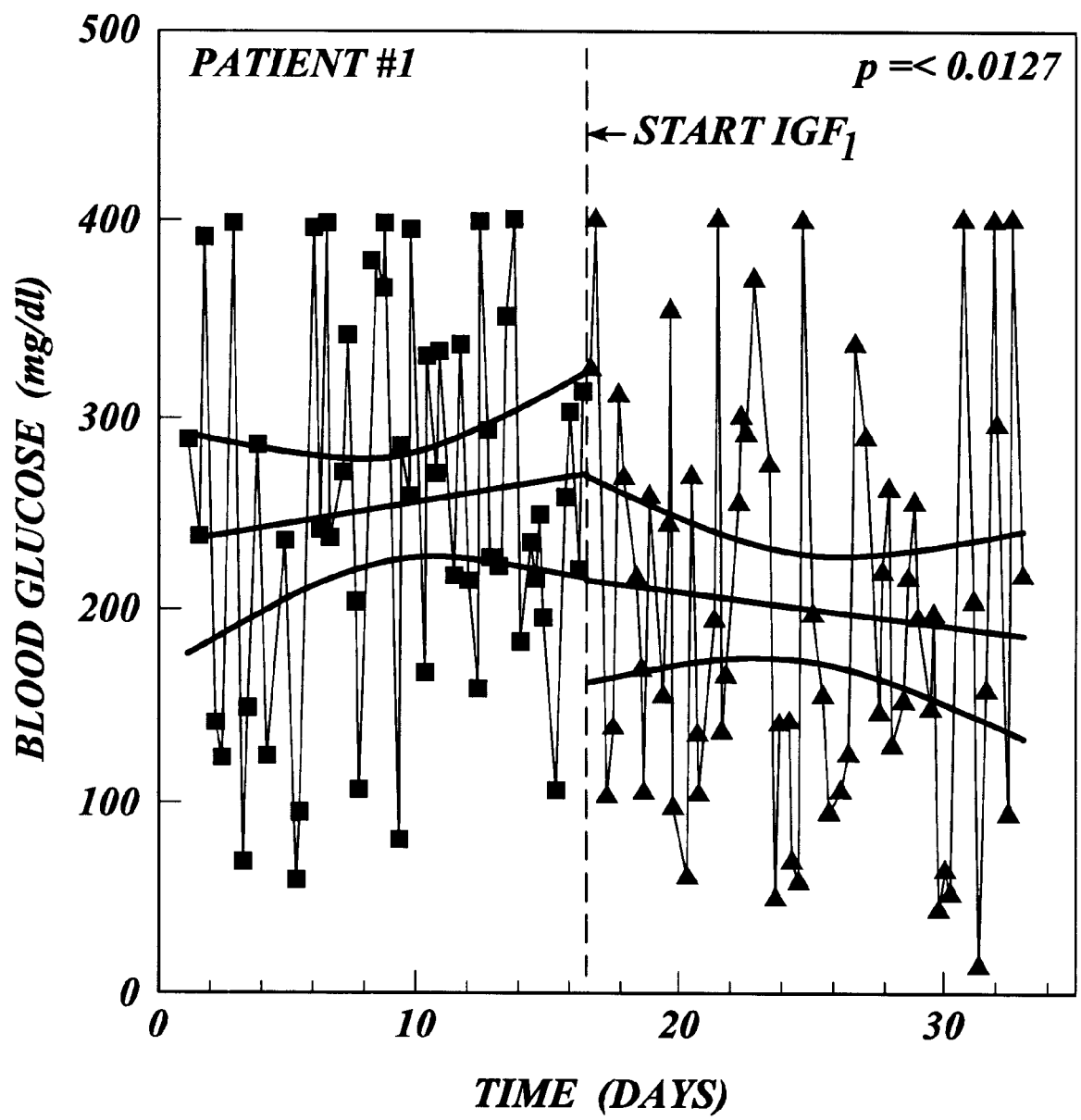
FIG. 18 shows the blood glucose levels of a patient with insulin dependent diabetes both before and during treatment with homeopathic dilutions of insulin-like growth factor.

A patient with insulin-dependent diabetes was treated with 6 C insulin-like growth factor ($IGF_1$; prepared as described in EXAMPLE 1) daily for a period of 18 days. The patient was taking insulin both prior to and during treatment with homeopathic $IGF_1$. As shown by the regression line of FIG. 18, the patient's blood glucose levels were lowered during the treatment period, compared to the 16 day period immediately prior to commencement of treatment with homeopathic $IGF_1$. During week 2 of treatment with homeopathic $IGF_1$ (days 23–29 of the study), the patient's insulin use dropped to a mean of 22.29 compared to a mean of 36.93 during the 16 day period prior to commencement of treatment with homeopathic $IGF_1$ ($p<0.0558$). The difference in insulin use during weeks I (day 16–22) and 3 (days 30–32) of the study compared to the period prior to treatment was not statistically significant.

EXAMPLE 9

Figure 19:
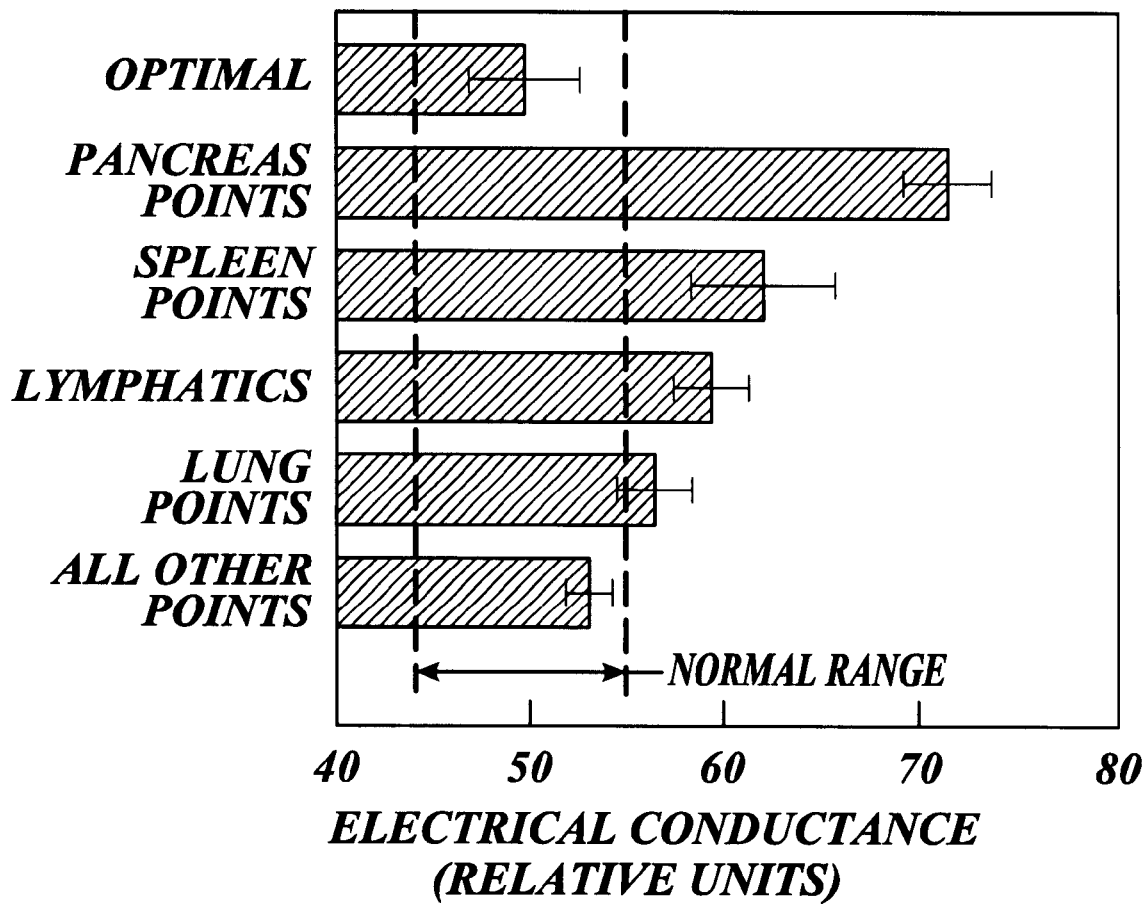
FIG. 19 shows the electrical conductances for two patients with insulin dependent diabetes prior to treatment with the LISTEN system.

A study was performed using the LISTEN system on two patients with insulin-dependent diabetes. Both patients were between 11 and 12 years of age and were treated within one year of onset of disease. Patient 1 serum-tested positive for Coxsackie B3 virus, which has been implicated through epidemiological studies to be a causative factor in the onset of diabetes. Patient 2 was not tested for Coxsackie B virus. The highly abnormal conductances of these patients shown in FIG. 19 were brought into the normal range by the administration of signals corresponding to naturopathic supplements plus a 6 C dilution of insulin. On one occasion, patient 1's conductance points were completely balanced with signals corresponding to combined dilutions of stem cell factor or vasopressin without the need for additional signals of naturopathic supplements. These corrections in electrical conductance correspond with greater control of blood glucose level.

In a separate treatment session, all available signals for homeopathic growth factors were scanned to determine which signal would bring patient 2's conductances back to the normal range. A signal corresponding to a 600× dilution of βFGF was found to be most effective.

EXAMPLE 10

The effectiveness of homeopathic dilutions of growth factors in the treatment of clinical depression was determined as follows.

Homeopathic dilutions of insulin-like growth factor (IGF1) were administered to seven patients who had been diagnosed as being clinically depressed by a psychotherapist but who were otherwise healthy. Specifically, 10 drops of 1M ($10^{-2,000}$) $IGF_1$ (prepared as described in EXAMPLE 1) were administered orally three times per day for a period of three months. The mental and physical status of the patients was evaluated throughout the study period using the standard Beck's Inventory and the Bastyr AIDS Research Center instrument referred to as the Review of Systems form.

Figure 20:
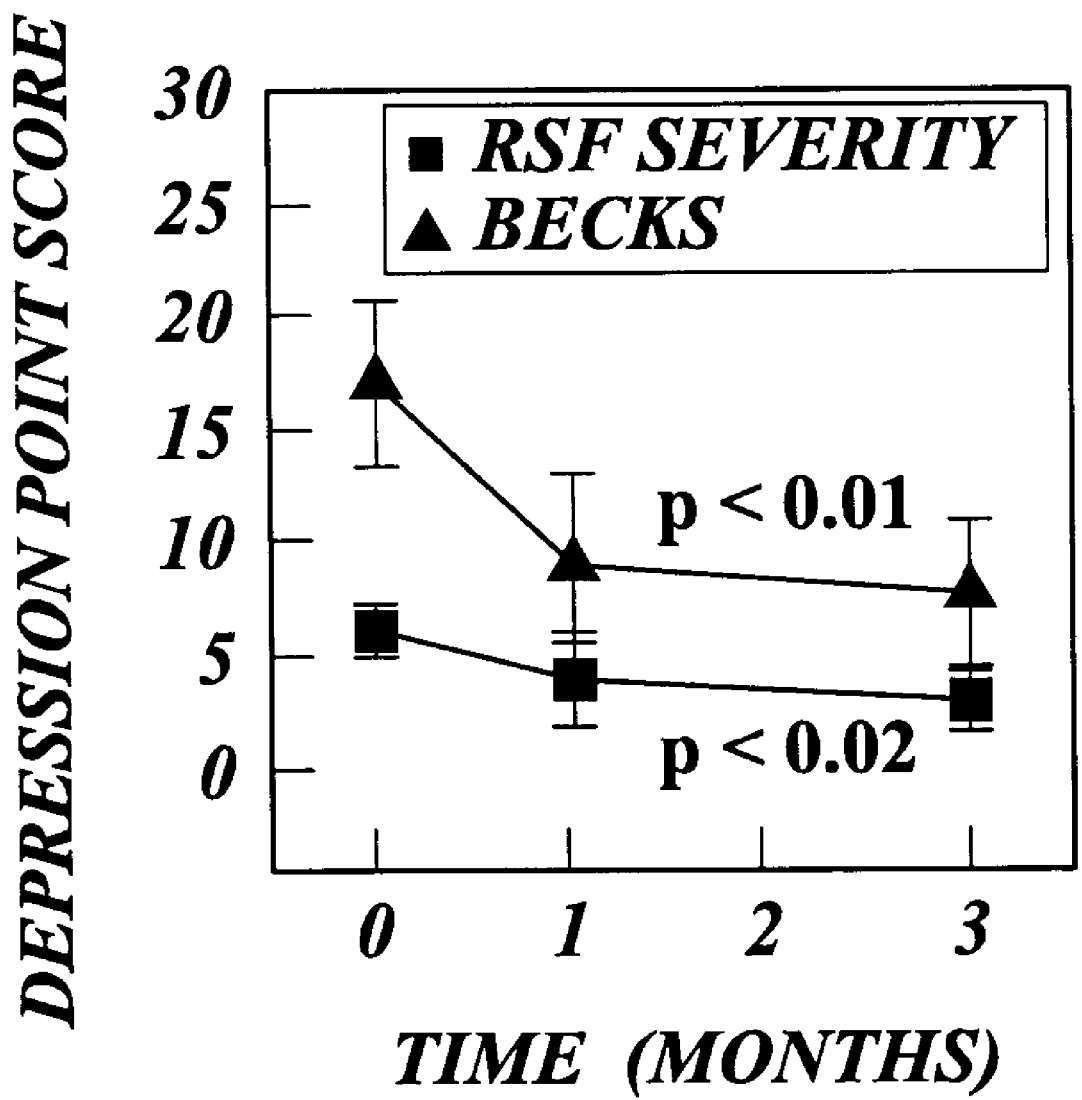
FIG. 20 shows the change in depression levels as measured by Becks depression and severity scores for eight depressed, but otherwise healthy, patients during three months of treatment with homeopathic dilutions of insulin-like growth factor-1 ($IGF_1$).

As shown in FIG. 20, oral administration of homeopathic dilutions of $IGF_1$ resulted in a significant decrease in depression levels. Prior to the commencement of treatment, Becks depression and severity scores were 17.0±4.0 and 6.0±3.0, respectively. After three months of treatment, the Becks depression and severity scores decreased to 8.0±3.0 ($P<0.01$) and 3.0±1.0 ($P<0.02$), respectively.

EXAMPLE 11

A 6 C homeopathic preparation of $TGF_{\beta1}$, in a solution of USP purified water, glycerin, citric acid and sodium benzoate as a preservative was taken orally by eight subjects in generally good health. Ten drops of the preparation were taken three times daily for five days. Each subject filled out a review of systems form on a daily basis, rating his or her responses for the following conditions: fatigue, fever, night sweats, weight loss, wasting, anorexia, malaise, lymph node enlargement, lymph node pain, canker sores, painful gums, thrush, oral hairy leukoplakia, Kaposi's sarcoma in mouth, oral herpes, painful/bleeding gums, nausea, abdominal pain, abdominal bloating, pain when swallowing, diarrhea, constipation, poor appetite, rectal warts, rectal herpes, hemorrhoids, rectal fissure, rectal bleeding, rectal itching, skin rashes, skin itching, Kaposi's sarcoma, herpes simples, shingles, dry scaly skin, vision changes, floaters, photophobia, eye inflammation, cough, shortness of breath, nasal congestion, sinus congestion, phlegm, wheezing, painful breathing, genitourinary discharge, decreased libido, genitourinary ulcerations, genital warts, genital herpes, joint pain, muscle pain, muscle wasting, headaches, confusion, poor short term memory, peripheral neuropathy, seizures, weakness in arms/legs, tingling/burning sensation, blackouts, apathy, mood swings, depression, anxiety, anger, ringing in the ears, bilateral jaw tenderness, jaw pain, facial swelling, facial flushing, paleness of face, parotid gland swelling, difficulty breathing, fast heartbeat, swelling, trembling, discomfort between shoulder blades, back pain, muscle weakness and blurred vision. The results are shown in Table VIII, below, indicating the number of patients responding for each condition for which more than two patients responded during treatment with the homeopathic preparation. A response may indicate that the symptom was provoked or relieved for a particular patient. The fact that a particular symptom or condition may be provoked by a substance has significance for homeopathic treatments which observe the Law of Similars.

TABLE VIII

| CONDITION | NUMBER OF PATIENTS RESPONDING |
|---|---|
| FATIGUE | 6 |
| MALAISE | 2 |
| PAIN | 2 |
| PAINFUL/BLEEDING GUMS | 3 |

TABLE VIII-continued

| CONDITION | NUMBER OF PATIENTS RESPONDING |
|---|---|
| BLOATING | 2 |
| DIARRHEA | 2 |
| HEMORRHOIDS | 2 |
| DRY SCALY SKIN | 5 |
| VISION CHANGES | 2 |
| NASAL CONGESTION | 4 |
| SINUS CONGESTION | 5 |
| PHLEGM | 3 |
| DECREASED LIBIDO | 3 |
| JOINT PAIN | 2 |
| MUSCLE PAIN | 3 |
| HEADACHES | 4 |
| APATHY | 2 |
| MOOD SWINGS | 5 |
| DEPRESSION | 3 |
| ANXIETY | 3 |
| ANGER | 3 |
| FACIAL FLUSHING | 2 |
| BACK PAIN | 3 |

EXAMPLE 12

6 C and 1M homeopathic preparations of IGF-1 in a solution of USP purified water, glycerin, citric acid and sodium benzoate as a preservative were taken orally by eight patients in generally good health. Ten drops of the 6 C preparation were taken three times daily for five days by two subjects, and ten drops of the 1M preparation were taken three times daily for approximately seven to fourteen weeks by six subjects. Each subject taking the 6 C treatment filled out a review of systems form on a daily basis and each subject taking the 1M treatment filled out a review of systems form on a monthly basis, rating his or her responses for the following conditions: fatigue, fever, night sweats, weight loss, wasting, anorexia, malaise, lymph node enlargement, lymph node pain, canker sores, painful gums, thrush, oral hairy leukoplakia, Kaposi's sarcoma in mouth, oral herpes, painful/bleeding gums, nausea, abdominal pain, abdominal bloating, pain when swallowing, diarrhea, constipation, poor appetite, rectal warts, rectal herpes, hemorrhoids, rectal fissure, rectal bleeding, rectal itching, skin rashes, skin itching, Kaposi's sarcoma, herpes simples, shingles, dry scaly skin, vision changes, floaters, photophobia, eye inflammation, cough, shortness of breath, nasal congestion, sinus congestion, phlegm, wheezing, painful breathing, genitourinary discharge, decreased libido, genitourinary ulcerations, genital warts, genital herpes, joint pain, muscle pain, muscle wasting, headaches, confusion, poor short term memory, peripheral neuropathy, seizures, weakness in arms/legs, tingling/burning sensation, blackouts, apathy, mood swings, depression, anxiety, anger, ringing in the ears, bilateral jaw tenderness, jaw pain, facial swelling, facial flushing, paleness of face, parotid gland swelling, difficulty breathing, fast heartbeat, swelling, trembling, discomfort between shoulder blades, back pain, muscle weakness and blurred vision. The results are shown in Table IX, below, indicating the number of patients responding for each condition for which more than two patients responded during treatment with the homeopathic preparation. A response may indicate that the symptom was provoked or relieved for a particular patient. The fact that a particular symptom or condition may be provoked by a substance has significance for homeopathic treatments which observe the Law of Similars.

TABLE IX

| CONDITION | NUMBER OF PATIENTS RESPONDING |
|---|---|
| FATIGUE | 7 |
| WEIGHT LOSS | 2 |
| MALAISE | 2 |
| CANKER SORES | 4 |
| PAINFUL/BLEEDING GUMS | 2 |
| BLOATING | 5 |
| CONSTIPATION | 4 |
| HEMORRHOIDS | 3 |
| RECTAL BLEEDING | 3 |
| RASHES | 3 |
| ITCHING | 4 |
| DRY SCALY SKIN | 4 |
| VISION CHANGES | 4 |
| EYE FLOATERS | 2 |
| EYE INFLAMMATION | 4 |
| COUGH | 4 |
| SHORTNESS OF BREATH | 3 |
| NASAL CONGESTION | 5 |
| SINUS CONGESTION | 5 |
| PHLEGM | 7 |
| GENITO URINARY DISCHARGE | 3 |
| DECREASED LIBIDO | 3 |
| JOINT PAIN | 6 |
| MUSCLE PAIN | 3 |
| HEADACHES | 4 |
| CONFUSION | 6 |
| POOR SHORT TERM MEMORY | 5 |
| WEAKNESS IN ARMS/LEGS | 5 |
| TINGLING/BURNING SENSATION | 2 |
| APATHY | 4 |
| MOOD SWINGS | 3 |
| DEPRESSION | 6 |
| ANXIETY | 7 |
| ANGER | 3 |

EXAMPLE 13

A thirty-four year old overweight female subject took a combination of the following homeopathic preparations of growth factors: 30 C and 1M $PDGF_{BB}$, 30 C and 1M $TGF_{\beta1}$, and 30 C $IGF_1$, all in water and glycerin-based diluents for oral administration.

Prior to taking the homeopathic preparations, a reading from a BioAnalogics ELG Quick-Comp machine measured the following amount of lean muscle mass and fat in the subject's body: 43.4% body fat at 109 pounds; 56.6% lean mass at 142 pounds. Her weight was 251 pounds. During the eight days this subject took the homeopathic preparations of growth factors, she ate and drank more than usual quantities. After eight days of the homeopathic treatment described above, she had lost two pounds, and a reading from a BioAnalogics ELG Quick-Comp machine measured the following amount of lean muscle mass and fat in her body: 39.3% body fat at 98 pounds; 60.7% lean mass at 151 pounds. The number of calories required to be consumed daily in a resting state, as determined by the BioAnalogics device, increased from 1882 to 1970 during the course of the treatment with homeopathic preparations of growth factors.

EXAMPLE 14

A fifty-four year old female subject having a TMJ problem and substantial jaw pain took the following homeopathic preparations of growth factors for two and one-half months: 1M $IGF_1$; 30 C and 1M $PDGF_{BB}$, and 30 C $IGF_1$, all in water and glycerin-based diluents for oral administration. She additionally took 30 C and 1M $TGF_{\beta1}$ for several weeks during that time period.

The first observation made by the subject was that her reading vision improved significantly—to the point that she didn't need to use her reading glasses at times. That effect diminished when she stopped taking $TGF_{\beta1}$. Her TMJ pain, which had been chronic, diminished to the point that she was pain-free, and the TMJ pain did not returned. She did not lose weight, but she lost inches in her hips and waist. Her subjective observation was that her upper body seemed to be stronger and leaner, and her arms had significantly more muscle tone. Neither her exercise habits nor her diet changed during her treatment with homeopathic preparations of growth factors.

EXAMPLE 15

A male subject who regularly lifted weights took a 1M homeopathic preparation of $IGF_1$, for approximate 6 to 8 weeks. During the treatment, the subject's weight lifting performance improved and his workout partner observed that the subject was lifting more weight per exercise, and that his body appeared to have more muscle definition. Specific weight lifting performance increases include: improving on the hammer bench press machine from the 230 lb range to a maximum in excess of 270 lbs; improving on the hammer curl machine from 110 lb; and improving on the leg press machine, with maximum sets improving from 630 lbs. To 720 lbs. The subject believed that the effects of the homeopathic preparation continued for about 4–6 weeks following the treatment.

EXAMPLE 16

Another subject who regularly lifted weights took a 1M homeopathic preparation of $IGF_1$. This subject observed a reduction in muscle recovery time and increase in overall strength during treatment with the homeopathic preparation of $IGF_1$. Specifically, the subject ordinarily experienced substantial soreness in the muscles and supporting muscles worked the previous day. During treatment, the subject could work the same muscles after a 24 hour recovery period with little, if any soreness. The subject's trainer observed a noticeable increase in strength and weight gain—and charted a 20–30% increase in strength within 3–5 days following the start of treatment.

In addition to the physical benefits of the treatment, this patient observed an increased clarity and focus of thought during the treatment. Objectives, both in working out and in other areas of life seemed more attainable and there were fewer obstacles.

EXAMPLE 17

A male subject has worked out extensively with a trainer for several years. Initially he lost a substantial amount of weight and gained substantial muscle mass and strength. For the past year, this subject reached a plateau, lost little weight and gained little lean muscle mass, despite working out consistently and eating a high protein diet. When the subject changed his diet to one less rich in protein, particularly animal protein and heavier in vegetables and fruits, and lost a couple of pounds. During a one week treatment with 30 C $IGF_1$, the subject lost 8 pounds of fat and gained 3 pounds of lean muscle mass. Both the subject and his trainer observed a noticeable increase in overall strength during treatment with the homeopathic preparation of $IGF_1$.

EXAMPLE 18

A subject having crippling pain in the right hip and leg, frequent allergic reactions resulting in Meniere's attacks, nightly violent muscle spasms in legs and feed, and severe abdominal bloating was treated for six weeks with 1M IGF$_1$ and 30 C and 1M PDGF$_{BB}$, in water and glycerin-based diluents for oral administration. During the six week treatment period, improvements in all of these conditions were observed. The crippling pain in her right hip and leg almost dissipated; the frequent allergic reactions resulting in Meniere's attacks decreased to very few; the nightly violent muscle spasms and consequent loss of sleep lessened; and the severe abdominal bloating decreased. In addition to less pain and more and better sleep, this subject observed a general feeling of increased wellness and strength.

EXAMPLE 19

A forty-four year old female subject began treatment with 30 C IGF$_1$ during a period of person crisis when she felt overwhelmed and depressed, particularly due to the demands of her job as a nurse practitioner in an international health care agency. This subject has generally had to exert a great deal of energy to be able to think through and discuss ides in an organized manner. Her clarity of thought and organization is much reduced during periods of stress and overwhelm.

Following treatment with 30 C IGF$_1$ for just a few days, this subject observed that she was effectively sorting through all kinds of situations and organizing and presenting her thoughts in an order way, with appropriate emotions attached. She was able to identify problems that heeded to be addressed and could develop and act on plans to resolve those problems, rather than being overwhelmed by them. Since beginning treatment with the homeopathic preparation of IGF$_1$ she could help clarify discussions, and present her assessments and arguments more effectively. This subject feels that she is making real progress in dealing with the chronic mental confusion and chaos that she previously believed was an integral part of her life.

Although the present invention has been described in terms of specific embodiments, changes and modifications can be carried out without departing from the scope of the invention which is intended to be limited only by the scope of the appended claims.

I claim:

1. A method for modifying blood lymphocyte counts in a patient comprising administering a homeopathic preparation of one or more growth factors, said homeopathic preparation comprising a molar concentration of between $1 \times 10^{-6}$ and $1 \times 10^{-100,000}$ of the one or more growth factors.

2. A method for modifying blood lymphocyte counts as recited in claim 1, wherein said one or more growth factors is selected from the group consisting of granulocyte macrophage-colony stimulating factor (GM-CSF), granulocyte-colony stimulating factor (G-CSF), macrophage-colony stimulating factor (M-CSF), tumor necrosis factors (TNFα and TNFβ), transforming growth factors (TGFα and TGFβ), epidermal growth factors (EGF), stem cell factor (SCF), platelet-derived growth factors (PDGF), platelet-derived endothelial cell growth factor, nerve growth factor (NGF), fibroblast growth factors (FGF), insulin-like growth factors (IGF-I and IGF-II), growth hormone, interleukins 1 to 13 (IL-1 to IL-13), interferons α, β and γ (IFN-α, IFN-β and IFN-γ), brain-derived neurotrophic factor, neurotrophins 3 and 4, hepatocyte growth factor, erythropoictin, EGF-like mitogens, TGF-like growth factors, PDGF-like growth factors, melanocyte growth factor, mammary-derived growth factor 1, prostate growth factors, cartilage-derived growth factor, chondrocyte growth factor, bone-derived growth factor, osteosarcoma-derived growth factor, glial growth-promoting factor, colostrum basic growth factor, endothelial cell growth factor, tumor angiogenesis factor, hematopoietic stem cell growth factor, B-cell stimulating factor 2, B-cell differentiation factor, leukemia-derived growth factor, myelomonocytic growth factor, macrophage-derived growth factor, macrophage-activating factor, erythroid-potentiating activity, keratinocyte growth factor, ciliary neurotrophic growth factor, Schwann cell-derived growth factor, vaccinia virus growth factor, bombyxin, neu differentiation factor, v-Sis, glial growth factor/acetylcholine receptor-inducing activity, transferrin, bombesin and bombesin-like peptides, angiotensin II, endothelin, atrial natriuretic factor (ANF) and ANF-like peptides, vasoactive intestinal peptide, and Bradykinin.

3. A method according to claim 1, wherein the homeopathic preparation is in the form of a solution and has a homeopathic potency of at least one growth factor selected from the following homeopathic potencies: 6 C, 30 C, 200 C and 1M.

4. A method according to claim 1, wherein the homeopathic preparation comprises two homeopathic potencies of at least one growth factor.

5. A method according to claim 1, wherein the homeopathic preparation is in the form of a solution and the one or more growth factors is selected from the group consisting of IGF-1, PDGF$_{BB}$, TGF$_{β1}$, GM-CSF and NGF.

6. A method according to claim 1, wherein the one or more growth factors includes IGF-1.

7. A method according to claim 6, wherein the one or more growth factors includes IGF-1 at a homeopathic potency of 1M.

8. A method according to claim 1, wherein the one or more growth factors includes PDGF$_{BB}$.

9. A method according to claim 8, wherein the one or more growth factors includes PDGF$_{BB}$ at a homeopathic potency of 30 C.

10. A method according to claim 8, wherein the one or more growth factors includes PDGF$_{BB}$ at a homeopathic potency of 1M.

11. A method according to claim 1, wherein the one or more growth factors includes TGF$_{β1}$.

12. A method according to claim 10, wherein the one or more growth factors includes TGF$_{β1}$ at a homeopathic potency of 30 C.

13. A method according to claim 10, wherein the one or more growth factors includes TGF$_{β1}$ at a homeopathic potency of 1M.

14. A method according to claim 1, wherein the one or more growth factors includes GM-CSF.

15. A method according to claim 14, wherein the one or more growth factors includes GM-CSF at a homeopathic potency of 200 C.

16. A method according to claim 1, wherein the one or more growth factors includes NGF.

17. A method according to claim 1, wherein the homeopathic preparation is in the form of a tablet or capsule and the one or more growth factors is selected from the group consisting of IGF-1, PDGF$_{BB}$, TGF$_{β1}$, GM-CSF, and NGF.

18. A method according to claim 1, wherein in the homeopathic preparation is in the form suitable for topical application.

19. A method for increasing blood lymphocyte counts in a patient comprising administering to the patient a preparation comprising a homeopathic potency of one or more growth factors selected from the group consisting of: IGF-1, PDGF$_{BB}$, TGF$_{β1}$, GM-CSF and NGF.

20. A method of claim 19, wherein the one or more growth factors has a homeopathic potency of 6 C, 30 C, 200 C or 1M.

21. A method of claim 19, wherein the preparation comprises two homeopathic potencies of at least one growth factor.

* * * * *